US009890414B2

(12) United States Patent
Maruyama et al.

(10) Patent No.: US 9,890,414 B2
(45) Date of Patent: Feb. 13, 2018

(54) PREPARATION OF GENE-SPECIFIC TEMPLATES FOR THE USE IN SINGLE PRIMER AMPLIFICATION

(71) Applicant: Abwiz Bio, Inc., San Diego, CA (US)

(72) Inventors: Toshiaki Maruyama, La Jolla, CA (US); Shumpei Maruyama, San Francisco, CA (US); Shigeru CJ Okumura, San Diego, CA (US)

(73) Assignee: ABWIZ BIO, INC, San Diego, CA (US)

( * ) Notice: Subject to any disclaimer, the term of this patent is extended or adjusted under 35 U.S.C. 154(b) by 0 days.

(21) Appl. No.: 14/092,645

(22) Filed: Nov. 27, 2013

(65) Prior Publication Data
US 2014/0162321 A1 Jun. 12, 2014

Related U.S. Application Data

(60) Provisional application No. 61/730,879, filed on Nov. 28, 2012.

(51) Int. Cl.
*C12Q 1/68* (2006.01)
(52) U.S. Cl.
CPC .................. *C12Q 1/6811* (2013.01)
(58) Field of Classification Search
None
See application file for complete search history.

(56) References Cited

U.S. PATENT DOCUMENTS

| | | | |
|---|---|---|---|
| 4,356,270 | A | 10/1982 | Itakura |
| 4,937,190 | A | 6/1990 | Palmenberg et al. |
| 5,130,238 | A | 7/1992 | Malek et al. |
| 5,464,758 | A | 11/1995 | Gossen et al. |
| 5,508,178 | A | 4/1996 | Rose et al. |
| 5,576,195 | A | 11/1996 | Robinson et al. |
| 5,595,891 | A | 1/1997 | Rose et al. |
| 5,679,512 | A | 10/1997 | Laney et al. |
| 5,683,879 | A | 11/1997 | Laney et al. |
| 5,744,308 | A | 4/1998 | Guillou-bonnici et al. |
| 5,770,428 | A | 6/1998 | Boris-lawrie et al. |
| 5,814,618 | A | 9/1998 | Bujard et al. |
| 5,846,818 | A | 12/1998 | Robinson et al. |

(Continued)

FOREIGN PATENT DOCUMENTS

| | | |
|---|---|---|
| EP | 2925878 A1 | 10/2015 |
| WO | WO1999/002727 | 1/1999 |

(Continued)

OTHER PUBLICATIONS

Maniatis et al. "Molecular Cloning", (1982), Cold Spring Harbor Laboratory, Box 100, Cold Spring Harbor, New York, New York, pp. 213-216.*

(Continued)

*Primary Examiner* — Stephanie K Mummert
(74) *Attorney, Agent, or Firm* — Wilson Sonsini Goodrich & Rosati

(57) ABSTRACT

This disclosure relates to methods for creating engineered templates that are useful for amplification of one or more antibody genes without the use of gene-specific primers. More specifically, templates engineered using these methods in a polymerase chain reaction setting which allows for the specific amplification of one or more antibody genes.

26 Claims, 13 Drawing Sheets

(56) References Cited

U.S. PATENT DOCUMENTS

| | | | |
|---|---|---|---|
| 5,885,827 A | 3/1999 | Walb et al. | |
| 5,962,272 A | 10/1999 | Chenchik et al. | |
| 6,074,818 A | 6/2000 | Caetano-Anolles et al. | |
| 6,251,639 B1 | 6/2001 | Kurn | |
| 6,498,025 B1 | 12/2002 | Miller | |
| 6,680,209 B1 | 1/2004 | Buechler et al. | |
| 6,794,132 B2 | 9/2004 | Buechler et al. | |
| 6,803,230 B2 | 10/2004 | Bowdish et al. | |
| 6,919,189 B2 | 7/2005 | Bowdish et al. | |
| 7,112,715 B2 | 9/2006 | Chambon et al. | |
| 7,306,906 B2 * | 12/2007 | Maruyama | C12N 15/1093 435/6.12 |
| 7,414,111 B2 * | 8/2008 | Maruyama | C07K 16/005 530/387.1 |
| 7,435,412 B2 | 10/2008 | Bowdish et al. | |
| 8,828,688 B2 * | 9/2014 | Namsaraev | C12Q 1/6816 435/91.2 |
| 2002/0168676 A1 | 11/2002 | Notomi et al. | |
| 2003/0165911 A1 | 9/2003 | Ness et al. | |
| 2003/0219839 A1 | 11/2003 | Bowdish et al. | |
| 2004/0038253 A1 | 2/2004 | Nagamine | |
| 2004/0101886 A1 | 5/2004 | Bowdish et al. | |
| 2006/0094052 A1 | 5/2006 | Kelman et al. | |
| 2006/0204973 A1 | 9/2006 | Hirano | |
| 2008/0293589 A1 | 11/2008 | Shapero | |
| 2009/0311790 A1 * | 12/2009 | Ogawa et al. | 435/455 |

FOREIGN PATENT DOCUMENTS

| | | |
|---|---|---|
| WO | WO2008/156536 | 12/2008 |
| WO | WO2014/085687 | 6/2014 |
| WO | WO2014/186193 | 11/2014 |

OTHER PUBLICATIONS

Little et al. (J of Immunol Methods, 1999, vol. 231, p. 3-9).*

Tang et al. (Nature Methods, 2009, 6(5):377-384).*

69864 pET-28a(+) DNA Novagen product description, 2013.

Bird et al., "Single-chain antigen-binding proteins." Science, Oct. 21, 1988, vol. 242 Issue No. 4877, pp. 423-426.

Brown et al. "Chemical synthesis and cloning of a tyrosine tRNA gene." Methods in Enzymology, vol. 68, 1979, pp. 109-151.

Conose et al., "Gene Therapy Progress and Prospects: Episomally maintained self-replicating systems." Gene Therapy, 2004, vol. 11, pp. 1735-1741.

Doherty et al., "Bacteriophage T7 DNA Ligase: Overexpression, Purification, Crystallization, and Characterization." Journal of Biological Chemistry, vol. 271, No. 19, May 10, 1996, pp. 11083-11089.

Fuhrmann-Benzakein et al., "Inducible and irreversible control of gene expression using a single transgene." Nucleic Acids Research, Dec. 2000, vol. 28, Issue No. 23, p. e99.

Holliger et al., "Engineered antibody fragments and the rise of single domains." Nature Biotechnology, 2005, vol. 23, Issue 9, pp. 1126-1136.

Huston et al., "Protein engineering of antibody binding sites: recovery of specific activity in an anti-digoxin single-chain Fv analogue produced in *Escherichia coli*." Proc. Natl. Acad. Sci. USA, 1988, vol. 85, pp. 5879-5883.

Indra et al. "Temporally-controlled site-specific mutagenesis in the basal layer of the epidermis: comparison of the recombinase activity of the tamoxifen-inducible Cre-ERT and Cre-ERT2 recombinases." Nucl. Acids Res., 1999, 27 (22): 4324-4327.

Jäck et al., "Looping out and deletion mechanism for the immunoglobulin heavy-chain class switch." Proc. Natl. Acad. Sci. USA, Mar. 1988, vol. 85, No. 5, pp. 1581-1585.

Kitts et al., "A method for producing recombinant baculovirus expression vectors at high frequency." Biotechniques. May 1993, vol. 14, Issue No. 5, pp. 810-817.

Kramer & Fussenegger, Transgene control engineering in mammalian cells. In: Methods in Molecular Biology, vol. 308:123-144 (2005).

Luckow, V A. "Baculovirus systems for the expression of human gene products." Curr. Opin. Biotechnol., 1993, vol. 4, pp. 564-572.

Luckow et al., "Efficient generation of infectious recombinant baculoviruses by site-specific transposon-mediated insertion of foreign genes into a baculovirus genome propagated in *Escherichia coli*." J Virol., Aug. 1993, vol. 67, Issue No. 8, pp. 4566-4579.

Lowman and Wells, "Monovalent phage display: A method for selecting variant proteins from random libraries." Methods: A Companion to Methods in Enzymology, vol. 3, Issue 3, Dec. 1991, pp. 205-216.

Narang et al., "Improved phosphotriester method for the synthesis of gene fragments." Methods in Enzymology, vol. 68, 1979, pp. 90-98.

No et al., "Ecdysone-inducible gene expression in mammalian cells and transgenic mice." Proc. Natl. Acad. Sci. USA, vol. 93, Issue 8, pp. 3346-3351, Apr. 1996.

Nussinov R., "Eukaryotic dinucleotide preference rules and their implications for degenerate codon usage." J Mol Biol., 1981, vol. 149, Issue 1, pp. 125-31.

Osbourn et al., "Directed selection of MIP-1α neutralizing CCR5 antibodies from a phage display human antibody library." Nature Biotechnology, 1998, vol. 16, pp. 778-781.

PCT/US2013/72376 International Search Report and Written Opinion dated Feb. 14, 2014.

Pluckthun, "*Antibodies from Exchericia coli*." In: The Pharmacology of Monoclonal Antibodies, vol. 113, Rosenburg and Moore Eds. Springer-Verlag, New York, pp. 269-315 (1994).

SuperScript III Reverse Transcriptase product description, 2004.

Urlaub et al., "Isolation of Chinese hamster cell mutants deficient in dihydrofolate reductase activity." Proc. Natl. Acad. Sci. USA, Jul. 1980, vol. 77, Issue No. 07, pp. 4216-4220.

Ward et al., "Binding activities of a repertoire of single immunoglobulin variable domains secreted from *Escherichia coli*." Nature, vol. 341, Oct. 1989, pp. 544-546.

Wells and Lowman, "Rapid evolution of peptide and protein binding properties in vitro." Current Opinion in Biotechnology, vol. 3, Issue 4, Aug. 1992, pp. 355-362.

Co-pending U.S. Appl. No. 14/783,258, filed Oct. 8, 2015.

PCT Patent Application No. PCT/US2013/072376 International Preliminary Report on Patentability dated Jun. 11, 2015.

\* cited by examiner

SEQUENCE LISTING

<160> NUMBER OF SEQ ID NOS: 70

<210> SEQ ID NO 1
<211> LENGTH: 20

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tttttttttt tttttttttt                                              20

<210> SEQ ID NO 2
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ctctctccat cttcccacca tccagtgagc agttgacatc cggacactcc tcttggtagc    60
cggtcgtc                                                            68

<210> SEQ ID NO 3
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ccctggatct gctgcccaaa ctaactccat ggtcactcct cttccaacgg ccacgtc       57

<210> SEQ ID NO 4
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gacgaccggc taccaagagg agtgtccgga tgtc                               34

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gacgtggccg ttggaagagg agtg                                          24

<210> SEQ ID NO 6
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gacgaccggc taccaagagg agtgtctaga gacattgtga tgwcacagtc tc            52

<210> SEQ ID NO 7
```

<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
gacgaccggc taccaagagg agtgtctaga gatgttktga tgacccarac tc          52

<210> SEQ ID NO 8
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
gacgaccggc taccaagagg agtgtctaga gacattgtga tgackcaggc tg          52

<210> SEQ ID NO 9
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
gacgaccggc taccaagagg agtgtctaga gacawtgtgc tgacccartc tc          52

<210> SEQ ID NO 10
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gacgaccggc taccaagagg agtgtctaga gaaawtgtgc tcacccagtc tc          52

<210> SEQ ID NO 11
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gacgaccggc taccaagagg agtgtctaga gacatccaga tgacmcagtc tc          52

<210> SEQ ID NO 12
<211> LENGTH: 53
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
gacgaccggc taccaagagg agtgtctaga gatatccaga tgacacagac tac         53

<210> SEQ ID NO 13
<211> LENGTH: 50

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gacgaccggc taccaagagg agtgtctaga gacattgtsa tgacccagtc                50

<210> SEQ ID NO 14
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gacgaccggc taccaagagg agtgtctaga caaattgttc tcacccagtc tc             52

<210> SEQ ID NO 15
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gacgaccggc taccaagagg agtgtctaga gacatcktgc tsactcagtc tc             52

<210> SEQ ID NO 16
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gacgaccggc taccaagagg agtgtctaga gatattgtga taacccagga tg             52

<210> SEQ ID NO 17
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gacgaccggc taccaagagg agtgtctaga agyattgtga tgacccagwc tc             52

<210> SEQ ID NO 18
<211> LENGTH: 53
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gacgaccggc taccaagagg agtgtctaga gacatccaga tgacacaatc ttc            53

<210> SEQ ID NO 19
<211> LENGTH: 47
<212> TYPE: DNA

<213> ORGANISM: Artificial Sequence
<220> FEATURE:
<223> OTHER INFORMATION: Description of Artificial Sequence: Synthetic primer

<400> SEQUENCE: 19
gacgtggccg ttggaagagg agtgctcgag gtgcagcttc agsagtc        47

<210> SEQ ID NO 20
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
gacgtggccg ttggaagagg agtgctcgag gtgcagctga agsagtc        47

<210> SEQ ID NO 21
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gacgtggccg ttggaagagg agtgctcgag gtccagctgc aacagtttg      49

<210> SEQ ID NO 22
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gacgtggccg ttggaagagg agtgctcgag gtycagctgc arcartc        47

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
gacgtggccg ttggaagagg agtgctcgag gtccaactgc agcagyc        47

<210> SEQ ID NO 24
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
gacgtggccg ttggaagagg agtgctcgag gttcagctgc agcagtc        47

<210> SEQ ID NO 25
<211> LENGTH: 47
<212> TYPE: DNA
<213> ORGANISM: Artificial Sequence -continued
<220> FEATURE:
<223> OTHER INFORMATION: Description of Artificial Sequence: Synthetic
      primer

<400> SEQUENCE: 25
gacgtggccg ttggaagagg agtgctcgag gtgaagctgg tggagwc                47

<210> SEQ ID NO 26
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gacgtggccg ttggaagagg agtgctcgag gtgaagcttc tggagtc                47

<210> SEQ ID NO 27
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gacgtggccg ttggaagagg agtgctcgag gtgmagctgg tggagtc                47

<210> SEQ ID NO 28
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gacgtggccg ttggaagagg agtgctcgag gtgaagcttc tggagtctgg             50

<210> SEQ ID NO 29
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gacgtggccg ttggaagagg agtgctcgag gtgaagcttg aggagtc                47

<210> SEQ ID NO 30
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gacgtggccg ttggaagagg agtgctcgag gttactctga aagagtc                47

<210> SEQ ID NO 31
<211> LENGTH: 47
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 31
gacgtggccg ttggaagagg agtgctcgag atccagttgg tgcagtc                47

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gacgtggccg ttggaagagg agtg                                         24

<210> SEQ ID NO 33
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gacgaccggc taccaagagg agtg                                         24

<210> SEQ ID NO 34
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Free cysteine
<220> FEATURE:
<221> NAME/KEY: MOD_RES
<222> LOCATION: (7)..(7)
<223> OTHER INFORMATION: phosphorylated Thr
<220> FEATURE:
<221> NAME/KEY: MOD_RES
<222> LOCATION: (9)..(9)
<223> OTHER INFORMATION: phosphorylated Tyr

<400> SEQUENCE: 34

Cys His Thr Gly Phe Leu Thr Glu Tyr Val Ala Thr Arg Trp
1               5                   10

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(1)
<223> OTHER INFORMATION: Free cysteine
<220> FEATURE:
<221> NAME/KEY: MOD_RES
<222> LOCATION: (12)..(12)
<223> OTHER INFORMATION: phosphorylated Thr
<220> FEATURE:
<221> NAME/KEY: MOD_RES
<222> LOCATION: (14)..(14)
<223> OTHER INFORMATION: phosphorylated Tyr

<400> SEQUENCE: 35

Cys Asp Pro Glu His Asp His Thr Gly Phe Leu Thr Glu Tyr Val Ala
1               5                   10                  15

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

His Thr Gly Phe Leu Thr Glu Tyr Val Ala Thr Arg Trp
1               5                   10

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Asp Pro Glu His Asp His Thr Gly Phe Leu Thr Glu Tyr Val Ala
1               5                   10                  15

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
tacctacarc ctsagcagya ctctg                                        25

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
cctcccsgag ccagtgaccg tgacttg                                      27

<210> SEQ ID NO 40
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
cgcagaattc tgcagattgt acctacaacc tcacgtcgac cactcctctt ggtagccggt    60
cgtc                                                               64

<210> SEQ ID NO 41
<211> LENGTH: 64
<212> TYPE: DNA

<213> ORGANISM: Artificial Sequence
<220> FEATURE:
<223> OTHER INFORMATION: Description of Artificial Sequence: Synthetic
      oligonucleotide

<400> SEQUENCE: 41
crcagaattc tgatgattgt acctacaacc tcacgtcgac cactcctctt ggtagccggt    60
cgtc    64

<210> SEQ ID NO 42
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cgcagagccc cgaagactgt acctacaacc tcacgtcgac cactcctctt ggtagccggt    60
cgtc    64

<210> SEQ ID NO 43
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cgcaggatcc tacatattgt acctacaacc tcacgtcgac cactcctctt ggtagccggt    60
cgtc    64

<210> SEQ ID NO 44
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cgcagagccc ygaagacaat acctacagcc tcacgtcgac cactcctctt ggtagccggt    60
cgtc    64

<210> SEQ ID NO 45
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
gacgaccggc taccaagagg agtggtcgac g    31

<210> SEQ ID NO 46
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gctgcttggt caaaggctac ctccccgaac cggtcactcc tcttccaacg gccacgtc    58

<210> SEQ ID NO 47
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gctgcctggt caaaggctac ctcccggaac cggtcactcc tcttccaacg gccacgtc    58

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
gacgtggccg ttggaagagg agtgaccggt                                    30

<210> SEQ ID NO 49
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gacgaccggc taccaagagg agtgtctaga gacattgtgc tgacccag                48

<210> SEQ ID NO 50
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gacgaccggc taccaagagg agtgtctaga gaccctrtgm tgacccag                48

<210> SEQ ID NO 51
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gacgaccggc taccaagagg agtgtctaga gatgkygtga tgacccag                48

<210> SEQ ID NO 52
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gacgaccggc taccaagagg agtgtctaga gcagccgtgm tgacccag            48

<210> SEQ ID NO 53
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gacgaccggc taccaagagg agtgtctaga gccatcraaa tgacccag            48

<210> SEQ ID NO 54
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gacgaccggc taccaagagg agtgtctaga gcycaagkgm tgacccag            48

<210> SEQ ID NO 55
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gacgaccggc taccaagagg agtgtctaga gcsctsgtgm tgacccag            48

<210> SEQ ID NO 56
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
gacgaccggc taccaagagg agtgtctaga tatgtcatga tgacccag            48

<210> SEQ ID NO 57
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gacgtggccg ttggaagagg agtgctcgag caggagcagc tgaaggagtc          50

<210> SEQ ID NO 58
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gacgtggccg ttggaagagg agtgctcgag cagtcagtga aggagtccga          50

<210> SEQ ID NO 59
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gacgtggccg ttggaagagg agtgctcgag cagtcgctgg rggagtccrg          50

<210> SEQ ID NO 60
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gacgtggccg ttggaagagg agtgctcgag cagtcgytgg gggagtccrg          50

<210> SEQ ID NO 61
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gacgtggccg ttggaagagg agtgctcgag cagtcgktgg aggagtccrg          50

<210> SEQ ID NO 62
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gacgtggccg ttggaagagg agtgctcgag cagtcggtgg aggagtccrg          50

<210> SEQ ID NO 63
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gacgtggccg ttggaagagg agtgctcgag cagwcrgtga aggagtccga          50

<210> SEQ ID NO 64
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gacgtggccg ttggaagagg agtgctcgag cagtcgctgg aggaattcgg          50

```
<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
cagtgagcag ttaacatctg gagg                                              24

<210> SEQ ID NO 66
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
ctaactccat ggtgaccctg ggatg                                             25

<210> SEQ ID NO 67
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
gtacctacaa cctcagcagy actctg                                            26

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
acctacagcc tgagcagcac tctg                                              24

<210> SEQ ID NO 69
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
aggctacctc cccgagccag tgaccg                                            26

<210> SEQ ID NO 70
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
gctacctccc ggagccagtg accgtg                                            26
```

PREPARATION OF GENE-SPECIFIC TEMPLATES FOR THE USE IN SINGLE PRIMER AMPLIFICATION

CROSS-REFERENCE

This application claims the benefit of U.S. Provisional Application No. 61/730,879, filed Nov. 28, 2012, which application is incorporated herein by reference.

BACKGROUND OF THE INVENTION

Methods for nucleic acid amplification and detection of amplification products may be used to detect, identify, quantify and analyze nucleic acid sequences. Nucleic acid amplification is an important step in the construction of libraries from related genes such as antibodies.

These libraries can be screened for antibodies having specific desirable activities. Nucleic acid analysis is important for a variety of purposes such as, for example, detection and identification of pathogens, detection of gene alteration leading to defined phenotypes, diagnosis of genetic diseases or the susceptibility to a disease, assessment of gene expression in development, and in response to defined stimuli, as well as the various genome projects. Other applications of nucleic acid amplification methods include the detection of rare cells, detection of pathogens, detection of altered gene expression in malignancy, etc.

Amplification methods that employ a single primer are disclosed in U.S. Pat. Nos. 5,508,178; 5,595,891; 5,683,879; 5,130,238; and 5,679,512. In U.S. Pat. No. 5,744,308, the primer is a DNA/RNA chimeric primer. Alternative amplification methods that employ template switching oligonucleotides (TSOs) and blocking oligonucleotides are disclosed in U.S. Pat. Nos. 5,679,512; 5,962,272; and 6,251,639. In some of these amplification methods, the TSO amplification method utilizes chimeric DNA primer.

Nucleic acid amplification is also useful for qualitative analysis (such as, for example, the detection of the presence of defined nucleic acid sequences) and quantification of defined gene sequences (useful, for example, in assessment of the amount of pathogenic sequences as well as the determination of gene multiplication or deletion and cell transformation from normal to malignant cell type). The detection of sequence alterations in a nucleic acid sequence is important for the detection of mutant genotypes, as relevant for genetic analysis, the detection of mutations leading to drug resistance, pharmacogenomics, etc.

There are many variations of nucleic acid amplification: for example, exponential amplification, linked linear amplification, ligation-based amplification, and transcription-based amplification. One example of exponential nucleic acid amplification method is polymerase chain reaction (PCR), which has been disclosed in numerous publications. Indeed, PCR is the most commonly used target amplification method. PCR is based on multiple cycles of denaturation, hybridization of two different oligonucleotide primers, each to opposite strand of the target strands, and primer extension by a nucleotide polymerase to produce multiple double stranded copies of the target sequence.

Traditional DNA amplification requires two gene-specific primers for PCR. As each primer has its own optimal annealing temperature, it is not easy to amplify a particular gene specifically and with good efficiency. This is especially a concern for amplification of antibody genes. In these methods, the forward primers tend to anneal to the framework 1 region of the antibody genes where some somatic mutations and variations may necessitate the use of lower annealing temperatures to allow some ambiguities. However, this is not optimum for the reverse primers where they usually anneal to the constant region of the antibody genes and leads to non-specific amplification of other genes. These factors considerably lower the specificity of the amplified genes and covered repertoires after the amplification and result in an overall skewed diversity and loss of rare but important genes.

SUMMARY OF THE INVENTION

The target amplification methods presently known and used have several drawbacks. For example, the transcription base amplification methods, such as Nucleic Acid Sequence Based Amplification (NASBA) and transcription mediated amplification (TMA), are limited by the need for incorporation of the polymerase promoter sequence into the amplification product by a primer: a process that is prone to result in non-specific amplification.

Therefore, there is a need for improved nucleic acid amplification methods that overcome these drawbacks. The methods provided herein fulfill this need and provide additional benefits.

This disclosure relates to methods for creating engineered templates useful for amplification of genes without the use of gene-specific primers. More specifically, templates engineered using these methods allow for the specific amplification of antibody genes in a PCR setting without the use of gene-specific primers.

In addition, the methods provided herein describe the generation of engineered nucleic acid templates using nick ligation and polymerase extension. In some cases, the methods provided herein include the addition of a predetermined sequence to a polynucleotide using nick ligation as an intermediate step of the method to generate an engineered template. In some cases, prior to the step of nick ligation, a polynucleotide is contacted with an oligonucleotide which contains at least a sequence that is reverse complementary to a native restriction endonuclease recognition sequence located within the polynucleotide. For example, after annealing the oligonucleotide to the polynucleotide, a restriction endonuclease may cut the oligonucleotide and the polynucleotide at the restriction endonuclease recognition sequence. In some cases, after restriction digestion, a nick ligation reaction may be performed to add the predetermined sequence to the polynucleotide.

The methods provided herein permit the use of any restriction endonuclease with a native restriction endonuclease restriction site located within the polynucleotide ahead of nick ligation. For example, unlike methods known in the art which require use of a specific set of restriction endonucleases and restriction endonuclease recognition sequences in order to add a predetermined sequence to a polynucleotide, the advantage of nick ligation does not restrict the method to use of a set of restriction endonucleases.

Described herein in various embodiments are methods for creating an engineered template comprising the steps of annealing an oligonucleotide to a complementary portion of a polynucleotide, either the first strand cDNA or the second strand cDNA, wherein the oligonucleotide has a predetermined sequence that anneals to the second oligonucleotide and the annealed polynucleotide and the second oligonucleotide are ligated in the presence of DNA ligase.

This disclosure also provides methods for creating an engineered template comprising a polynucleotide with at least a cleavage site, a first portion and a second portion, the method comprising: (a) creating a double-stranded portion of the polynucleotide at the cleavage site; (b) cleaving the double-stranded portion of the polynucleotide at the cleavage site; (c) annealing a first portion of a first oligonucleotide to the first portion of the polynucleotide and a second portion of the first oligonucleotide to a first portion of a second oligonucleotide, the second oligonucleotide containing a first pre-determined sequence; (d) ligating the first portion of the polynucleotide to the second portion of the second oligonucleotide to create a pre-engineered template with the first pre-determined sequence; (e) annealing a set of primers to the pre-engineered template, at least one primer of the set of the primers having a portion containing a second pre-determined sequence substantially complementary to the first portion of the polynucleotide within the pre-engineered template of step (d); and, (f) synthesizing the engineered template such that the engineered template contains the first pre-determined sequence at one end and the second pre-determined sequence at a different end.

This disclosure also provides methods of creating an engineered template for single primer amplification, the method comprising: (a) annealing an oligonucleotide containing a restriction site to a polynucleotide to create a polynucleotide with a double-stranded portion containing the restriction site; (b) cleaving the double-stranded portion of the polynucleotide at the restriction site using a restriction endonuclease; (c) removing fragments of the oligonucleotide of step (a) from the polynucleotide such that the cleaved polynucleotide does not contain any double-stranded portions thereby creating a polynucleotide with a cleavage at the 5' end; (d) annealing a first adaptor oligonucleotide to the 5' end of the cleaved polynucleotide of step (c), the first adaptor oligonucleotide having a first portion that anneals to the 5' end of the cleaved polynucleotide and a second portion that anneals to a second adaptor oligonucleotide, the second adaptor oligonucleotide containing a first pre-determined sequence; (d) ligating the 5' end of the cleaved polynucleotide to the second adaptor oligonucleotide thereby creating a pre-engineered template having the first pre-determined sequence at, or near, the 5' end; (e) removing the first adaptor oligonucleotide from the pre-engineered template; (f) annealing a set of primers to the pre-engineered template, at least one primer of the set of the primers having a portion containing a second pre-determined sequence; and (g) synthesizing an engineered template such that the engineered template has the first pre-determined sequence at or near the 5' end and the second pre-determined sequence at, or near, the 3' end.

This disclosure also provides methods of creating an engineered template for single primer amplification, the method comprising: (a) annealing an oligonucleotide containing a restriction site to a polynucleotide to create a polynucleotide with a double-stranded portion containing the restriction site; (b) cleaving the double-stranded portion of the polynucleotide at the restriction site using a restriction endonuclease; (c) removing fragments of the oligonucleotide of step (a) from the polynucleotide such that the cleaved polynucleotide does not contain any double-stranded portions thereby creating a polynucleotide with a cleavage at the 5' end; (d) annealing a first adaptor oligonucleotide to the 5' end of the cleaved polynucleotide of step (c), and a second adapter oligonucleotide to a third adaptor oligonucleotide, the second adaptor oligonucleotide substantially complementary to the third adaptor oligonucleotide, the third adaptor oligonucleotide containing a first pre-determined sequence; (e) ligating the 5' end of the cleaved polynucleotide to the third adaptor oligonucleotide thereby creating a pre-engineered template having the first pre-determined sequence at, or near, the 5' end; (f) removing the first adaptor oligonucleotide from the pre-engineered template; (g) annealing a set of primers to the pre-engineered template, at least one primer of the set of the primers having a second pre-determined sequence; and (h) synthesizing the engineered template such that the engineered template has the first pre-determined sequence at, or near, the 5' end and the second pre-determined sequence at, or near, the 3' end.

This disclosure provides methods of creating an engineered template for single primer amplification, the method comprising: (a) annealing an oligonucleotide containing a restriction site to a polynucleotide to create a polynucleotide with a double-stranded portion containing the restriction site; (b) cleaving the double-stranded portion of the polynucleotide at the restriction site using a restriction endonuclease; (c) removing fragments of the oligonucleotide of step (a) from the polynucleotide such that the cleaved polynucleotide does not contain any double-stranded portions thereby creating a polynucleotide with a cleavage at the 5' end; (d) annealing a first portion of a primer to the cleaved polynucleotide of step (c), the primer containing a second portion with a first pre-determined sequence; (e) synthesizing a second polynucleotide having the first pre-determined sequence at, or near, a 5' end and a 3' end that contains the cleavage of step (c); (f) annealing a first adaptor oligonucleotide to the to the 3' end of the second polynucleotide of step (e), the first adaptor oligonucleotide having a first portion that anneals to the 3' end of the second polynucleotide and a second portion that anneals to a second adaptor oligonucleotide, the second adaptor oligonucleotide containing a second pre-determined sequence, (g) ligating the 3' end of the second polynucleotide to the second adaptor oligonucleotide thereby creating a pre-engineered template with the second pre-determined sequence at, or near, the 3' end; and (h) removing the first adaptor oligonucleotide from the second polynucleotide to create an engineered template that has the first pre-determined sequence at, or near, the 5' end and the second pre-determined sequence at, or near, the 3' end.

This disclosure also provides methods of creating an engineered template for single primer amplification, the method comprising: (a) annealing an oligonucleotide containing a restriction site to a polynucleotide to create a polynucleotide with a double-stranded portion containing the restriction site; (b) cleaving the double-stranded portion of the polynucleotide at the restriction site using a restriction endonuclease; (c) removing fragments of the oligonucleotide of step (a) from the polynucleotide such that the cleaved polynucleotide does not contain any double-stranded portions thereby creating a polynucleotide with a cleavage at the 5' end; (d) annealing a first portion of a primer to the cleaved polynucleotide of step (c), the primer containing a second portion with a first pre-determined sequence; (e) synthesizing a second polynucleotide having the first pre-determined sequence at, or near, a 5' end and a 3' end that contains the cleavage of step (c); (f) annealing a first adaptor oligonucleotide to the 3' end of the second polynucleotide of step (e), and a second adapter oligonucleotide to a third adaptor oligonucleotide, the second adaptor oligonucleotide substantially complementary to the third adaptor oligonucleotide, the third adaptor oligonucleotide containing a second pre-determined sequence; (g) ligating the 3' end of the second polynucleotide to the third adaptor oligonucleotide thereby creating a pre-engineered template with the second pre-determined sequence at, or near, the 3' end; and (h) removing the first adaptor oligonucleotide from the second polynucleotide to create an engineered template that has the first pre-determined sequence at, or near, the 5' end and the second pre-determined sequence at, or near, the 3' end.

This disclosure also provides methods of creating an engineered template for single primer amplification, the method comprising: (a) annealing a set of primers to a first polynucleotide, the primers containing a first pre-determined sequence; (b) synthesizing a second polynucleotide having the first pre-determined sequence at, or near, the 5' end; (c) annealing an oligonucleotide containing a restriction site to the second polynucleotide to create a second polynucleotide with at least a double-stranded portion, the double-stranded portion containing the restriction site; (d) cleaving the double-stranded portion of the second polynucleotide at the restriction site using a restriction endonuclease; (e) removing fragments of the oligonucleotide of step (c) from the second polynucleotide such that the cleaved polynucleotide does not contain any double-stranded portions thereby creating a second polynucleotide with a cleavage at the 3' end; (f) annealing a first adaptor oligonucleotide to the to the 3' end of the second polynucleotide of step (e), the first adaptor oligonucleotide having a first portion that anneals to the 3' end of the second polynucleotide and a second portion that anneals to a second adaptor oligonucleotide, the second adaptor oligonucleotide containing a second pre-determined sequence, (g) ligating the 3' end of the cleaved polynucleotide to the second adaptor oligonucleotide thereby creating a pre-engineered template with the second pre-determined sequence at, or near, the 3' end; and (h) removing the first adaptor oligonucleotide from the second polynucleotide to create an engineered template that has the first pre-determined sequence at, or near, the 5' end and the second pre-determined sequence at, or near, the 3' end.

In some other embodiments, this disclosure provides methods of creating an engineered template for single primer amplification, the method comprising: (a) annealing a set of primers to a first polynucleotide, the primers containing a first pre-determined sequence; (b) synthesizing a second polynucleotide having the first pre-determined sequence at, or near, the 5' end; (c) annealing an oligonucleotide containing a restriction site to the second polynucleotide to create a second polynucleotide with at least a double-stranded portion, the double-stranded portion containing the restriction site; (d) cleaving the double-stranded portion of the second polynucleotide at the restriction site using a restriction endonuclease; (e) removing fragments of the oligonucleotide of step (c) from the second polynucleotide such that the cleaved polynucleotide does not contain any double-stranded portions thereby creating a second polynucleotide with a cleavage at the 3' end; (f) annealing a first adaptor oligonucleotide to the 3' end of the second polynucleotide of step (e), and a second adapter oligonucleotide to a third adaptor oligonucleotide, the second adaptor oligonucleotide substantially complementary to the third adaptor oligonucleotide, the third adaptor oligonucleotide containing a second pre-determined sequence; (g) ligating the 3' end of the second polynucleotide to the second adaptor oligonucleotide to create a pre-engineered template with the second pre-determined sequence at, or near, the 3' end; and (h) removing the first adaptor oligonucleotide from the second polynucleotide to create an engineered template that has the first pre-determined sequence at, or near, the 5' end and the second pre-determined sequence at, or near, the 3' end.

Other features and advantages of the present invention will become more readily apparent to those of ordinary skill in the art after reviewing the following detailed description and accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

The instant application contains a Sequence Listing which has been submitted electronically in ASCII format and is hereby incorporated by reference in its entirety. Said ASCII copy, created on Nov. 26, 2013, is named 44712-704.201_SL.txt and is 17,394 bytes in size.

BRIEF DESCRIPTION OF THE DRAWINGS

The details of the present invention, both as to its structure and operation, may be gleaned in part by study of the accompanying drawings, in which like reference numerals refer to like parts, and in which.

DETAILED DESCRIPTION OF THE INVENTION

Figure 1A:
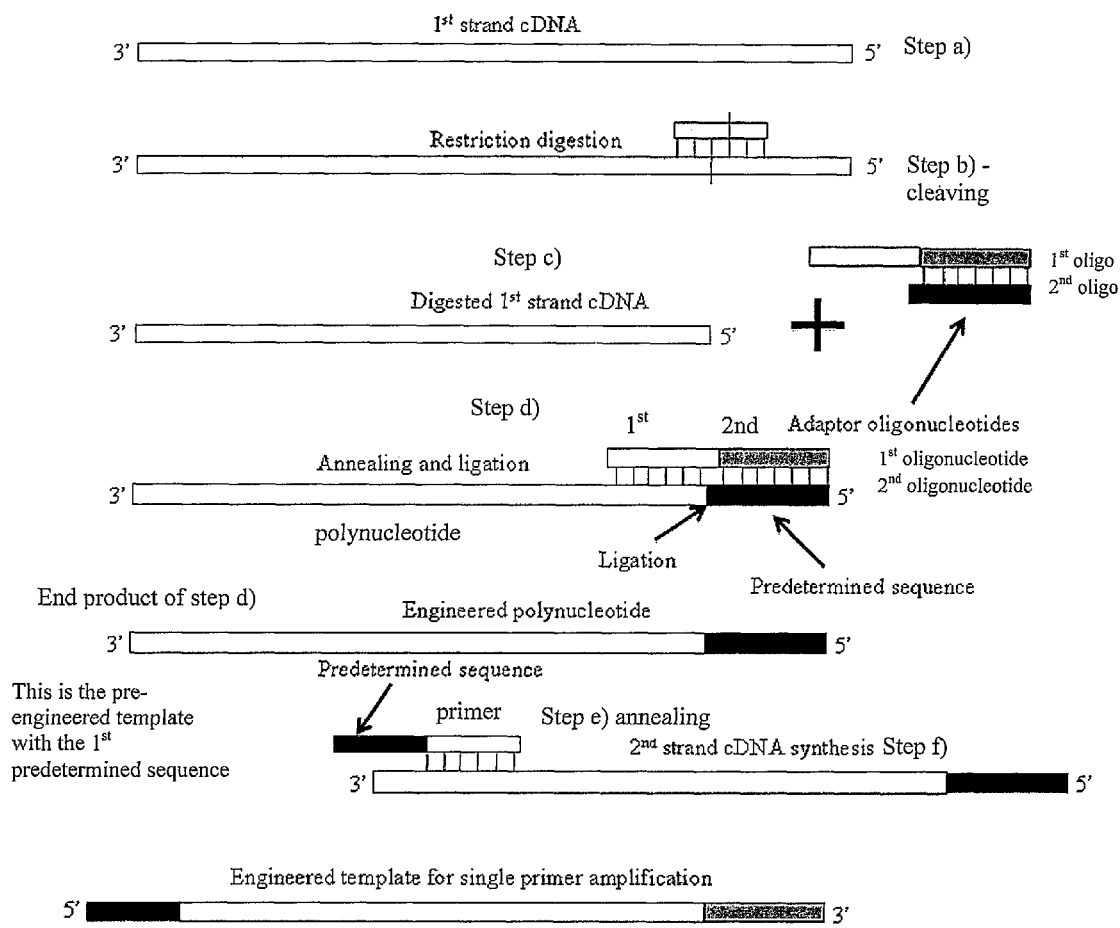
FIG. 1A is an exemplary embodiment of the invention where an engineered template for single primer amplification is created by at least attaching at least one pre-determined sequence to a first strand cDNA.

The use of the terms "a" and "an" and "the" and similar referents in the context of describing the disclosed embodiments (especially in the context of the following claims) are to be construed to cover both the singular and the plural, unless otherwise indicated herein or clearly contradicted by context.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

As used herein, "pg" means picogram, "ng" means nanogram, "ug" or "μg" mean microgram, "mg" means milligram, "ul" or "μl" mean microliter, "ml" means milliliter, "l" means liter, "kb" means kilobases, "uM" or "μM" means micromolar, "nM" means nanomolar, "pM" means picomolar, "fM" means femtomolar.

The term "isolated" refers to the state in which specific proteins or nucleic acids encoding the proteins will be, in accordance with the present invention. Proteins and nucleic acids encoding them will be free or substantially free of material with which they are naturally associated such as other polypeptides or nucleic acids with which they are found in their natural environment, or the environment in which they are prepared (e.g., cell culture) when such preparation is by recombinant DNA technology.

The terms "comprising," "having," "including," and "containing" are to be construed as open-ended terms (i.e., meaning "including, but not limited to,") unless otherwise noted.

The terms "connected" and "ligated" are to be construed as partly or wholly contained within, attached to, or joined together, even if there is something intervening. All methods described herein can be performed in any suitable order unless otherwise indicated herein or otherwise clearly contradicted by context.

The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

The term "nucleotide" as used herein refers to a monomeric unit of a polynucleotide that consists of a heterocyclic base, a sugar, and one or more phosphate groups. The naturally occurring bases, (guanine, (G), adenine, (A), cytosine, (C), thymine, (T), and uracil (U)) are typically derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleic acids are typically linked via phosphate bonds to form nucleic acids, or polynucleotides though many other linkages are known in the art (such as, though not limited to phosphorothioates, boranophosphates and the like).

The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to methylated and/or capped polynucleotides.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the non transcribed strand of DNA (i.e., the strand having a sequence homologous to the mRNA).

A DNA "coding sequence" or "coding region" is a double-stranded DNA sequence which is transcribed and translated into a polypeptide in vivo when placed under the control of appropriate expression control sequences. The boundaries of the coding sequence (the "open reading frame" or "ORF") are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence will usually be located 3' to the coding sequence. The term "non-coding sequence" or "non-coding region" refers to regions of a polynucleotide sequence that not translated into amino acids (e.g., 5' and 3' untranslated regions).

The term "reading frame" refers to one of the six possible reading frames, three in each direction, of the double stranded DNA molecule. The reading frame that is used determines which codons are used to encode amino acids within the coding sequence of a DNA molecule.

As used herein, an "antisense" nucleic acid molecule comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid molecule can hydrogen bond to a sense nucleic acid molecule.

The terms "base pair" or ("bp") refer to a partnership of adenine (A) with thymine (T), or of cytosine (C) with guanine (G) in a double stranded DNA molecule. In RNA, uracil (U) is substituted for thymine.

As used herein, a "codon" refers to the three nucleotides which, when transcribed and translated, encode a single amino acid residue; or in the case of UUA, UGA or UAG encode a termination signal. Codons encoding amino acids are well known in the art.

Optimal codon usage is indicated by codon usage frequencies for expressed genes, for example, as shown in the codon usage chart from the program "Human-High.cod" from the Wisconsin Sequence Analysis Package, Version 8.1, Genetics Computer Group, Madison, Wis. Codon usage is also described in, for example, R. Nussinov, "Eukaryotic Dinucleotide Preference Rules and Their Implications for Degenerate Codon Usage," *J. Mol. Biol.* 149: 125-131 (1981). The codons which are most frequently used in highly expressed human genes are presumptively the optimal codons for expression in human host cells and, thus, form the bases for constructing a synthetic coding sequence.

As used herein, a "wobble position" refers to the third position of a codon. Mutations in a DNA molecule within the wobble position of a codon typically result in silent or conservative mutations at the amino acid level. For example, there are four codons that encode Glycine, i.e., GGU, GGC, GGA and GGG, thus mutation of any wobble position nucleotide, to any other nucleotide, does not result in a change at the amino acid level of the encoded protein, i.e., is a silent substitution.

The terms "gene", "recombinant gene" and "gene construct" as used herein, refer to a DNA molecule, or portion of a DNA molecule, that encodes a protein. The DNA molecule can contain an open reading frame encoding the protein (as exon sequences) and can further include intron sequences. The term "intron" as used herein, refers to a DNA sequence present in a given gene which is not translated into protein and is generally found between exons. Usually, it is desirable for the gene to be operably linked to, (or it may comprise), one or more promoters, enhancers, repressors and/or other regulatory sequences to modulate the activity or expression of the gene, as is well known in the art.

As used herein, a "complementary DNA" or "cDNA" includes recombinant polynucleotides synthesized by reverse transcription of mRNA and from which intervening sequences (introns) have been removed.

The term "operably linked" as used herein, describes the relationship between two polynucleotide regions such that they are functionally related or coupled to each other. For example, a promoter (or other expression control sequence) is operably linked to a coding sequence if it controls (and is capable of effecting) the transcription of the coding sequence. Although an operably linked promoter is generally located upstream of the coding sequence, it is not necessarily contiguous with it.

"Expression control sequences" are DNA regulatory sequences, such as promoters, enhancers, polyadenylation signals, terminators, internal ribosome entry sites (IRES) and the like, that provide for the expression of a coding sequence in a host cell. Exemplary expression control sequences are described in Goeddel; Gene Expression Technology: Methods in Enzymology 185, Academic Press, San Diego, Calif. (1990).

A "promoter" is a DNA regulatory region capable of binding RNA polymerase in a cell and initiating transcription of a downstream (3' direction) coding sequence. As used herein, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the −10 and −35 consensus sequences.

A large number of promoters, including constitutive, inducible and repressible promoters, from a variety of different sources are well known in the art. Representative sources include for example, viral, mammalian, insect, plant, yeast, and bacterial cell types), and suitable promoters from these sources are readily available, or can be made synthetically, based on sequences publicly available on line or, for example, from depositories such as the ATCC as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include the Tet system, (U.S. Pat. Nos. 5,464,758 and 5,814,618), the Ecdysone inducible system (No et al., *Proc. Natl. Acad. Sci. USA* (1996) 93 (8) 3346-3351; the T-RE$_x$™ system (Invitrogen Carlsbad, Calif.), LacSwitch® (Stratagene, (San Diego, Calif.) and the Cre-ER$^T$ tamoxifen inducible recombinase system (Indra et al. *Nuc. Acid. Res.* (1999) 27 (22)4324-4327; *Nuc. Acid. Res.* (2000) 28 (23) e99; U.S. Pat. No. 7,112,715). See, generally, Kramer & Fussenegger, *Methods Mol. Biol.* (2005) 308 123-144) or any promoter known in the art suitable for expression in the desired cells.

As used herein, a "minimal promoter" refers to a partial promoter sequence which defines the transcription start site but which by itself is not capable, if at all, of initiating transcription efficiently. The activity of such minimal promoters depends on the binding of activators such as a tetracycline-controlled transactivator to operably linked binding sites.

The terms "IRES" or "internal ribosome entry site" refer to a polynucleotide element that acts to enhance the translation of a coding sequence encoded with a. polycistronic messenger RNA. IRES elements, mediate the initiation of translation by directly recruiting and binding ribosomes to a messenger RNA (mRNA) molecule, bypassing the 7-methyl guanosine-cap involved in typical ribosome scanning. The presence of an IRES sequence can increase the level of cap-independent translation of a desired protein. Early publications descriptively refer to IRES sequences as "translation enhancers." For example, cardioviral RNA "translation enhancers" are described in U.S. Pat. No. 4,937,190 to Palmenberg et al. and U.S. Pat. No. 5,770,428 to Boris-Lawrie.

The term "enhancer" as used herein, refers to a DNA sequence that increases transcription of, for example, a gene or coding sequence to which it is operably linked. Enhancers can be located many kilobases away from the coding sequence and can mediate the binding of regulatory factors, patterns of DNA methylation or changes in DNA structure. A large number of enhancers, from a variety of different sources are well known in the art and available as or within cloned polynucleotides (from, e.g., depositories such as the ATCC as well as other commercial or individual sources). A number of polynucleotides comprising promoters (such as the commonly-used CMV promoter) also comprise enhancer sequences. Operably linked enhancers can be located upstream, within, or downstream of coding sequences. The term "Ig enhancers" refers to enhancer elements derived from enhancer regions mapped within the Ig locus (such enhancers include for example, the heavy chain (mu) 5' enhancers, light chain (kappa) 5' enhancers, kappa and mu intronic enhancers, and 3' enhancers, (see, generally Paul WE (Ed.) Fundamental Immunology, 3$^{rd}$ Edition, Raven Press, New York (1993) pages 353-363; U.S. Pat. No. 5,885,827).

"Terminator sequences" are those that result in termination of transcription. Termination sequences are known in the art and include, but are not limited to, poly A (e.g., Bgh Poly A and SV40 Poly A) terminators. A transcriptional termination signal will typically include a region of 3' untranslated region (or "3' ut"), an optional intron (also referred to as intervening sequence or "IVS") and one or more poly adenylation signals ("p(A)" or "pA". Terminator sequences may also be referred to as "IVS–pA", "IVS+p (A)", "3' ut+p(A)" or "3' ut/p(A)". Natural or synthetic terminators can be used as terminator regions.

The terms "polyadenylation", "polyadenylation sequence" and "polyadenylation signal", "Poly A", "p(A)" or "pA" refer to a nucleic acid sequence present in a RNA transcript that allows for a transcript, when in the presence of the polyadenyl transferase enzyme, to be polyadenylated. Many polyadenylation signals are known in the art. Non-limiting examples include the human variant growth hormone polyadenylation signal, the SV40 late polyadenylation signal and the bovine growth hormone polyadenylation signal.

The term "splice site" as used herein refers to polynucleotides that are capable of being recognized by the spicing machinery of a eukaryotic cell as suitable for being cut and/or ligated to a corresponding splice site. Splice sites allow for the excision of introns present in a pre-mRNA transcript. Typically the 5' portion of the splice site is referred to as the splice donor and the 3' corresponding splice site is referred to as the acceptor splice site. The term splice site includes, for example, naturally occurring splice sites, engineered splice sites, for example, synthetic splice sites, canonical or consensus splice sites, and/or non-canonical splice sites, for example, cryptic splice sites.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides. The polynucleotide primers can be prepared using any suitable method, such as, for example, the phosphotriester on phosphodiester methods see Narang et al., *Meth. Enzymol.*, 68:90, (1979); U.S. Pat. No. 4,356,270; and Brown et al., *Meth. Enzymol.*, 68:109, (1979).

As used herein, the terms "restriction endonucleases" and "restriction enzymes" refer to bacterial enzymes, each of which cut double-stranded DNA at, or near, a specific nucleotide sequence. Non-limiting examples of restriction sites are described in more detail below; it will also be understood that other restriction sites are contemplated for use in the described methods so long as they meet the functional requirements described.

The terms "synthetic polynucleotide", "synthetic gene" or "synthetic polypeptide," as used herein, mean that the corresponding polynucleotide sequence or portion thereof, or amino acid sequence or portion thereof, is derived, from a sequence that has been designed, or synthesized de novo, or modified, compared to the equivalent naturally occurring sequence. Synthetic polynucleotides or synthetic genes can be prepared by methods known in the art, including but not limited to, the chemical synthesis of nucleic acid or amino acid sequences. Synthetic genes are typically different from naturally occurring genes, either at the amino acid, or polynucleotide level, (or both) and are typically located within the context of synthetic expression control sequences.

Methods for Engineering Templates

Certain embodiments as disclosed herein provide for novel methods of creating an engineered template by introduction of a predetermined sequence using a nick ligation method for the use in the single primer amplification of antibody genes. In such methods, a polymerase such as, for example, AmpliTaq®, is used for the synthesis of a second strand cDNA that also introduces a predetermined sequence at a 5' or a 3' end of a polynucleotide. In various embodiments, the methods include the steps of annealing an oligonucleotide that anneals to and is complementary to the portion of the polynucleotide, either the first strand cDNA or the second strand cDNA, where the oligonucleotide has a predetermined sequence that anneals to a second oligonucleotide and the annealed polynucleotide and the second oligonucleotide are ligated in the presence of a DNA ligase.

In particularly useful embodiments, the target sequences from the engineered templates are cloned into expression vehicles to provide a library of polypeptides or proteins, such as, for example, an antibody library.

Samples

Samples to be used in the methods described herein can include any biological material which may contain nucleic acid. Samples may originate from a variety of sources. In some embodiments, the sources may be, for example, humans, non-human mammals, mammals, animals, rodents, amphibians, fish, reptiles, microbes, bacteria, plants, fungus, yeast and/or viruses.

In some embodiments, the sample may be a biological sample. In some embodiments, the biological sample may include, for example, cell cultures, tissue sections, frozen sections, biopsy samples and autopsy samples.

The sample can be a clinical sample, an environmental sample or a research sample. Clinical samples can include nasopharyngeal wash, blood, plasma, cell-free plasma, buffy coat, saliva, urine, stool, sputum, mucous, wound swab, tissue biopsy, milk, a fluid aspirate, a swab (e.g., a nasopharyngeal swab), and/or tissue, among others. Research samples can include cultured cells, primary cells, bacteria, spores, viruses, small organisms, any of the clinical samples listed above. Samples can be collected for diagnostic purposes (e.g., the quantitative measurement of a clinical analyte such as an infectious agent) or for monitoring purposes (e.g., to monitor the course of a disease or disorder). For example, samples of polynucleotides may be collected or obtained from a subject having a disease or disorder, at risk of having a disease or disorder, or suspected of having a disease or disorder.

Nucleic acid samples provided in this disclosure can be derived from an organism. In some embodiments, an entire organism may be used. In some embodiments, portion of an organism may be used. For example, a portion of an organism may include an organ, a piece of tissue comprising multiple tissues, a piece of tissue comprising a single tissue, a plurality of cells of mixed tissue sources, a plurality of cells of a single tissue source, a single cell of a single tissue source, cell-free nucleic acid from a plurality of cells of mixed tissue source, cell-free nucleic acid from a plurality of cells of a single tissue source and cell-free nucleic acid from a single cell of a single tissue source and/or body fluids. In some embodiments, the portion of an organism is a compartment such as mitochondrion, nucleus, or other compartment described herein. In some embodiments, the portion of an organism is cell-free nucleic acids present in a fluid, e.g., circulating cell-free nucleic acids.

A tissue can be derived from any of the germ layers. In some embodiments, the germ layers may be neural crest, endoderm, ectoderm and/or mesoderm. The germ layers may give rise to any of the following tissues, connective tissue, skeletal muscle tissue, smooth muscle tissue, nervous system tissue, epithelial tissue, ectodermal tissue, endodermal tissue, mesodermal tissue, endothelial tissue, cardiac muscle tissue, brain tissue, spinal cord tissue, cranial nerve tissue, spinal nerve tissue, neuron tissue, skin tissue, respiratory tissue, reproductive tissue and/or digestive tissue. In some embodiments, the organ can be derived from any of the germ layers. In some embodiments, the germ layers may give rise to any of the following organs, adrenal glands, anus, appendix, bladder, bones, brain, bronchi, ears, esophagus, eyes, gall bladder, genitals, heart, hypothalamus, kidney, larynx, liver, lungs, large intestine, lymph nodes, meninges, mouth, nose, pancreas, parathyroid glands, pituitary gland, rectum, salivary glands, skin, skeletal muscles, small intestine, spinal cord, spleen, stomach, thymus gland, thyroid, tongue, trachea, ureters and/or urethra. In some embodiments, the organ may include a neoplasm. In some embodiments, the neoplasm may be a tumor. In some embodiments, the tumor may be cancer.

A cell can be derived from any tissue. In some embodiments, the cell may include exocrine secretory epithelial cells, hormone secreting cells, keratinizing epithelial cells, wet stratified barrier epithelial cells, sensory transducer cells, autonomic neuron cells, sense organ and peripheral neuron supporting cells, central nervous system neurons, glial cells, lens cells, metabolism and storage cells, kidney cells, extracellular matrix cells, contractile cells, blood and immune system cells, germ cells, nurse cells and/or interstitial cells.

Body fluids may be suspensions of biological particles in a liquid. For example, a body fluid may be blood. In some embodiments, blood may include plasma and/or cells (e.g., red blood cells, white blood cells, or circulating rare cells) and/or platelets. In some embodiments, a blood sample contains blood that has been depleted of one or more cell types. In some embodiments, a blood sample contains blood that has been enriched for one or more cell types. In some embodiments, a blood sample contains a heterogeneous, homogenous or near-homogenous mix of cells. Body fluids can include, for example, whole blood, fractionated blood, serum, plasma, sweat, tears, ear flow, sputum, lymph, bone marrow suspension, lymph, urine, saliva, semen, vaginal flow, feces, transcervical lavage, cerebrospinal fluid, brain fluid, ascites, breast milk, vitreous humor, aqueous humor, sebum, endolymph, peritoneal fluid, pleural fluid, cerumen, epicardial fluid, and secretions of the respiratory, intestinal and/or genitourinary tracts. In some embodiments, body fluids can be in contact with various organs (e.g. lung) that contain mixtures of cells.

Body fluids can contain at least one cell. Cells may include, for example, cells of a malignant phenotype; fetal cells (e.g., fetal cells in maternal peripheral blood); tumor cells, (e.g., tumor cells which have been shed from tumor into blood and/or other bodily fluids); cancerous cells; immortal cells; stem cells; cells infected with a virus, (e.g., cells infected by HIV); cells transfected with a gene of interest; aberrant subtypes of T-cells and/or B-cells present in the peripheral blood of subjects afflicted with autoreactive disorders. In some embodiments, the cell may be one of the following, erythrocytes, white blood cells, leukocytes, lymphocytes, B cells, T cells, mast cells, monocytes, macrophages, neutrophils, eosinophils, dendritic cells, stem cells, erythroid cells, cancer cells, tumor cells or cell isolated from any tissue originating from the endoderm, mesoderm, ectoderm and/or neural crest tissues. Cells may be from a primary source and/or from a secondary source (e.g., a cell line). The body fluids may also contain polynucleotides, e.g., cell-free fetal polynucleotides or DNA circulating in maternal blood.

The nucleic acids within a sample may be located within a region of a cell or a cellular compartment. The region or compartment of a cell may include a membrane, an organelle and/or the cytosol. For example, the membranes may include, but are not limited to, nuclear membrane, plasma membrane, endoplasmic reticulum membrane, cell wall, cell membrane and/or mitochondrial membrane. The membranes may include a complete membrane or a fragment of a membrane. For example, the organelles may include, but are not limited to, the nucleolus, nucleus, chloroplast, plastid, endoplasmic reticulum, rough endoplasmic reticulum, smooth endoplasmic reticulum, centrosome, golgi apparatus, mitochondria, vacuole, acrosome, autophagosome, centriole, cilium, eyespot apparatus, glycosome, glyoxysome, hydrogenosome, lysosome, melanosome, mitosome, myofibril, parenthesome, peroxisome, proteasome, ribosome, vesicle, carboxysome, chlorosome, flagellum, magenetosome, nucleoid, plasmid, thylakoid, mesosomes, cytoskeleton, and/or vesicles. In some embodiments, the organelles may include a complete membrane or a fragment of a membrane. For example, the cytosol may be encapsulated by the plasma membrane, cell membrane and/or the cell wall.

A sample may comprise nucleic acids that are not bound to protein. The nucleic acids may be treated with an agent to reduce protein binding, remove bound proteins and/or prevent protein binding. In some embodiments, the agent may be a chemical agent, a source of temperature change, a source of sound energy, a source of optical energy, a source of light energy, and/or a source of heat energy. In some embodiments, the chemical agent may be an enzyme. In some embodiments, the enzyme may cleave the bonds between amino acids of a protein.

Samples comprising nucleic acids may comprise deoxyribonucleic acid (DNA), genomic DNA, mitochondrial DNA, complementary DNA, synthetic DNA, plasmid DNA, viral DNA, linear DNA, circular DNA, double-stranded DNA, single-stranded DNA, digested DNA, fragmented DNA, ribonucleic acid (RNA), small interfering RNA, messenger RNA, transfer RNA, micro RNA, duplex RNA, double-stranded RNA and/or single-stranded RNA.

In some embodiments, nucleic acid (e.g., genomic DNA) may be the entire genome of a species, such as viruses, yeast, bacteria, animals, and plants. The nucleic acid (e.g., genomic DNA) may be from still higher life forms (e.g., human genomic DNA). In some embodiments, the nucleic acid (e.g., genomic DNA) may comprise one or more chromatid fibers, or at least 25%, 50%, 75%, 80%, 90%, 95%, or 98% of the nucleic acid (e.g., genomic DNA) of the species or of an organism or cell.

In some embodiments, the nucleic acid may contain the nucleic acid sequence of a heavy chain or a light chain of an antibody or a fragment thereof. In some embodiments, the nucleic acid may contain the nucleic acid sequence of more than one heavy chain or light chain of an antibody or a fragment thereof. For example, the antibody may be of any type, but not limited to, IgA, IgD, IgE, IgG, IgY or IgM. The nucleic acid may contain the sequence of more than one antibody where each antibody is of the same subtype. The nucleic acid may contain the sequence of more than one antibody where each antibody is a different subtype.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains (Fc) that correspond to the different classes of immunoglobulins are called α, δ, ε, γ, and μ, respectively. The subunit structures and three-dimensional configurations of different classes of immunoglobulins are well known.

The "light chains" of antibodies (immunoglobulins) from any vertebrate species can be assigned to one of two clearly distinct types, called kappa or ("κ") and lambda or ("λ"), based on the amino acid sequences of their constant domains.

The terms "antigen-binding portion of an antibody," "antigen-binding fragment", "antigen-binding domain", "antibody fragment" or a "functional fragment of an antibody" are used interchangeably in the present invention to mean one or more fragments of an antibody that retain the ability to specifically bind to an antigen, (see generally, Holliger et al., *Nature Biotech.* 23 (9) 1126-1129 (2005)). Non-limiting examples of antibody fragments included within, but not limited to, the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544 546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423 426; and Huston et al. (1988) *Proc. Natl. Acad. Sci. USA* 85:5879 5883; and Osbourn et al. (1998) *Nat. Biotechnol.* 16:778). Such single chain antibodies are also intended to be encompassed within the term "antigen-binding portion" of an antibody. Any $V_H$ and $V_L$ sequences of specific scFv can be linked to human immunoglobulin constant region cDNA or genomic sequences, in order to generate expression vectors encoding complete IgG molecules or other isotypes. $V_H$ and $V_L$ can also be used in the generation of Fab, Fv or other fragments of immunoglobulins using either protein chemistry or recombinant DNA technology. Other forms of single chain antibodies, such as diabodies are also encompassed.

"F(ab')$_2$" and "Fab'" moieties can be produced by treating immunoglobulin (monoclonal antibody) with a protease such as pepsin and papain, and includes an antibody fragment generated by digesting immunoglobulin near the disulfide bonds existing between the hinge regions in each of the two H chains. For example, papain cleaves IgG upstream of the disulfide bonds existing between the hinge regions in each of the two H chains to generate two homologous antibody fragments in which an L chain composed of $V_L$ (L chain variable region) and $C_L$ (L chain constant region), and an H chain fragment composed of $V_H$ (H chain variable region) and $C_{H\gamma1}$ (γ1 region in the constant region of H chain) are connected at their C terminal regions through a disulfide bond. Each of these two homologous antibody fragments is called Fab'. Pepsin also cleaves IgG downstream of the disulfide bonds existing between the hinge regions in each of the two H chains to generate an antibody fragment slightly larger than the fragment in which the two above-mentioned Fab' are connected at the hinge region. This antibody fragment is called F(ab')2.

The Fab fragment also contains the constant domain of the light chain and the first constant domain ($C_{H1}$) of the heavy chain. Fab' fragments differ from Fab fragments by the addition of a few residues at the carboxyl terminus of the heavy chain $C_{H1}$ domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

"Single-chain Fv" or "sFv" antibody fragments comprise the $V_H$ and $V_L$ domains of an antibody, wherein these domains are present in a single polypeptide chain. Generally, the Fv polypeptide further comprises a polypeptide linker between the $V_H$ and $V_L$ domains which enables the sFv to form the desired structure for antigen binding. For a review of sFv see Pluckthun in The Pharmacology of Monoclonal Antibodies, vol. 113, Rosenburg and Moore, Eds. Springer-Verlag, New York, pp. 269 315 (1994).

In some embodiments, the nucleic acid may contain a part of the antibody. For example, the part of the antibody may be a complementary determining region (CDR), variable fragment (Fv), ab fragment (Fab) or crystallizable fragment (Fc).

Methods of Preparing Polynucleotides

In the disclosure provided herein, nucleic acids may be isolated from at least one sample to obtain a polynucleotide. Standard methods of isolating deoxyribonucleic acid (DNA), genomic DNA, mitochondrial DNA, complementary DNA, synthetic DNA, plasmid DNA, viral DNA, linear DNA, circular DNA, double-stranded DNA, single-stranded DNA, digested DNA, fragmented DNA, ribonucleic acid (RNA), small interfering RNA, messenger RNA, transfer RNA, micro RNA, duplex RNA, double-stranded RNA and/or single-stranded RNA from a sample are known to those of skill in the art and may be used with the methods herein to obtain a polynucleotide. In a preferred embodiment, total RNA may be isolated from a sample and converted to complementary DNA (cDNA) using methods known to those of skill in the art (e.g., reverse transcription) to generate a first or a second strand cDNA.

In some embodiments, the polynucleotide may have one portion. In some embodiments, the polynucleotide may have more than one portion. For example, the polynucleotide may have a first, second, third, fourth, fifth, sixth, seventh, eighth, ninth or tenth portion. In some embodiments, any portion of the polynucleotide may be disposed near the 5' end of the polynucleotide. In some embodiments, any portion of the polynucleotide may be disposed near the 3' end of the polynucleotide. In some embodiments, any portion of the polynucleotide may be disposed near the middle of the polynucleotide. In some embodiments, a first portion of the polynucleotide may be disposed near the 5' end of the polynucleotide. In some embodiments, a first portion of the polynucleotide may be disposed near the 3' end of the polynucleotide. In some embodiments, a first portion of the polynucleotide may be disposed near the middle of the polynucleotide. In some embodiments, a second portion of the polynucleotide may be disposed near the 5' end of the polynucleotide. In some embodiments, a second portion of the polynucleotide may be disposed near the 3' end of the polynucleotide. In some embodiments, a second portion of the polynucleotide may be disposed near the middle of the polynucleotide. In some embodiments, a third portion of the polynucleotide may be disposed near the 5' end of the polynucleotide. In some embodiments, a third portion of the polynucleotide may be disposed near the 3' end of the polynucleotide. In some embodiments, a third portion of the polynucleotide may be disposed near the middle of the polynucleotide.

Libraries

As used herein, "library" refers to a plurality of polynucleotides, proteins, or cells comprising a collection of two, or two or more, non-identical but related members. A "synthetic library" refers to a plurality of synthetic polynucleotides, or a population of cells that comprise said plurality of synthetic polynucleotides. A "semi-synthetic library" refers to a plurality of semi-synthetic polynucleotides, or a population of cells that comprise said plurality of semi-synthetic polynucleotides.

Static libraries are typically limited in their size and scope. Phage display libraries, for example can display as many as $10^{12}$ members, and ribosomal libraries have been constructed that potentially contain ~$10^{16}$ members. Libraries presented on the surface of bacterial and mammalian cells are not usually this complex, typically with fewer than $10^9$ members. In addition, robust library construction and selection usually requires that libraries contain several fold redundancy, which further limits this theoretically complexity, and makes screening the entire library slow, expensive, and in some cases in-practical.

Despite these levels of complexity, such static libraries can explore only a small fraction of possible sequence space, i.e., the potential number of possible permutations within a polynucleotide region of interest. For example, a heavy chain IgG sequence may contain more than 30 amino acids within the CDR1, CDR2, and CDR3 complementarity regions, giving this single chain more than $20^{30}$ possible permutations, dwarfing even the largest of potential static libraries. Because of this limitation, researchers have explored methodologies for evolving protein sequences and libraries.

In the disclosure provided herein, libraries of samples may be generated by cloning the antibody fragments amplified by a single primer at engineered restriction sites including, but not limited to, XbaI, BspEI, SalI, XhoI, SalI, and AgeI, into suitable vectors for phage display, bacterial expression, and mammalian expression. Other restriction sites are described below and are considered for use in the methods described herein.

This library can have the following properties: i) The construction of libraries is easy especially when the preparation of template is multiplexed with mixed primers. ii) The library is potentially more diverse covering unbiased antibody repertoire up to $10^{10}$ to $10^{12}$ compared to the ones made using traditional PCR method. Traditional PCR amplification requires two gene-specific primers that have different annealing temperatures that are often problematic to optimize. This leads biased amplification and non-specific amplification and results in poor quality in the constructed libraries. iii) As the potential diversity is higher, as shown in the example, multiple antigens can be used to immunize one mouse and a single library can be used to isolate large panel of antibodies to each antigen.

In some embodiments, the types of libraries may include Fab, F(ab')$_2$, scFv fragments of antibody of mouse, rat, rabbit, human, chicken, shark, llama, horse, monkeys, goats, frogs, fish, etc.

Cell based expression systems include any suitable prokaryotic or eukaryotic expression system. In certain embodiments, the preferred cell-based expression systems are those that can be easily and reliably grown, have reasonably fast growth rates, have well characterized expression systems and can be transformed or transfected easily and efficiently.

Phage Display

"Phage display" is a technique by which variant polypeptides are displayed as fusion proteins to at least a portion of a coat protein on the surface of phage, e.g., filamentous phage, particles. A utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991).

A "phagemid" is a plasmid vector having a bacterial origin of replication, e.g., Co1E1, and a copy of an intergenic region of a bacteriophage. Phagemids may be used on any known bacteriophage, including filamentous bacteriophage and lambdoid bacteriophage. Generally, the plasmid will also contain a selectable marker for antibiotic resistance. Segments of DNA cloned into these vectors can be propagated as plasmids. When cells harboring vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids, which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, fl, fd, Pf3 phage or a derivative thereof, or a lambdoid phage, such as lambda, 21, phi80, phi81, 82, 424, 434, etc., or a derivative thereof.

The term "coat protein" means a protein, at least a portion of which is present on the surface of the virus particle. From a functional perspective, a coat protein is any protein, which associates with a virus particle during the viral assembly process in a host cell, and remains associated with the assembled virus until it infects another host cell. The coat protein may be the major coat protein or may be a minor coat protein. A "major" coat protein is generally a coat protein which is present in the viral coat at preferably at least about 5, more preferably at least about 7, even more preferably at least about 10 copies of the protein or more. A major coat protein may be present in tens, hundreds or even thousands of copies per virion. An example of a major coat protein is the p8 protein of filamentous phage.

Prokaryotic Expression Systems

Within these general guidelines, useful microbial hosts include bacteria from the genera *Bacillus, Escherichia* (such as *E. coli*), *Pseudomonas, Streptomyces, Salmonella, Erwinia, Bacillus subtilis, Bacillus brevis*, the various strains of *Escherichia coli* (e.g., HB101, (ATCC NO. 33694) DH5α, DH10, and MC1061 (ATCC NO. 53338)).

Eukaryotic Expression Systems

Yeast

Many strains of yeast cells known to those skilled in the art are also available as host cells for the expression of polypeptides including those from the genera *Hansenula, Kluyveromyces, Pichia*, Rhino-sporidium, *Saccharomyces*, and *Schizosaccharomyces*, and other fungi. Preferred yeast cells include, for example, *Saccharomyces cerivisae* and *Pichia pastoris*.

Insect Cells

Additionally, where desired, insect cell systems can be utilized in the methods of the present invention. Such systems are described, for example, by Kitts et al., *Biotechniques*, 14:810-817 (1993); Lucklow, *Curr. Opin. Biotechnol.*, 4:564-572 (1993); and Lucklow et al. (*J. Virol.*, 67:4566-4579 (1993). Preferred insect cells include Sf-9 and HI5(Invitrogen, Carlsbad, Calif.).

Mammalian Expression Systems

A number of suitable mammalian host cells are also known in the art and many are available from the American Type Culture Collection (ATCC), 10801 University Boulevard, Manassas, Va. 20110-2209. Examples include, but are not limited to, mammalian cells, such as Chinese hamster ovary cells (CHO) (ATCC No. CCL61) CHO DHFR-cells (Urlaub et al., *Proc. Natl. Acad. Sci. USA*, 97:4216-4220 (1980)), human embryonic kidney (HEK) 293 or 293T cells (ATCC No. CRL1573), PER.C6™ cells, or 3T3 cells (ATCC No. CCL92). The selection of suitable mammalian host cells and methods for transformation, culture, amplification, screening and product production and purification are known in the art. Other suitable mammalian cell lines are the monkey COS-1 (ATCC No. CRL1650) and COS-7 cell lines (ATCC No. CRL1651), and the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Candidate cells can be genotypically deficient in the selection gene, or may contain a dominantly acting selection gene. Other suitable mammalian cell lines include, but are not limited to, mouse neuroblastoma N2A cells, HeLa, mouse L-929 cells, 3T3 lines derived from Swiss, BALB/c or NIH mice, BHK or HaK hamster cell lines, which are available from the ATCC. Each of these cell lines is known by and available for protein expression.

Also of interest are lymphoid, or lymphoid derived cell lines, such as a cell line of pre-B lymphocyte origin. Specific examples include without limitation RAIVIOS(CRL-1596), Daudi (CCL-213), EB-3 (CCL-85), DT40 (CRL-2111), 18-81, (Jack et al., *PNAS USA* (1988) 85 1581-1585), Raji cells, (CCL-86) and derivatives thereof.

Representative commercially available viral expression vectors include, but are not limited to, the adenovirus-based Per.C6 system available from Crucell, Inc., the lentiviral-based pLP1 from Invitrogen, and the Retroviral Vectors pFB-ERV plus pCFB-EGSH from Stratagene.

An episomal expression vector suitable for the expression of the libraries described herein is able to replicate in the host cell, and persists as an extrachromosomal episome within the host cell in the presence of appropriate selective pressure. (See for example, Conese et al., *Gene Therapy* 11 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP), specific examples include the vectors pREP4, pCEP4, pREP7 from Invitrogen. The vectors pcDNA3.1 from Invitrogen, and pBK-CMV from Stratagene represent non-limiting examples of an episomal vector that uses T-antigen and the SV40 origin of replication in lieu of EBNA1 and oriP.

Oligonucleotides

An oligonucleotide to be used in the methods described herein may be used to prepare a universal template. In some embodiments, one oligonucleotide may be used to prepare a universal template. In some embodiments, more than one oligonucleotide may be used to prepare a universal template. For example, 1, 2, 3, 4, 5, 6, 7, 8, 9, or 10 oligonucleotides may be used to prepare a universal template. In some embodiments, more than 10 oligonucleotides may be used to prepare a universal template. For example, a first, a second, a third, a fourth, a fifth, a sixth, a seventh, an eighth, a ninth and/or a tenth oligonucleotide may be used to prepare a universal template. In some embodiments, an oligonucleotide may be an adaptor oligonucleotide. In some embodiments, the adaptor oligonucleotides may be annealed together prior to annealing the adaptor oligonucleotides to the polynucleotide. In some embodiments, the adaptor oligonucleotides may be annealed together prior to ligating the adaptor oligonucleotides to the polynucleotide.

In some embodiments, the oligonucleotide may contain a plurality of nucleotides. For example, an oligonucleotide may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or 100 nucleotides. In some embodiments, an oligonucleotide may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or more than 100 nucleotides. In some embodiments, an oligonucleotide may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or less than 100 nucleotides.

In some embodiments, an oligonucleotide may contain a desired sequence. In some embodiments, an oligonucleotide may contain more than one desired sequence. For example, a desired sequence may be a restriction endonuclease restriction site, a pre-determined sequence, a complementary sequence, a known sequence, a primer binding sequence, a universal sequence, or a detection sequence. In some embodiments, a pre-determined sequence may be a universal sequence.

In some embodiments, a plurality of oligonucleotides may be used to add more than one desired sequence to a polynucleotide to create the engineered template. In some embodiments, the desired sequence may be a predetermined sequence. For example, the predetermined sequence may be a first, second, third, fourth, fifth, sixth, seventh, eighth, ninth or tenth predetermined sequence. In some embodiments, any predetermined sequence within the oligonucleotide may be disposed near the 5' end of the oligonucleotide. In some embodiments, any predetermined sequence within the oligonucleotide may be disposed near the 3' end of the oligonucleotide. In some embodiments, any predetermined sequence within the oligonucleotide may be disposed near the middle of the oligonucleotide. In some embodiments, a first predetermined sequence of the oligonucleotide may be disposed near the 5' end of the oligonucleotide. In some embodiments, a first predetermined sequence of the oligonucleotide may be disposed near the 3' end of the oligonucleotide. In some embodiments, a first predetermined sequence of the oligonucleotide may be disposed near the middle of the oligonucleotide. In some embodiments, a second predetermined sequence of the oligonucleotide may be disposed near the 5' end of the oligonucleotide. In some embodiments, a second predetermined sequence of the oligonucleotide may be disposed near the 3' end of the oligonucleotide. In some embodiments, a second predetermined sequence of the oligonucleotide may be disposed near the middle of the oligonucleotide. In some embodiments, a third predetermined sequence of the oligonucleotide may be disposed near the 5' end of the oligonucleotide. In some embodiments, a third predetermined sequence of the oligonucleotide may be disposed near the 3' end of the oligonucleotide. In some embodiments, a third predetermined sequence of the oligonucleotide may be disposed near the middle of the oligonucleotide.

In some embodiments, the first pre-determined sequence and the second pre-determined sequence are not substantially similar to any sequence within the first or the second polynucleotide.

In some embodiments, the desired sequence may be any length of nucleotides less than the length of the oligonucleotide. For example, the desired sequence may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 96, 97, 98 or 99 nucleotides. In some embodiments, the desired sequence may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or more than 95 nucleotides. In some embodiments, the desired sequence may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or less than 95 nucleotides.

The oligonucleotide may contain nucleotides which bind to a polynucleotide. In some embodiments, nucleotides which bind to a polynucleotide contained within the oligonucleotide may be located at any site within the oligonucleotide. In some embodiments, the nucleotides which bind to a polynucleotide may be at the 3' end of the oligonucleotide. In some embodiments, the nucleotides which bind to a polynucleotide may be at the 5' end of the oligonucleotide. In some embodiments, the nucleotides which bind to a polynucleotide may be substantially near the 3' end of the oligonucleotide. For example, the 3' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the oligonucleotide. In some embodiments, the nucleotides which bind to a polynucleotide may be substantially near the 5' end of the oligonucleotide. For example, the 5' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the oligonucleotide. In some embodiments the nucleotides which bind to a polynucleotide may be in the middle of the oligonucleotide.

In some embodiments, the nucleotides which bind to a polynucleotide may be any length of nucleotides less than the length of the oligonucleotide. For example, the nucleotides which bind to a polynucleotide may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 96, 97, 98 or 99 nucleotides. In some embodiments, the nucleotides which bind to a polynucleotide may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or more than 95 nucleotides. In some embodiments, the nucleotides which bind to a polynucleotide may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or less than 95 nucleotides.

The nucleotides which bind to a polynucleotide contained within the oligonucleotide may be located at any site within the oligonucleotide. In some embodiments, the nucleotides which bind to a polynucleotide may be at the 3' end of the oligonucleotide. In some embodiments, the nucleotides which bind to a polynucleotide may be at the 5' end of the oligonucleotide. In some embodiments, the nucleotides which bind to a polynucleotide may be substantially near the 3' end of the oligonucleotide. For example, the 3' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the oligonucleotide. In some embodiments, the nucleotides which bind to a polynucleotide may be substantially near the 5' end of the oligonucleotide. For example, the 5' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the oligonucleotide. In some embodiments, the nucleotides which bind to a polynucleotide may be in the middle of the oligonucleotide.

In some embodiments, the oligonucleotide may have one portion. In some embodiments, the oligonucleotide may have more than one portion. For example, the oligonucleotide may have a first, second, third, fourth, fifth, sixth, seventh, eighth, ninth or tenth portion. In some embodiments, any portion of the oligonucleotide may be disposed near the 5' end of the oligonucleotide. In some embodiments, any portion of the oligonucleotide may be disposed near the 3' end of the oligonucleotide. In some embodiments, any portion of the oligonucleotide may be disposed near the middle of the oligonucleotide. In some embodiments, a first portion of the oligonucleotide may be disposed near the 5' end of the oligonucleotide. In some embodiments, a first portion of the oligonucleotide may be disposed near the 3' end of the oligonucleotide. In some embodiments, a first portion of the oligonucleotide may be disposed near the middle of the oligonucleotide. In some embodiments, a second portion of the oligonucleotide may be disposed near the 5' end of the oligonucleotide. In some embodiments, a second portion of the oligonucleotide may be disposed near the 3' end of the oligonucleotide. In some embodiments, a second portion of the oligonucleotide may be disposed near the middle of the oligonucleotide. In some embodiments, a third portion of the oligonucleotide may be disposed near the 5' end of the oligonucleotide. In some embodiments, a third portion of the oligonucleotide may be disposed near the 3' end of the oligonucleotide. In some embodiments, a third portion of the oligonucleotide may be disposed near the middle of the oligonucleotide.

In some embodiments, a polynucleotide may be contacted with at least one oligonucleotide containing a desired sequence. In some embodiments, the oligonucleotide may be, but not limited to, hybridized, annealed or ligated to the polynucleotide. For example, the oligonucleotide with the desired sequence (e.g., a predetermined sequence) may be ligated to the polynucleotide using an enzyme. For example, the enzyme may be a ligase (e.g., a DNA ligase). In some embodiments, the oligonucleotide containing a predetermined sequence may be ligated to the 3' end or the 5' end of the polynucleotide. In some embodiments, more than one pre-determined sequence may be ligated to the polynucleotide. For example, a first pre-determined sequence may be ligated to one end of the polynucleotide and a second pre-determined sequence may be ligated to the other end of the polynucleotide. In some embodiments, the first pre-determined sequence may be complementary to the second pre-determined sequence. In some embodiments, the first pre-determined sequence may be reverse complementary to the second pre-determined sequence. In some embodiments, the first pre-determined sequence may not be complementary to the second pre-determined sequence.

In some embodiments, the addition of at least one pre-determined sequence to a polynucleotide may create a template (e.g., an engineered template). For example, the template may be used in any method designed to amplify the polynucleotide within the template. The pre-determined sequence may be used in primer amplification of the polynucleotide. In some embodiments, a single primer may be annealed to at least one pre-determined sequence located on the polynucleotide. In other embodiments, more than one primer may be annealed to at least one pre-determined sequence located on the polynucleotide.

In some embodiments, a restriction endonuclease restriction site may be located within the oligonucleotide. For example, the restriction endonuclease restriction site may be any site which is recognized by a restriction endonuclease where the restriction endonuclease restriction site within the oligonucleotide is a restriction endonuclease restriction site native to the polynucleotide. For example, any sites recognized by any one of the following restriction endonucleases, but not limited to the following, may be used; Aar I, Ban II, BseG I, BspP I, Cfr I, EcoN I, Hsp92 II, Nla IV, Rsa I, Tai I, Aas I, Bbs I, BseJ I, BspT I, Cla I, EcoO109 I, I-Ppo I, NmuC I, Rsr II, Taqa I, Aat II, Bbu I, BseL I, BsrB I, Cpo I, EcoR I, Kas I, Not I, Sac I, Taq I, Acc65 I, BbvC I, BseM I, BsrD I, Csp45 I, EcoR V, Kpn2 I, Nru I, Sac II, Tas I, AccB7 I, Bbv I, BseM II, BsrF I, Csp6 I, Ehe I, Kpn I, Nsb I, Sal I, Tat I, Acc I, BceA I, BseN I, BsrG I, Csp I, Esp3 I, KspA I, Nsi I, Sap I, Tau I, Acc III, Bcg I, BseR I, Bsr I, Dde I, Fau I, Lwe I, Nsp I, Sat I, Tfi I, Aci I, Bci VI, BseS I, BsrS I, Dpn I, Fnu4H I, Mbi I, Oli I, Sau3A I, Tli I, Acl I, Bcl I, BseX I, BssH II, Dpn II, Fok I, Mbo I, Pac I, Sau96 I, Tru1 I, Ade I, Bcn I, BseY I, BssK I, Dra I, Fse I, Mbo II, Pae I, Sbf I, Tru9 I, Afe I, Bcu I, Bsg I, BssS I, Dra III, FspA I, Mfe I, PaeR7 I, Sca I, Tse I, Afl II, Bfa I, Bsh1236 I, Bst1107 I, Drd I, Fsp I, Mls I, Pag I, Sch I, Tsp45 I, Afl III, Bfi I, Bsh1285 I, Bst98 I, Eae I, Gsu I, Mlu I, Pau I, ScrF I, Tsp509 I, Age I, Bfm I, BshN I, BstAP I, Eag I, Hae II, Mly I, Pci I, Sda I, TspR I, Ahd I, BfrB I, BshT I, BstB I, Eam1104 I, Hae III, Mme I, Pdi I, Sdu I, Tth111 I, Ale I, BfuA I, BsiE I, BstE II, Eam1105 I, Hga I, Mnl I, Pdm I, SexA I, TurboNae I, Alo I, BfuC I, BsiHKA I, BstF5 I, Ear I, Hha I, Mph1103 I, Pfl23 II, SfaN I, TurboNar I, Alu I, Bfu I, BsiW I, BstN I, Eci I, Hin1 I, Msc I, PflF I, Sfc I, Van91 I, Alw21 I, Bgl I, Bsl I, BstO I, Ecl136 II, Hin4 I, Mse I, PflM I, Sfi I, Vsp I, Alw26 I, Bgl II, BsmA I, BstU I, EclHK I, Hin6 I, Msl I, Pfo I, Sfo I, Xag I, Alw44 I, Blp I, BsmB I, BstX I, Eco105 I, Hinc II, MspA1 I, Ple I, Sgf I, Xap I, Alw I, Bme1390 I, BsmF I, BstY I, Eco130 I, Hind III, Msp I, Pme I, SgrA I, Xba I, AlwN I, Box I, Bsm I, BstZ I, Eco147 I, Hinf I, Mss I, Pml I, Sin I, Xce I, Apa I, Bpi I, BsoB I, Bsu15 I, Eco24 I, HinP1 I, Mun I, Ppi I, Sma I, Xcm I, ApaL I, Bpl I, Bsp119 I, Bsu36 I, Eco31 I, Hpa I, Mva1269 I, PpuM I, Smi I, Xho I, Apo I, Bpu10 I, Bsp120 I, BsuR I, Eco32 I, Hpa II, Mva I, PshA I, Sml I, Xho II, Asc I, Bpu1102 I, Bsp1286 I, Btg I, Eco47 I, Hph I, Mwo I, Psi I, Smu I, Xma I, Ase I, BsaA I, Bsp1407 I, Bts I, Eco47 III, Hpy188 I, Nae I, Psp1406 I, SnaB I, XmaJ I, AsiS I, BsaB I, Bsp143 I, Bve I, Eco52 I, Hpy188 III, Nar I, Psp5 II, Spe I, Xmi I, Ava I, BsaH I, Bsp143 II, Cac8 I, Eco57 I, Hpy8

I, Nci I, PspG I, Sph I, Xmn I, Ava II, Bsa I, Bsp68 I, Cai I, Eco57M I, Hpy99 I, Nco I, PspOM I, Ssp I, Avr II, BsaJ I, BspD I, Cfo I, Eco72 I, HpyCH4 III, Nde I, Pst I, Stu I, Bae I, BsaM II, BspE I, Cfr10 I Eco81 I HpyCH4 IV, Nde II, Psu I, StyD4 I, Bal I, BsaW I, BspH I, Cfr13 I, Eco88 I, HpyCH4 V, NgoM IV, Psy I, Sty I, BamH I, BsaX I, BspL I, Cfr42 I, Eco91 I, HpyF10 VI, Nhe I, Pvu I, Swa I, Ban I, BseD I, BspM I, Cfr9 I, EcoICR I, Hsp92 I, Nla III, Pvu II, Taa I, Bln I, and PspX I.

In some embodiments, the restriction site may be unique to one restriction endonuclease. In some embodiments, the restriction site may be recognized by more than one restriction endonuclease. In some embodiments, the restriction site may be recognized by a blunt-cut restriction endonuclease. In some embodiments, the restriction site may be recognized by a sticky-cut restriction endonuclease.

Primers

In the disclosure provided herein, at least one primer may be used to prepare a universal template. In some embodiments, one primer may be used to prepare a universal template. In some embodiments, more than one primer may be used to prepare a universal template. For example, 1, 2, 3, 4, 5, 6, 7, 8, 9, or 10 primers may be used to prepare a universal template. In some embodiments, more than 10 primers may be used to prepare a universal template. For example, a first, a second, a third, a fourth, a fifth, a sixth, a seventh, an eighth, a ninth and/or a tenth primer may be used to prepare a universal template. In some embodiments, a set of primers may be used to prepare a universal template.

In some embodiments, the primer may contain a plurality of nucleotides. For example, a primer may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or 100 nucleotides. In some embodiments, a primer may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or more than 100 nucleotides. In some embodiments, a primer may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95 or less than 100 nucleotides.

In some embodiments, a primer may contain a desired sequence. In some embodiments, a primer may contain more than one desired sequence. For example, a desired sequence may be a pre-determined sequence, a complementary sequence, a known sequence, a binding sequence, a universal sequence, or a detection sequence. In some embodiments, a pre-determined sequence may be a universal sequence.

In some embodiments, the desired sequence may be any length of nucleotides less than the length of the primer. For example, the desired sequence may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 96, 97, 98 or 99 nucleotides. In some embodiments, the desired sequence may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or more than 95 nucleotides. In some embodiments, the desired sequence may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or less than 95 nucleotides.

The primer may contain nucleotides which bind to a polynucleotide. In some embodiments, nucleotides which bind to a polynucleotide contained within the primer may be located at any site within the primer. In some embodiments, the nucleotides which bind to a polynucleotide may be at the 3' end of the primer. In some embodiments, the nucleotides which bind to a polynucleotide may be at the 5' end of the primer. In some embodiments, the nucleotides which bind to a polynucleotide may be substantially near the 3' end of the primer. For example, the 3' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the primer. In some embodiments, the nucleotides which bind to a polynucleotide may be substantially near the 5' end of the primer. For example, the 5' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the primer. In some embodiments the nucleotides which bind to a polynucleotide may be in the middle of the primer.

In some embodiments, the nucleotides which bind to a polynucleotide may be any length of nucleotides less than the length of the primer. For example, the nucleotides which bind to a polynucleotide may contain 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90, 95, 96, 97, 98 or 99 nucleotides. In some embodiments, the nucleotides which bind to a polynucleotide may contain more than 1, 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or more than 95 nucleotides. In some embodiments, the nucleotides which bind to a polynucleotide may contain less than 2, 3, 4, 5, 6, 7, 8, 9, 10, 11, 12, 13, 14, 15, 16, 17, 18, 19 20, 21, 22, 23, 24, 25, 26, 27, 28, 29 30, 31, 32, 33, 34, 35, 36, 37, 38, 39, 40, 41, 42, 43, 44, 45, 46, 47, 48, 49 50, 55, 60, 65, 70, 75, 80, 85, 90 or less than 95 nucleotides.

The nucleotides which bind to a polynucleotide contained within the primer may be located at any site within the primer. In some embodiments, the nucleotides which bind to a polynucleotide may be at the 3' end of the primer. In some embodiments, the nucleotides which bind to a polynucleotide may be at the 5' end of the primer. In some embodiments, the nucleotides which bind to a polynucleotide may be substantially near the 3' end of the primer. For example, the 3' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the primer. In some embodiments, the nucleotides which bind to a polynucleotide may be substantially near the 5' end of the primer. For example, the 5' end of the nucleotides which bind to a polynucleotide may be 1, 2, 3, 4, 5, 6, 7, 8, 9, 10, 11, 12, 13, 14, 15, 16, 17, 18, 19, 20, 21, 22, 23, 24, 25, 26, 27, 28, 29 30, 31, 32, 33, 34, 35, 36, 37, 38, 39, 40, 41, 42, 43, 44, 45, 46, 47, 48 or 49 nucleotides from the middle of the primer.

In some embodiments, the nucleotides which bind to a polynucleotide may be in the middle of the primer.

In some embodiments, a polynucleotide may be contacted with at least one primer containing a desired sequence. In some embodiments, the primer may be, but not limited to, hybridized or annealed to the polynucleotide For example, the primer with the desired sequence (e.g., predetermined sequence) may be used to amplify the polynucleotide using an enzyme. For example, the enzyme may be a polymerase (e.g., a Taq polymerase). In some embodiments, the primer containing a predetermined sequence may be annealed or hybridized to the 3' end or the 5' end of the polynucleotide. In some embodiments, more than one pre-determined sequence may be annealed or hybridized to the polynucleotide. For example, a first pre-determined sequence may be annealed or hybridized to one end of the polynucleotide and a second pre-determined sequence may be annealed or hybridized to the other end of the polynucleotide. In some embodiments, the first pre-determined sequence may be complementary to the second pre-determined sequence. In some embodiments, the first pre-determined sequence may be reverse complementary to the second pre-determined sequence. In some embodiments, the first pre-determined sequence may not be complementary to the second pre-determined sequence.

In some embodiments, at least one oligonucleotide and at least one primer may be used to create a template from a polynucleotide such that the polynucleotide contains more than one pre-determined sequence. In some embodiments, only oligonucleotides may be used to create a template from a polynucleotide such that the polynucleotide contains more than one pre-determined sequence. In some embodiments, only primers may be used to create a template from a polynucleotide such that the polynucleotide contains more than one pre-determined sequence.

Efficiency and Accuracy

The methods described herein are accurate for creating an engineered template from a polynucleotide such that the polynucleotide portion of the engineered template does not contain any additional nucleotides that were not present in the sample from which the polynucleotide might be derived (e.g., white boxes in FIGS. 1A, 1B, 3A, and 3B). One exception includes the method illustrated in FIGS. 2A and 2B: where the polymerase may add extra adenosine to the 3' end as the polymerase is used after the restriction digestion and before the nick ligation of the adaptor oligonucleotides. In some embodiments, accuracy may refer to, but is not limited to a frame shift, at least one nucleotide deletion, at least one nucleotide insertion or at least one nucleotide substitution. In an exemplary embodiment, use of the methods described herein does not add any additional adenosine nucleotides at the end of any synthesized strands (e.g., second cDNA strand). For example, use of at least one oligonucleotide and at least one adaptor oligonucleotide in combination with a ligase (e.g., DNA ligase) to add at least one predetermined sequence to the polynucleotide following restriction digestion may result in an engineered template that is more accurate with respect to the original polynucleotide. The accuracy of the engineered template, created by use of the methods described herein, with respect to the polynucleotide is higher than other methods which do not use a ligase to generate the engineered template. In some embodiments, the accuracy may be at least 0.1, 0.2, 0.3, 0.4, 0.5, 0.6, 0.7, 0.8, 0.9, 1, 1.2, 1.4, 1.6, 1.8, 2.0, 2.2, 2.4, 2.6, 2.8, 3.0, 0.5, 4.0, 4.5, 5.0, 6, 6.5, 7, 7.5, 8, 8.5, 9, 9.5 or 10 times greater using the methods described herein. In a particular embodiment, the accuracy may be at least 1.0 times greater than other methods which do not use a ligase to generate the engineered template. In a particular embodiment, the accuracy may be at least 1.5 times greater than other methods which do not use a ligase to generate the engineered template. In a particular embodiment, the accuracy may be at least 2.0 times greater than other methods which do not use a ligase to generate the engineered template. In a particular embodiment, the accuracy may be at least 5.0 times greater than other methods which do not use a ligase to generate the engineered template. In a particular embodiment, the accuracy may be at least 10.0 times greater than other methods which do not use a ligase to generate the engineered template.

In some embodiments, the accuracy for creating an engineered template from a single sample of a polynucleotide is the same for any sequence of any chain or of any fragment. In some embodiments, the accuracy for creating an engineered template from a single sample of a polynucleotide is different for any sequence of any chain or of any fragment.

The methods described herein are efficient for creating an engineered template from a polynucleotide such that the polynucleotide portion of the engineered template does not contain any additional nucleotides that were not present in the sample from which the polynucleotide might be derived (e.g., white boxes in FIGS. 1A-3B). In some embodiments, efficiency may refer to, but is not limited to a frame shift, at least one nucleotide deletion, at least one nucleotide insertion or at least one nucleotide substitution. In an exemplary embodiment, use of the methods described herein does not add any additional adenosine nucleotides at the end of any synthesized strands (e.g., second cDNA strand). For example, use of at least one oligonucleotide and at least one adaptor oligonucleotide in combination with a ligase (e.g., DNA ligase) to add at least one predetermined sequence to the polynucleotide following restriction digestion may result in an engineered template that is more accurate with respect to the original polynucleotide as described above. The efficiency of the engineered template, created by use of the methods described herein, with respect to the polynucleotide is higher than other methods which do not use a ligase to generate the engineered template. In some embodiments, the efficiency may be at least 0.1, 0.2, 0.3, 0.4, 0.5, 0.6, 0.7, 0.8, 0.9, 1, 1.2, 1.4, 1.6, 1.8, 2.0, 2.2, 2.4, 2.6, 2.8, 3.0, 0.5, 4.0, 4.5, 5.0, 6, 6.5, 7, 7.5, 8, 8.5, 9, 9.5 or 10 times greater than methods which do not use a ligase to generate the engineered template. In a particular embodiment, the efficiency may be at least 1.0 times greater than methods which do not use a ligase to generate the engineered template. In a particular embodiment, the efficiency may be at least 1.5 times greater than methods which do not use a ligase to generate the engineered template. In a particular embodiment, the efficiency may be at least 1.7 times greater than methods which do not use a ligase to generate the engineered template. In a particular embodiment, the efficiency may be at least 2.0 times greater than methods which do not use a ligase to generate the engineered template. In a particular embodiment, the efficiency may be at least 2.10 times greater than methods which do not use a ligase to generate the engineered template. In a particular embodiment, the efficiency may be at least 5 times greater than methods which do not use a ligase to generate the engineered template. In a particular embodiment, the efficiency may be at least 10 times greater than methods which do not use a ligase to generate the engineered template.

In some embodiments, the efficiency for creating an engineered template from a single sample of a polynucleotide is the same for any sequence of any chain or of any fragment. In some embodiments, the efficiency for creating an engineered template from a single sample of a polynucleotide is different for any sequence of any chain or of any fragment.

Exemplary Methods

The engineered templates described in the described methods are meant to serve as exemplary applications of the methods described herein to create engineered templates. The engineered templates in these exemplary methods contain a first predetermined sequence in the first portion and a second predetermined sequence that is reverse-complement to the first predetermined sequence in a second portion. The engineered templates created herein may be utilized in a single primer amplification reaction. In exemplary embodiments, the single primer amplification reactions may use a primer that contains a portion of at least one of the predetermined sequences or the entire sequence of the predetermined sequence described herein.

Method 1

Preparation of gene-specific templates for single primer amplification by attaching at least one pre-determined sequence to the first strand cDNA.

This disclosure provides methods for creating an engineered template for single primer amplification, the method comprising: annealing an oligonucleotide containing a restriction site to a polynucleotide to create a polynucleotide with a double-stranded portion containing the restriction site; cleaving the double-stranded portion of the polynucleotide at the restriction site using a restriction endonuclease; removing fragments of the oligonucleotide of step (a) from the polynucleotide such that the cleaved polynucleotide does not contain any double-stranded portions thereby creating a polynucleotide with a cleavage at the 5' end; annealing a first adaptor oligonucleotide to the 5' end of the cleaved polynucleotide of step (c), the first adaptor oligonucleotide having a first portion that anneals to the 5' end of the cleaved polynucleotide and a second portion that anneals to a second adaptor oligonucleotide, the second adaptor oligonucleotide containing a first pre-determined sequence; ligating the 5' end of the cleaved polynucleotide to the second adaptor oligonucleotide thereby creating a pre-engineered template having the first pre-determined sequence at, or near, the 5' end; removing the first adaptor oligonucleotide from the pre-engineered template; annealing a set of primers to the pre-engineered template, at least one primer of the set of the primers having a portion containing a second pre-determined sequence; and synthesizing the engineered template such that the engineered template has the first pre-determined sequence at or near the 5' end and the second pre-determined sequence at, or near, the 3' end.

In some embodiments, this disclosure provides methods for creating engineered templates for the use in the single primer amplification of antibody genes. In some embodiments, the method includes the steps of: (a) synthesizing and hybridizing a first strand cDNA to an oligonucleotide such that the cDNA forms a double-stranded portion of DNA that may include a restriction site; (b) annealing a first oligonucleotide that is complementary to 5' end the first strand cDNA; (c) annealing the first oligonucleotide to the second oligonucleotide which may contain a predetermined sequence (FIG. 1A), or alternatively, (c) hybridizing the first oligonucleotide to the end of the cDNA and hybridizing the second oligonucleotide to a third oligonucleotide to form compatible overhangs such that a ligation reaction may be performed on both ends (FIG. 1B); (d) ligating (e.g., by nick ligation) the annealed polynucleotide and the second oligonucleotide in the presence of a DNA ligase, and; (e) annealing a primer to the engineered template.

In some embodiments, the primer may have a first portion with a predetermined sequence and a second portion that may anneal to the first stand cDNA and may be used to synthesize a second strand cDNA. In some embodiments, more than one primer may be used. For example, a set of primers may be used.

In some embodiments, the synthesized second strand cDNA may contain a first predetermined sequence in the first portion and a second predetermined sequence. In some embodiments, the second predetermined sequence may be a reverse-complement to the first predetermined sequence. The synthesized second strand cDNA may be a template for a single primer amplification reaction. For example, the single primer in the amplification reaction may contain a portion of, or the entire sequence of, the first or the first predetermined sequence. In some embodiments, the predetermined sequence is a universal sequence.

In some embodiments, more than one engineered template may be generated from at least one polynucleotide. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different.

In some embodiments, more than one engineered template may be combined into a single synthesis reaction. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different. In some embodiments, one primer may be used to amplify at least one engineered template within the single synthesis reaction. In some embodiments, more than one primer may be used to amplify at least one engineered template within the single synthesis reaction. For example, the engineered template may be amplified using at least one primer with a predetermined sequence reverse complementary to at least one pre-determined sequence of the engineered template. In some embodiments, the more than one primers used to amplify at least one engineered template within the single synthesis reaction may be different.

In some embodiments, this disclosure provides methods for creating an engineered template for single primer amplification, the method comprising: annealing an oligonucleotide containing a restriction site to a polynucleotide to create a polynucleotide with a double-stranded portion containing the restriction site; cleaving the double-stranded portion of the polynucleotide at the restriction site using a restriction endonuclease; removing fragments of the oligonucleotide of step (a) from the polynucleotide such that the cleaved polynucleotide does not contain any double-stranded portions thereby creating a polynucleotide with a cleavage at the 5' end; annealing a first adaptor oligonucleotide to the 5' end of the cleaved polynucleotide of step (c), and a second adapter oligonucleotide to a third adaptor oligonucleotide, the second adaptor oligonucleotide substantially complementary to the third adaptor oligonucleotide, the third adaptor oligonucleotide containing a first pre-determined sequence; ligating the 5' end of the cleaved polynucleotide to the third adaptor oligonucleotide thereby creating a pre-engineered template having the first pre-determined sequence at, or near, the 5' end; removing the first adaptor oligonucleotide from the pre-engineered template; annealing a set of primers to the pre-engineered template, at least one primer of the set of the primers having a second pre-determined sequence; and synthesizing the engineered template such that the engineered template has the first pre-determined sequence at, or near, the 5' end and the second pre-determined sequence at, or near, the 3' end.

Figure 1B:
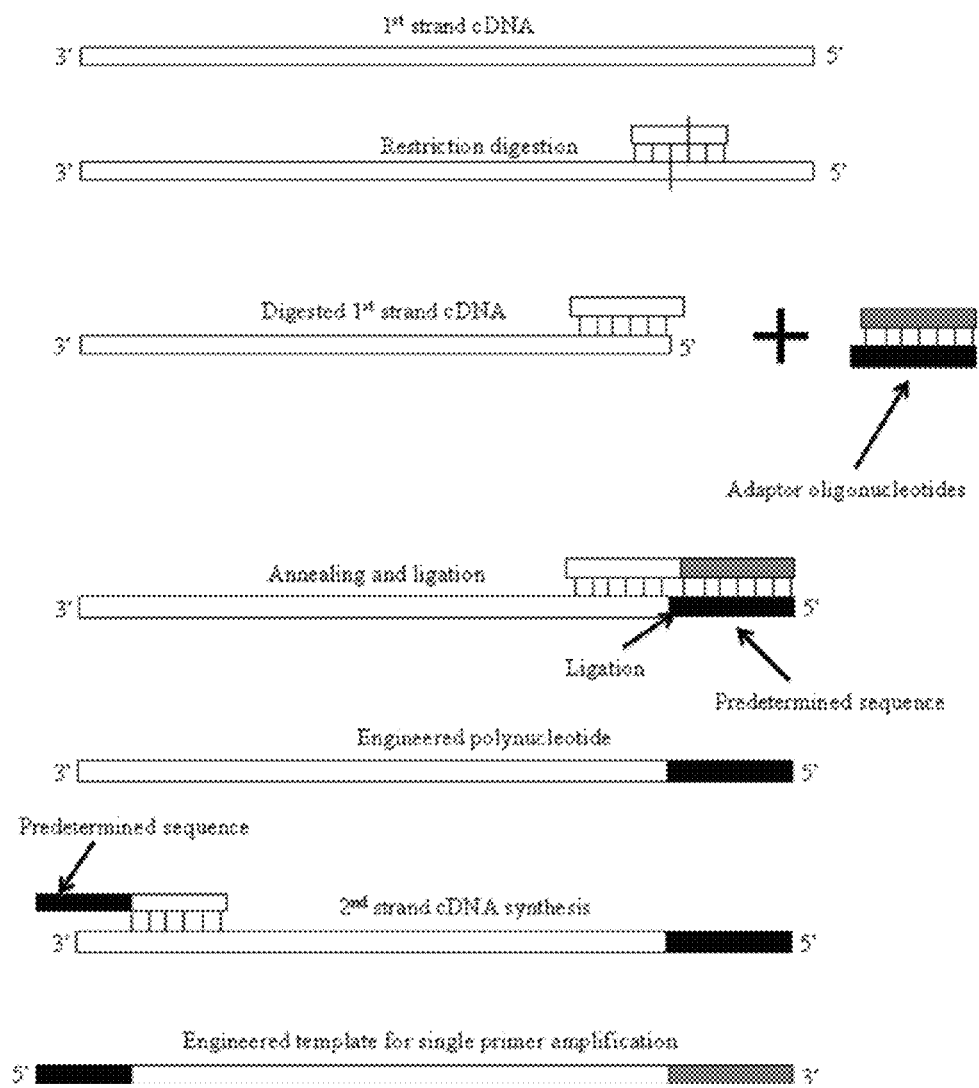
FIG. 1B is another exemplary embodiment of the invention where an engineered template for single primer amplification is created by at least attaching at least one pre-determined sequence to a first strand cDNA.

For example, FIG. 1A is an exemplary embodiment of the methods provided by the disclosure where an engineered template for single primer amplification is created using adaptor oligonucleotides and a series of annealing and ligation steps. Specifically:

(1) first strand cDNA may be synthesized with reverse transcriptase using random primers (e.g., oligo dT);

(2) an oligonucleotide may be annealed to the synthesized cDNA and digested with a restriction endonuclease;

(3) two adaptor oligonucleotides may be added to the digested cDNA. The first adaptor oligonucleotide can have a portion that anneals to the digested cDNA and another portion that can anneal to the second adaptor oligonucleotide;

(4) digested cDNA may be ligated to the second adaptor oligonucleotide in the presence of DNA ligase; and (5) a primer may be annealed to the ligated cDNA and the second strand cDNA might be synthesized.

In some embodiments, this disclosure provides methods for creating an engineered template for single primer amplification, the method comprising: annealing an oligonucleotide containing a restriction site to a polynucleotide to create a polynucleotide with a double-stranded portion containing the restriction site; cleaving the double-stranded portion of the polynucleotide at the restriction site using a restriction endonuclease; removing fragments of the oligonucleotide of step (a) from the polynucleotide such that the cleaved polynucleotide does not contain any double-stranded portions thereby creating a polynucleotide with a cleavage at the 5' end; annealing a first portion of a primer to the cleaved polynucleotide of step (c), the primer containing a second portion with a first pre-determined sequence; synthesizing a second polynucleotide having the first pre-determined sequence at, or near, a 5' end and a 3' end that contains the cleavage of step (c); annealing a first adaptor oligonucleotide to the to the 3' end of the second polynucleotide of step (e), the first adaptor oligonucleotide having a first portion that anneals to the 3' end of the second polynucleotide and a second portion that anneals to a second adaptor oligonucleotide, the second adaptor oligonucleotide containing a second pre-determined sequence, ligating the 3' end of the second polynucleotide to the second adaptor oligonucleotide thereby creating a pre-engineered template with the second pre-determined sequence at, or near, the 3' end; and removing the first adaptor oligonucleotide from the second polynucleotide to create an engineered template that has the first pre-determined sequence at, or near, the 5' end and the second pre-determined sequence at, or near, the 3' end.

In some embodiments, more than one engineered template may be generated from at least one polynucleotide. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different.

In some embodiments, more than one engineered template may be combined into a single synthesis reaction. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different. In some embodiments, one primer may be used to amplify at least one engineered template within the single synthesis reaction. In some embodiments, more than one primer may be used to amplify at least one engineered template within the single synthesis reaction. For example, the engineered template may be amplified using at least one primer with a pre-determined sequence reverse complementary to at least one pre-determined sequence of the engineered template. In some embodiments, the more than one primers used to amplify at least one engineered template within the single synthesis reaction may be different.

For example, FIG. 1B is an exemplary embodiment of the methods provided by the disclosure where an engineered template for single primer amplification is created using adaptor oligonucleotides and a series of annealing and ligation steps. Specifically:

(1) first strand cDNA may be synthesized with reverse transcriptase using random primers (e.g., oligo dT);

(2) an oligonucleotide may be annealed to the synthesized cDNA and digested with a restriction endonuclease;

(3) three adaptor oligonucleotides can be added to the digested cDNA. The first adaptor oligonucleotide may anneal to the digested cDNA and second and the third adaptor oligonucleotides may anneal to each other;

(4) digested cDNA annealed to the first adaptor oligonucleotide may form an overhang compatible with the overhang created by the other two adaptor oligonucleotides. These fragments may be ligated in the presence of DNA ligase; and (5) a primer may be annealed to the ligated cDNA and the second strand cDNA may be synthesized.

Method 2

Preparation of gene-specific templates for single primer amplification by attaching at least one pre-determined sequence to the second strand cDNA.

This disclosure provides methods for creating an engineered template for single primer amplification, the method comprising: annealing an oligonucleotide containing a restriction site to a polynucleotide to create a polynucleotide with a double-stranded portion containing the restriction site; cleaving the double-stranded portion of the polynucleotide at the restriction site using a restriction endonuclease; removing fragments of the oligonucleotide of step (a) from the polynucleotide such that the cleaved polynucleotide does not contain any double-stranded portions thereby creating a polynucleotide with a cleavage at the 5' end; annealing a first adaptor oligonucleotide to the 5' end of the cleaved polynucleotide of step (c), the first adaptor oligonucleotide having a first portion that anneals to the 5' end of the cleaved polynucleotide and a second portion that anneals to a second adaptor oligonucleotide, the second adaptor oligonucleotide containing a first pre-determined sequence; ligating the 5' end of the cleaved polynucleotide to the second adaptor oligonucleotide thereby creating a pre-engineered template having the first pre-determined sequence at, or near, the 5' end; removing the first adaptor oligonucleotide from the pre-engineered template; annealing a set of primers to the pre-engineered template, at least one primer of the set of the primers having a portion containing a second pre-determined sequence; and synthesizing the engineered template such that the engineered template has the first pre-determined sequence at or near the 5' end and the second pre-determined sequence at, or near, the 3' end.

In some embodiments, this disclosure provides methods for creating engineered templates for the use in the single primer amplification of antibody genes. In some embodiments, the method includes the steps of: (a) synthesizing a first strand cDNA and digesting the first strand cDNA with a restriction endonuclease in the presence of a hybridizing oligonucleotide that forms a double-stranded portion of DNA with the first strand cDNA such that the double-stranded portion includes a restriction site; (b) annealing a primer to the digested cDNA, the primer having a first portion with a predetermined sequence and a second portion that anneals to the first stand cDNA and using the primer to synthesize a second strand cDNA; (c) annealing a first oligonucleotide that may be complementary to the 3' end the synthesized second strand cDNA, the first oligonucleotide having a predetermined sequence that anneals to the second oligonucleotide (FIG. 2A); alternatively, the first oligonucleotide may be hybridized to the end of cDNA and the second oligonucleotide may be hybridized to the third oligonucleotide to form compatible overhangs for ligation for both ends (FIG. 2B); (d) ligating the annealed polynucleotide and the second oligonucleotide with a ligase (e.g., a DNA ligase). In some embodiments, the ligated second strand cDNA may contain a predetermined sequence in the first portion and a second predetermined sequence that may be a reverse-complement to the first portion at the end of the sequence.

In some embodiments, this disclosure provides methods of creating an engineered template for single primer amplification, the method comprising: (a) annealing an oligonucleotide containing a restriction site to a polynucleotide to create a polynucleotide with a double-stranded portion containing the restriction site; (b) cleaving the double-stranded portion of the polynucleotide at the restriction site using a restriction endonuclease; (c) removing fragments of the oligonucleotide of step (a) from the polynucleotide such that the cleaved polynucleotide does not contain any double-stranded portions thereby creating a polynucleotide with a cleavage at the 5' end; (d) annealing a first portion of a primer to the cleaved polynucleotide of step (c), the primer containing a second portion with a first pre-determined sequence; (e) synthesizing a second polynucleotide having the first pre-determined sequence at, or near, a 5' end and a 3' end that contains the cleavage of step (c); (f) annealing a first adaptor oligonucleotide to the to the 3' end of the second polynucleotide of step (e), the first adaptor oligonucleotide having a first portion that anneals to the 3' end of the second polynucleotide and a second portion that anneals to a second adaptor oligonucleotide, the second adaptor oligonucleotide containing a second pre-determined sequence, (g) ligating the 3' end of the second polynucleotide to the second adaptor oligonucleotide thereby creating a pre-engineered template with the second pre-determined sequence at, or near, the 3' end; and (h) removing the first adaptor oligonucleotide from the second polynucleotide to create an engineered template that has the first pre-determined sequence at, or near, the 5' end and the second pre-determined sequence at, or near, the 3' end.

In some embodiments, the primer may have a first portion with a predetermined sequence and a second portion that may anneal to the first stand cDNA and may be used to synthesize a second strand cDNA. In some embodiments, more than one primer may be used. For example, a set of primers may be used.

In some embodiments, the synthesized second strand cDNA may contain a first predetermined sequence in the first portion and a second predetermined sequence. In some embodiments, the second predetermined sequence may be a reverse-complement to the first predetermined sequence. The synthesized second strand cDNA may be a template for a single primer amplification reaction. For example, the single primer in the amplification reaction may contain a portion of or the entire sequence of the first or the first predetermined sequence. In some embodiments, the predetermined sequence is a universal sequence.

In some embodiments, more than one engineered template may be generated from at least one polynucleotide. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different.

In some embodiments, more than one engineered template may be combined into a single synthesis reaction. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different. In some embodiments, one primer may be used to amplify at least one engineered template within the single synthesis reaction. In some embodiments, more than one primer may be used to amplify at least one engineered template within the single synthesis reaction. For example, the engineered template may be amplified using at least one primer with a pre-determined sequence reverse complementary to at least one pre-determined sequence of the engineered template. In some embodiments, the more than one primers used to amplify at least one engineered template within the single synthesis reaction may be different.

Figure 2A:
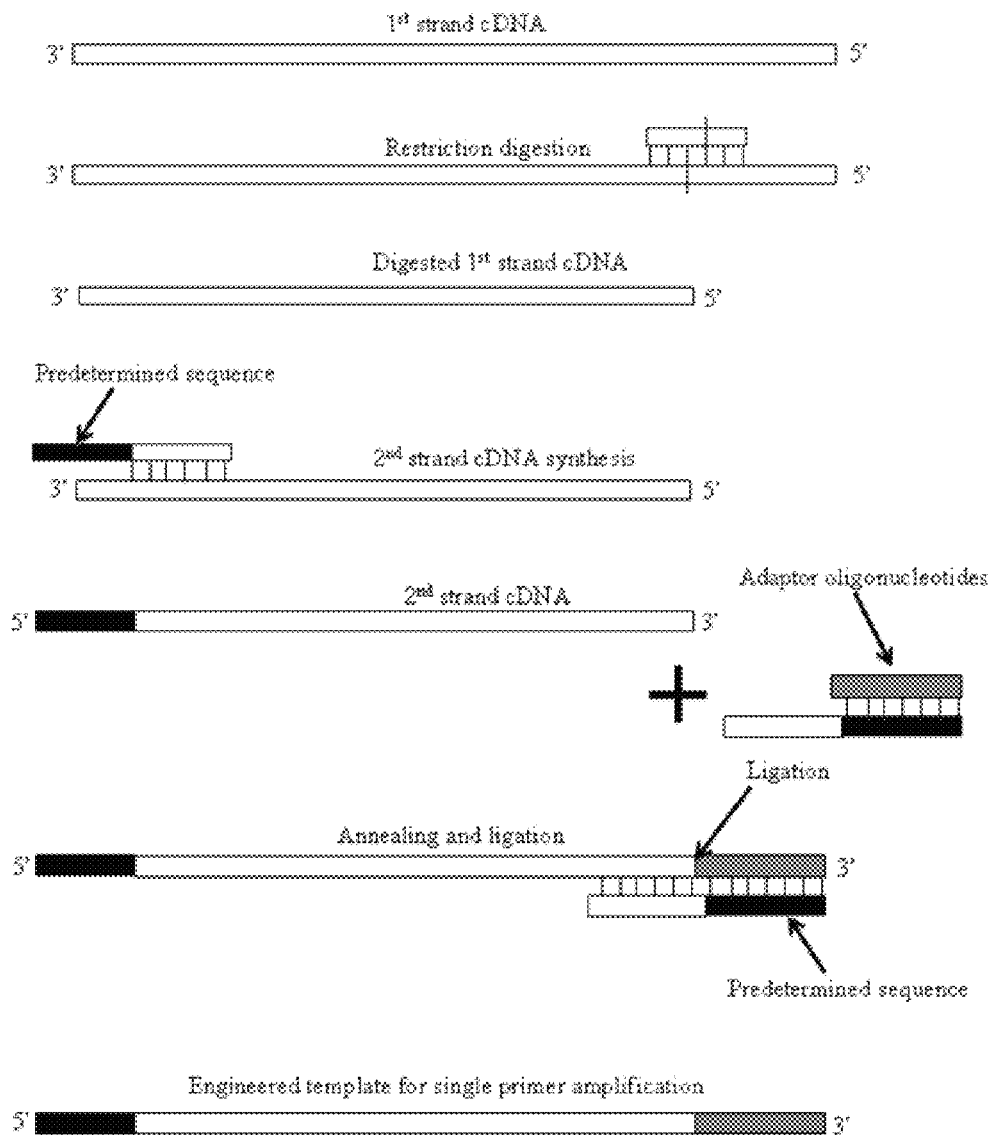
FIG. 2A is an exemplary embodiment of the invention where an engineered template for single primer amplification is created by at least attaching at least one pre-determined sequence to a second strand cDNA.
Figure 2B:
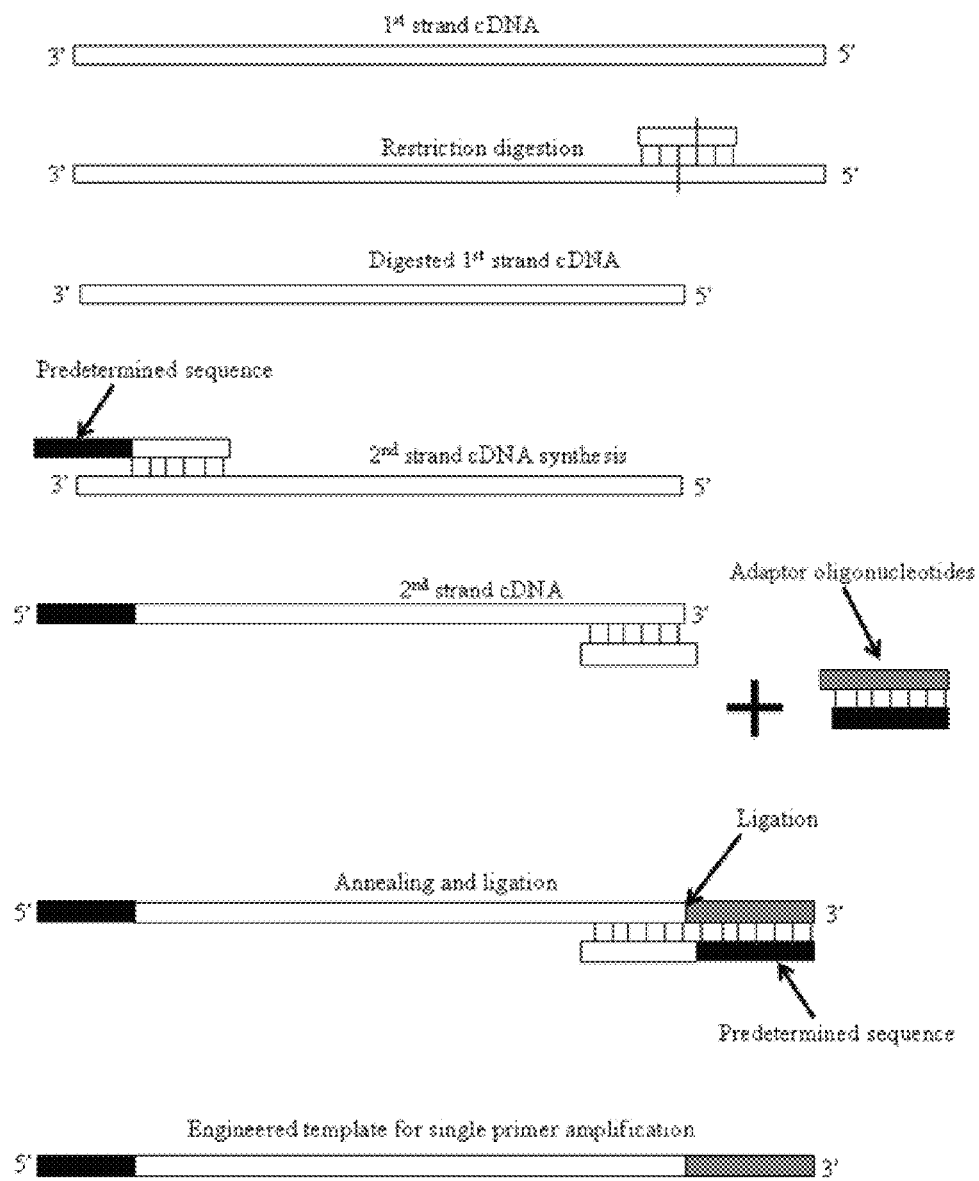
FIG. 2B is another exemplary embodiment of the invention where an engineered template for single primer amplification is created by at least attaching at least one pre-determined sequence to a second strand cDNA.

For example, FIG. 2A is an exemplary embodiment of the methods provided by the disclosure where an engineered template for single primer amplification is created using adaptor oligonucleotides and a series of annealing and ligation steps. Specifically:

(1) first strand cDNA may be synthesized with reverse transcriptase using random primers (e.g., oligo dT);

(2) an oligonucleotide may be annealed to the synthesized cDNA and digested with a restriction endonuclease;

(3) two adaptor oligonucleotides may be added to the synthesized first strand cDNA, the first adaptor oligonucleotide having a portion that anneals to the synthesized first strand cDNA and another portion that anneals to the second adaptor oligonucleotide;

(4) first strand cDNA may be ligated to the second adaptor oligonucleotide in the presence of DNA ligase; and (5) a primer may be annealed to the ligated cDNA and the second strand cDNA may be synthesized.

In some other embodiments, this disclosure provides methods of creating an engineered template for single primer amplification, the method comprising: (a) annealing an oligonucleotide containing a restriction site to a polynucleotide to create a polynucleotide with a double-stranded portion containing the restriction site; (b) cleaving the double-stranded portion of the polynucleotide at the restriction site using a restriction endonuclease; (c) removing fragments of the oligonucleotide of step (a) from the polynucleotide such that the cleaved polynucleotide does not contain any double-stranded portions thereby creating a polynucleotide with a cleavage at the 5' end; (d) annealing a first portion of a primer to the cleaved polynucleotide of step (c), the primer containing a second portion with a first pre-determined sequence; (e) synthesizing a second polynucleotide having the first pre-determined sequence at, or near, a 5' end and a 3' end that contains the cleavage of step (c); (f) annealing a first adaptor oligonucleotide to the 3' end of the second polynucleotide of step (e), and a second adapter oligonucleotide to a third adaptor oligonucleotide, the second adaptor oligonucleotide substantially complementary to the third adaptor oligonucleotide, the third adaptor oligonucleotide containing a second pre-determined sequence; (g) ligating the 3' end of the second polynucleotide to the third adaptor oligonucleotide thereby creating a pre-engineered template with the second pre-determined sequence at, or near, the 3' end; and (h) removing the first adaptor oligonucleotide from the second polynucleotide to create an engineered template that has the first pre-determined sequence at, or near, the 5' end and the second pre-determined sequence at, or near, the 3' end.

In some embodiments, more than one engineered template may be generated from at least one polynucleotide. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different.

In some embodiments, more than one engineered template may be combined into a single synthesis reaction. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different. In some embodiments, one primer may be used to amplify at least one engineered template within the single synthesis reaction. In some embodiments, more than one primer may be used to amplify at least one engineered template within the single synthesis reaction. For example, the engineered template may be amplified using at least one primer with a predetermined sequence reverse complementary to at least one pre-determined sequence of the engineered template. In some embodiments, the more than one primers used to amplify at least one engineered template within the single synthesis reaction may be different.

For example, FIG. 2B is an exemplary embodiment of the methods provided by the disclosure where an engineered template for single primer amplification is created using adaptor oligonucleotides and a series of annealing and ligation steps. Specifically:

(1) first strand cDNA may be synthesized with reverse transcriptase using random primers (e.g., oligo dT);

(2) an oligonucleotide may be annealed to the synthesized cDNA and digested with a restriction endonuclease;

(3) a primer may be annealed to the digested cDNA and the second strand cDNA may be synthesized;

(4) three adaptor oligonucleotides may be added to the synthesized second strand cDNA, the first adaptor oligonucleotide may anneal to the synthesized second strand cDNA and the second and the third adaptor oligonucleotides anneal to each other;

(5) the second strand cDNA may be annealed to the first adaptor oligonucleotide to form an overhang that may be compatible with the overhang that may be created by the other two adaptor oligonucleotides; and (6) these fragments may be ligated in the presence of DNA ligase.

Method 3

Preparation of gene-specific templates for single primer amplification by restriction digestion of the second strand cDNA.

In some embodiments, this disclosure provides methods for creating engineered templates for the use in the single primer amplification. In some embodiments, the method includes the steps of: annealing a set of primers to a first polynucleotide, the primers containing a first pre-determined sequence; synthesizing a second polynucleotide having the first pre-determined sequence at, or near, the 5' end; annealing an oligonucleotide containing a restriction site to the second polynucleotide to create a second polynucleotide with at least a double-stranded portion, the double-stranded portion containing the restriction site; cleaving the double-stranded portion of the second polynucleotide at the restriction site using a restriction endonuclease; removing fragments of the oligonucleotide of step (c) from the second polynucleotide such that the cleaved polynucleotide does not contain any double-stranded portions thereby creating a second polynucleotide with a cleavage at the 3' end; annealing a first adaptor oligonucleotide to the to the 3' end of the second polynucleotide of step (e), the first adaptor oligonucleotide having a first portion that anneals to the 3' end of the second polynucleotide and a second portion that anneals to a second adaptor oligonucleotide, the second adaptor oligonucleotide containing a second pre-determined sequence, ligating the 3' end of the cleaved polynucleotide to the second adaptor oligonucleotide thereby creating a pre-engineered template with the second pre-determined sequence at, or near, the 3' end; and removing the first adaptor oligonucleotide from the second polynucleotide to create an engineered template that has the first pre-determined sequence at, or near, the 5' end and the second pre-determined sequence at, or near, the 3' end.

In some embodiments, this disclosure provides methods for creating engineered templates for the use in the single primer amplification of antibody genes. In some embodiments, the method includes the steps of: annealing a set of primers to a first polynucleotide, the primers containing a first pre-determined sequence; synthesizing a second polynucleotide having the first pre-determined sequence at, or near, the 5' end; annealing an oligonucleotide containing a restriction site to the second polynucleotide to create a second polynucleotide with at least a double-stranded portion, the double-stranded portion containing the restriction site; cleaving the double-stranded portion of the second polynucleotide at the restriction site using a restriction endonuclease; removing fragments of the oligonucleotide of step (c) from the second polynucleotide such that the cleaved polynucleotide does not contain any double-stranded portions thereby creating a second polynucleotide with a cleavage at the 3' end; annealing a first adaptor oligonucleotide to the to the 3' end of the second polynucleotide of step (e), the first adaptor oligonucleotide having a first portion that anneals to the 3' end of the second polynucleotide and a second portion that anneals to a second adaptor oligonucleotide, the second adaptor oligonucleotide containing a second pre-determined sequence, ligating the 3' end of the cleaved polynucleotide to the second adaptor oligonucleotide thereby creating a pre-engineered template with the second pre-determined sequence at, or near, the 3' end; and removing the first adaptor oligonucleotide from the second polynucleotide to create an engineered template that has the first pre-determined sequence at, or near, the 5' end and the second pre-determined sequence at, or near, the 3' end.

In some embodiments, the primer may have a first portion with a predetermined sequence and a second portion that may anneal to the first stand cDNA and may be used to synthesize a second strand cDNA. In some embodiments, more than one primer may be used. For example, a set of primers may be used.

In some embodiments, the synthesized second strand cDNA may contain a first predetermined sequence in the first portion and a second predetermined sequence. In some embodiments, the second predetermined sequence may be a reverse-complement to the first predetermined sequence. The synthesized second strand cDNA may be a template for a single primer amplification reaction. For example, the single primer in the amplification reaction may contain a portion of or the entire sequence of the first or the first predetermined sequence. In some embodiments, the predetermined sequence is a universal sequence.

In some embodiments, more than one engineered template may be generated from at least one polynucleotide. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different.

In some embodiments, more than one engineered template may be combined into a single synthesis reaction. In some embodiments, the engineered templates may be the same. In some embodiments, the engineered templates may be different. In some embodiments, at least one predetermined sequence located within the more than one engineered templates may be the same. In some embodiments, at least one predetermined sequence located within the more than one engineered templates may be different. In some embodiments, one primer may be used to amplify at least one engineered template within the single synthesis reaction. In some embodiments, more than one primer may be used to amplify at least one engineered template within the single synthesis reaction. For example, the engineered template may be amplified using at least one primer with a pre-determined sequence reverse complementary to at least one pre-determined sequence of the engineered template. In some embodiments, the more than one primers used to amplify at least one engineered template within the single synthesis reaction may be different.

Figure 3A:
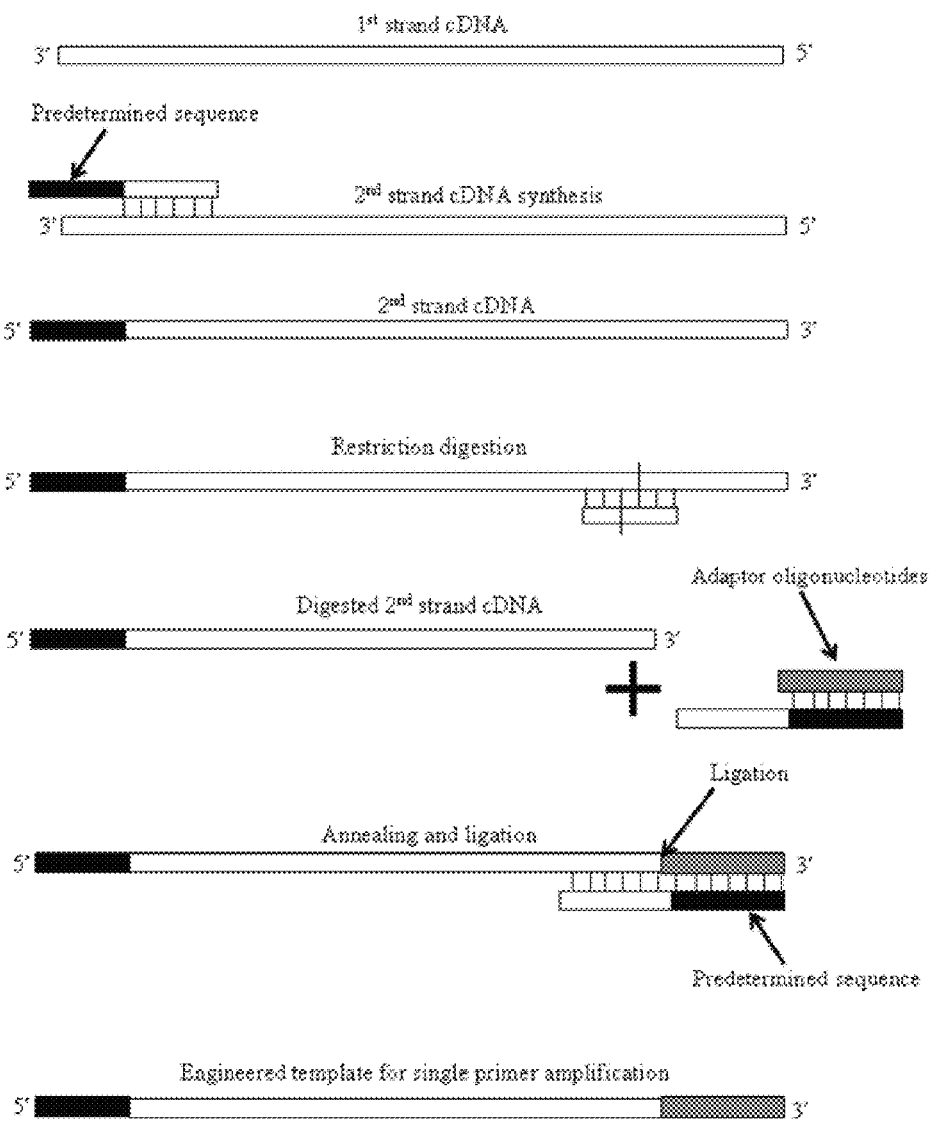
FIG. 3A is an exemplary embodiment of the invention where an engineered template for single primer amplification is created by at least restriction digestion of a second strand cDNA.

For example, FIG. 3A is an exemplary embodiment of the methods provided by the disclosure where an engineered template for single primer amplification is created using adaptor oligonucleotides and a series of annealing and ligation steps. Specifically:

(1) first strand cDNA may be synthesized with reverse transcriptase using random primers (e.g., oligo dT);

(2) a primer may be annealed to the first strand cDNA and the second strand cDNA may be synthesized;

(3) an oligonucleotide may be annealed to the synthesized cDNA and may be digested with a restriction endonuclease;

(4) two adaptor oligonucleotides may be added to the digested second strand cDNA, the first adaptor oligonucleotide may have a portion that anneals to the digested second strand cDNA and another portion that anneals to a second adaptor oligonucleotide; and (5) second strand cDNA may be ligated to the second adaptor oligonucleotide in the presence of DNA ligase.

A method of creating an engineered template for single primer amplification, the method comprising: annealing a set of primers to a first polynucleotide, the primers containing a first pre-determined sequence; synthesizing a second polynucleotide having the first pre-determined sequence at, or near, the 5' end; annealing an oligonucleotide containing a restriction site to the second polynucleotide to create a second polynucleotide with at least a double-stranded portion, the double-stranded portion containing the restriction site; cleaving the double-stranded portion of the second polynucleotide at the restriction site using a restriction endonuclease; removing fragments of the oligonucleotide of step (c) from the second polynucleotide such that the cleaved polynucleotide does not contain any double-stranded portions thereby creating a second polynucleotide with a cleavage at the 3' end; annealing a first adaptor oligonucleotide to the 3' end of the second polynucleotide of step (e), and a second adapter oligonucleotide to a third adaptor oligonucleotide, the second adaptor oligonucleotide substantially complementary to the third adaptor oligonucleotide, the third adaptor oligonucleotide containing a second pre-determined sequence; ligating the 3' end of the second polynucleotide to the second adaptor oligonucleotide to create a pre-engineered template with the second pre-determined sequence at, or near, the 3' end; and removing the first adaptor oligonucleotide from the second polynucleotide to create an engineered template that has the first pre-determined sequence at, or near, the 5' end and the second pre-determined sequence at, or near, the 3' end.

Figure 3B:
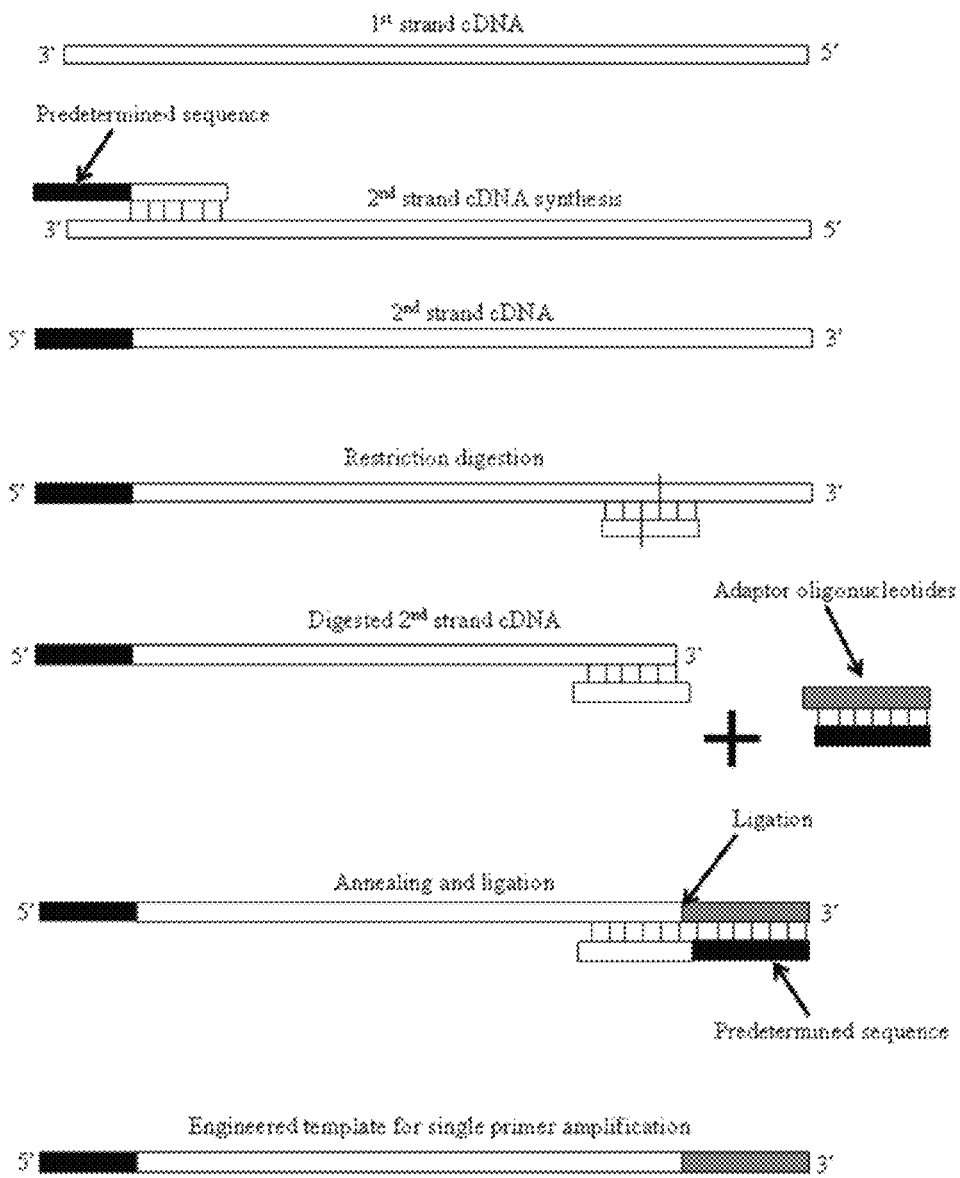
FIG. 3B is another exemplary embodiment of the invention where an engineered template for single primer amplification is created by at least restriction digestion of a second strand cDNA.

For example, FIG. 3B is an exemplary embodiment of the methods provided by the disclosure where an engineered template for single primer amplification is created using adaptor oligonucleotides and a series of annealing and ligation steps. Specifically:

(1) first strand cDNA may be synthesized with reverse transcriptase using random primers (e.g., oligo dT);

(2) a primer may be annealed to the first strand cDNA and the second strand cDNA may be synthesized;

(3) an oligonucleotide may be annealed to the synthesized cDNA and digested with a restriction endonuclease;

(4) three adaptor oligonucleotides may be added to the digested second strand cDNA, the first adaptor oligonucleotide may anneal to the digested second strand cDNA and second and the third adaptor oligonucleotides anneal to each other;

(5) annealing the second strand cDNA to the first adaptor oligonucleotide may form an overhang that may be compatible with the overhang created by the other two adaptor oligonucleotides; and (6) these fragments may be ligated in the presence of DNA ligase.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

EXAMPLES

Example 1

Generation of Engineered Templates for Kappa Light Chain and IgG1 from Polynucleotides Derived from the Spleens of Mice Immunized Against CD80 and CD86

Two BALB/c mice were immunized with recombinant CD80/Fc and CD86/Fc as shown below in Table 1. Spleen were taken out on day 57 and homogenized in 5 mL of TRI-reagent (Molecular Research Center, Cincinnati, Ohio).

TABLE 1

Immunization at Promab

|  | 1st imm/ 1st Tail blood draw | 2nd Tail blood draw | 2nd imm | 3rd Tail blood draw | 3rd imm | 4th Tail blood draw | 4th imm | 5th Tail blood draw | 5th imm | spleen extraction |
|---|---|---|---|---|---|---|---|---|---|---|
| adjuvant | CFA |  |  | IFA |  | IFA |  | No adjuvant |  |  |
| Antigen (µg) | 100 µg |  |  | 100 µg |  | 100 µg |  | 50 µg |  |  |
| inject site | SC |  |  | SC |  | SC |  | iv |  |  |
| inject day | 1 | 8 | 15 | 22 | 29 | 36 | 43 | 50 | 57 |  |
| Date | 2.1 | 2.8 | 2.15 | 2.22 | 3.1 | 3.8 | 3.15 | 3.22 | 3.29 |  |

ELISA Testing Serum Titers.

Microtiter wells (Costar 3690) were coated with 50 µL of CD80/Fc, CD86/Fc, or HER2/Fc at 1 µg/mL in PBS at 4° C. overnight. Wells were washed 3 times with PBS and blocked with 100 µL of 1% BSA/PBS at 37° C. for 1 hr. Blocker was discarded and the wells were incubated with 50 µL of mouse sera serially diluted in PBS at 37° C. for 1.5 hrs.

Figure 4:
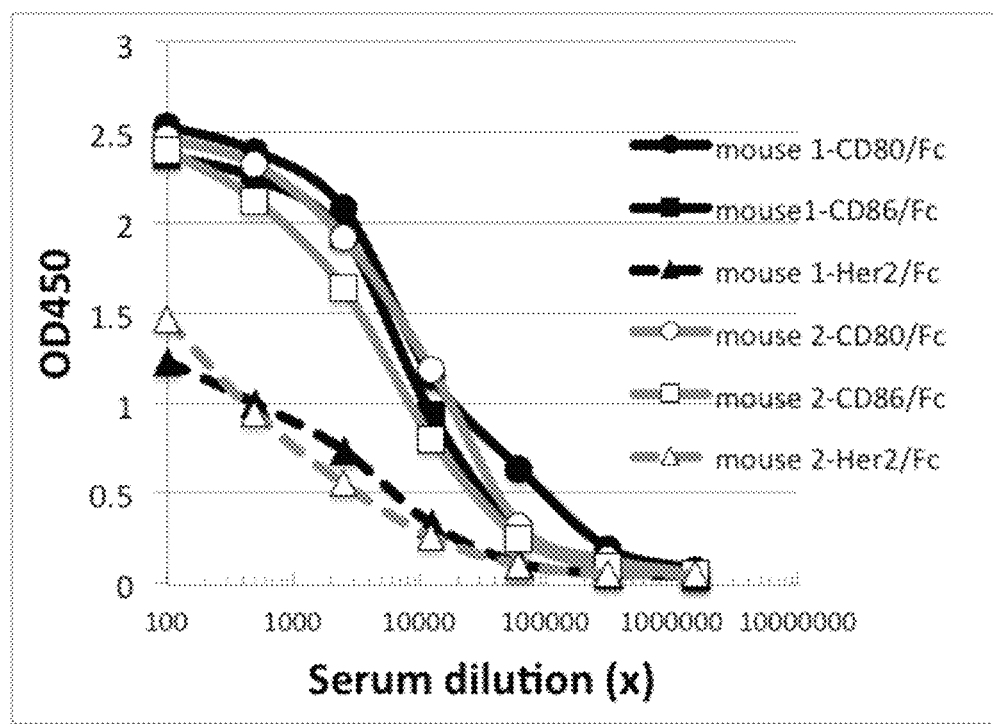
FIG. 4 is a graph of mouse serum reactivity to CD80 and CD86 as determined using an ELISA assay.

Wells were washed 3 times with PBS and bound antibodies were detected with peroxidase-conjugated goat anti-mouse IgG F(ab')$_2$ antibody (Pierce Biotechnology Rockford, Ill. 31436) (1:5000 in 1% BSA/PBS) at 37° C. for 1 hour (hr). The wells were washed 3 times with PBS and developed with 50 µL of TMB substrate mixture (Pierce Biotechnology 34021). The reaction was stopped with 50 µL of 2N sulfuric acid and signal was read at 450 nm (FIG. 4). ELISA reactivity of mouse sera against CD80 and CD86. Sera from immunized mice (day 50) were tested for their reactivity to corresponding antigens by ELISA. Both mice showed strong reactivity to CD80/Fc and CD86/Fc but not to a control antigen Her2/Fc.

Total RNA Isolation from Spleen Cells in TRI Reagent.

Total RNA was isolated from homogenized spleen according to conventional methods using a commercially available kit using the manufacturer's protocol.

Phase Separation.

The lysed sample was thawed and stored for 5 minutes at room temperature to permit the complete dissociation of nucleoprotein complexes. Next, the lysate was supplemented with 0.1 ml BCP (bromochloropropane) (Molecular Research Center) per 1 ml of TRI reagent, the samples were covered tightly and shaken vigorously for 15 seconds. The resulting mixture was stored at room temperature for 2-5 minutes and centrifuged at 12,000 g for 15 minutes at 4° C.

RNA Precipitation.

The aqueous phase was transferred to a fresh tube. RNA was precipitated from the aqueous phase by mixing with isopropanol. 0.5 ml of isopropanol was added per 1 ml of tri reagent used for the initial lysis. Samples were stored at room temperature for 5-10 min and centrifuged at 12,000 g for 8 minutes at 4° C.

RNA Wash.

The supernatant was removed and 1 ml of 75% ethanol was added per 1 ml of TRI reagent. The RNA suspension was centrifuged at 7,500 g for 5 minutes at 25° C. The supernatant was decanted and re-spun briefly. The remaining supernatant was aspirated completely from the RNA pellet.

RNA Solubilization.

Figure 5:
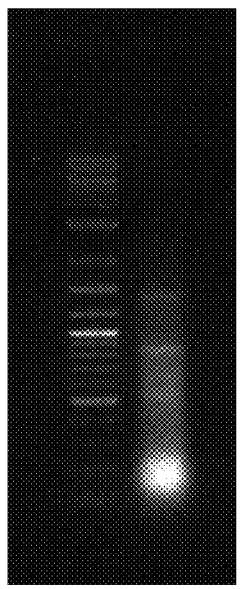
FIG. 5 is an image of a diagnostic agarose gel demonstrating the purity of RNA isolated from homogenized mouse spleen using TRI reagent.

The RNA pellet was briefly air-dried for 5 min. RNA was dissolved in 250 µl RNase-free water by passing the solution through a pipette tip and incubating for 15 minutes at 55° C. One µL of total RNA was run on 1% agarose gel (FIG. 5).

TABLE 2

Total RNA Characterization

|  | OD260 | OD280 | OD320 | OD260/ 280 | Concentration (ng/µL) | Total (µg/µL) |
|---|---|---|---|---|---|---|
| Total RNA | 2.782 | 1.124 | 0.016 | 2.496 | 5331.7 | 1,366/250 |

Messenger RNA (Poly A+) Purification.

mRNA was purified using Oligotex (QIAGEN) according to the manufacturer's manual. Oligotex Suspension was heated to 37° C. in a water bath, mixed by vortex, and placed at RT. Buffer OBB was re-dissolved in 37° C. water bath, and place at RT. RNase-free water (included in the kit) was added to 500 µL (~1 mg total RNA). Five-hundred µL Buffer OBB and 55 µL Oligotex suspension were added and mixed by flicking the tube. The mixture was incubated at 70° C. for 3 min, removed from the heating block, and placed at RT for 10 min. The Oligotex:RNA complex was pelleted by centrifugation for 2 min at maximum speed, and the supernatant was carefully removed by pipetting. The Oligotex:RNA pellet was re-suspended in 400 µL Buffer OW2 by vortex, and pipetted onto a small spin column placed in a 1.5 ml micro-centrifuge tube, and centrifuged for 1 min at maximum speed. The spin column was transferred to a new RNase-free 1.5 mL micro-centrifuge tube, 400 µL Buffer OW2 was applied to the column, centrifuged for 1 min at maximum speed, and the flow-through was discarded. The spin column was transferred to a new RNase-free 1.5 mL microcentrifuge tube, 50 µL of hot (70° C.) Buffer OEB was pipetted onto the column placed on the heat block, pipetted up and down to re-suspend the resin, and centrifuged for 1 min at maximum speed. Another 50 µL hot (70° C.) Buffer OEB was added to the column placed on the heat block, re-suspended resin completely, and centrifuged for 1 min at maximum speed.

TABLE 3

RNA Characterization Following Purification

|  | OD260 | OD280 | OD320 | OD260/280 | Concentration (ng/μL) | Total (μg/μL) |
|---|---|---|---|---|---|---|
| mRNA | 0.866 | 0.439 | 0.094 | 2.239 | 30.894 | 3.1/100 |

First Strand cDNA Synthesis.

First strand cDNA was synthesized according to the manufacturer's protocol. (Invitrogen life technologies SuperScript III First-Strand Synthesis System for RT-PCR). Five hundred (500) ng of mRNA was mixed with 5 μL of dNTP (10 mM each) and 5 μL of oligo $(dT)_{20}$ primer (SEQ ID NO: 1), and water was added to 50 μL. The mixture was incubated at 65° C. for 5 min and immediately transferred on ice for more than 1 min. Ten μL of 10×RT buffer, 20 μL of 25 mM $MgCl_2$, 10 μL of 0.1 M DTT, 5 μL of RNase OUT inhibitor, and 5 μL of SuperScript RTase III were added to the reaction and incubated at 50° C. for 50 min, at 85° C. for 15 min, and cooled to 4° C. Then, 5 μL of RNase H was added and incubated at 37° C. for 20 min, at 95° C. for 1 min.

Preparation of Template for Single Primer Amplification.

Digestion of $1^{st}$ strand cDNA with a restriction oligonucleotide. Seventeen μL of $1^{st}$ strand cDNA was mixed with 1 μL of restriction oligonucleotide (20 μM) (see table below) (Operon, HPLC purified) (final 1 μM) and 2 μL of 10× NEBuffer (New England BioLabs Ipswich, Mass.) and incubated at 95° C. for 2 min, 64° C. for 2 min, and cooled down to 37° C. Then, restriction endonuclease (see table below) were added and incubated at 37° C. for 1 hr, 65° C. for 20 min, and cooled down to 4° C.

TABLE 4

Restriction Digestion Conditions

|  | Kappa | IgG1 |
|---|---|---|
| Restriction oligonucleotide | mCKHpaI | mCG1XcmI |
| 10× NEBuffer | NEBuffer 4 | NEBuffer 2 |
| Restriction endonuclease | 1 μL HpaI (5 U/μL) (NEB) (R0105S) | 2 μL XcmI (5 U/μL) (NEB) (R0533S) |

Adaptor Oligonucleotide Hybridization and Nick Ligation.

Twenty μL of digested $1^{st}$ strand cDNA was mixed with 22.5 μL of water, 1 μL of Adaptor oligo 1 (20 μM), 1 μL of Adaptor oligo 2 (20 μM), 5 μL of 10× Taq DNA Ligase Reaction Buffer, and 0.5 μL of Taq DNA Ligase (40 U/μL) and incubated at 95° C. for 2 min, 65° C. for 2 min, and 45° C. for 1 hr.

TABLE 5

Adaptor Types and Sequences

|  | Kappa | IgG1 |
|---|---|---|
| Adapter 1 | mCKAd1: CTCTCTCCATCTTCCCACCATCC AGTGAGCAGTTGACATCCGGAC ACTCCTCTTGGTAGCCGGTCGTC (SEQ ID NO: 2) | mCG1Ad1: CCCTGGATCTGCTGCCCAAACTA ACTCCATGGTCACTCCTCTTCCA ACGGCCACGTC (SEQ ID NO: 3) |
| Adapter 2 | mCKAd2: GACGACCGGCTACCAAGAGGAG TGTCCGGATGTC (SEQ ID NO: 4) | mCG1Ad2: GACGTGGCCGTTGGAAGAGGAG TG (SEQ ID NO: 5) |

2nd Stand cDNA Synthesis.

For the synthesis of $2^{nd}$ strand cDNA for kappa light chains, 33.5 μL of ligated cDNA was added to 536 μL of water, 67 μL of 10× Reaction Buffer, 13.4 μL of dNTP (10 mM each), 6.7 μL of AmpliTaq (Life Technologies, Carlsbad, Calif.) and mixed. Forty-nine μL of mixture was added to 13 wells of PCR reaction tubes and 1 μL of each 5' TMX24 mVK primer was added separately. The reaction was denatured at 94° C. for 1 min first and $2^{nd}$ strand synthesis was performed by 20 cycles of denaturation at 94° C. for 5 seconds, annealing at 56° C. for 10 seconds, and extension at 68° C. for 2 min.

For the synthesis of $2^{nd}$ strand cDNA for IgG1 heavy chains, 33.5 μL of ligated cDNA was added to 536 μL of water, 67 μL of 10× Reaction Buffer, 13.4 μL of dNTP (10 mM each), 6.7 μL of AmpliTaq (Life Technologies, Carlsbad, Calif.) and mixed. Forty-nine μL of mixture was added to 13 wells of PCR reaction tubes and 1 μL of each 5' TMX24 mVH primer was added separately. The reaction was denatured at 94° C. for 1 min first and $2^{nd}$ strand synthesis was performed by 20 cycles of denaturation at 94° C. for 5 seconds, annealing at 56° C. for 10 seconds, and extension at 68° C. for 2 min.

TABLE 6

Kappa Framework 1 Specific Primers.
(R = A + G, M = A + C, K = G + T, W = A + T, S = C + G)

| Primer | Sequence | Length |
|---|---|---|
| TMX24-mVK1 | GACGACCGGCTACCAAGAGGAGTGTCTAGAGACAT TGTGATGWCACAGTCTC (SEQ ID NO: 6) | 52 |
| TMX24-mVK2 | GACGACCGGCTACCAAGAGGAGTGTCTAGAGATGT TKTGATGACCCARACTC (SEQ ID NO: 7) | 52 |
| TMX24-mVK3 | GACGACCGGCTACCAAGAGGAGTGTCTAGAGACAT TGTGATGACKCAGGCTG (SEQ ID NO: 8) | 52 |
| TMX24-mVK4 | GACGACCGGCTACCAAGAGGAGTGTCTAGAGACAW TGTGCTGACCCARTCTC (SEQ ID NO: 9) | 52 |
| TMX24-mVK5 | GACGACCGGCTACCAAGAGGAGTGTCTAGAGAAAW TGTGCTCACCCAGTCTC (SEQ ID NO: 10) | 52 |
| TMX24-mVK6 | GACGACCGGCTACCAAGAGGAGTGTCTAGAGACAT CCAGATGACMCAGTCTC (SEQ ID NO: 11) | 52 |
| TMX24-mVK7 | GACGACCGGCTACCAAGAGGAGTGTCTAGAGATAT CCAGATGACACAGACTAC (SEQ ID NO: 12) | 53 |
| TMX24-mVK8 | GACGACCGGCTACCAAGAGGAGTGTCTAGAGACAT TGTSATGACCCAGTC (SEQ ID NO: 13) | 50 |

TABLE 6-continued

Kappa Framework 1 Specific Primers.
(R = A + G, M = A + C, K = G + T, W = A + T, S = C + G)

| Primer | Sequence | Length |
|---|---|---|
| TMX24-mVK9 | GACGACCGGCTACCAAGAGGAGTGTCTAGACAAATTGTTCTCACCCAGTCTC (SEQ ID NO: 14) | 52 |
| TMX24-mVK10 | GACGACCGGCTACCAAGAGGAGTGTCTAGAGACATCKTGCTSACTCAGTCTC (SEQ ID NO: 15) | 52 |
| TMX24-mVK11 | GACGACCGGCTACCAAGAGGAGTGTCTAGAGATATTGTGATAACCCAGGATG (SEQ ID NO: 16) | 52 |
| TMX24-mVK12 | GACGACCGGCTACCAAGAGGAGTGTCTAGAAGYATTGTGATGACCCAGWCTC (SEQ ID NO: 17) | 52 |
| TMX24-mVK13 | GACGACCGGCTACCAAGAGGAGTGTCTAGAGACATCCAGATGACACAATCTTC (SEQ ID NO: 18) | 53 |

TABLE 7

Heavy Chain Framework 1 Specific Primers.
(R = A + G, M = A + C, Y = C + T, S = C + G)

| Primer | Sequence | Length |
|---|---|---|
| TMX24-mVH1 | GACGTGGCCGTTGGAAGAGGAGTGCTCGAGGTGCAGCTTCAGSAGTC (SEQ ID NO: 19) | 47 |
| TMX24-mVH2 | GACGTGGCCGTTGGAAGAGGAGTGCTCGAGGTGCAGCTGAAGSAGTC (SEQ ID NO: 20) | 47 |
| TMX24-mVH3 | GACGTGGCCGTTGGAAGAGGAGTGCTCGAGGTCCAGCTGCAACAGTTTG (SEQ ID NO: 21) | 49 |
| TMX24-mVH4 | GACGTGGCCGTTGGAAGAGGAGTGCTCGAGGTYCAGCTGCARCARTC (SEQ ID NO: 22) | 47 |
| TMX24-mVH5 | GACGTGGCCGTTGGAAGAGGAGTGCTCGAGGTCCAACTGCAGCAGYC (SEQ ID NO: 23) | 47 |
| TMX24-mVH6 | GACGTGGCCGTTGGAAGAGGAGTGCTCGAGGTTCAGCTGCAGCAGTC (SEQ ID NO: 24) | 47 |
| TMX24-mVH7 | GACGTGGCCGTTGGAAGAGGAGTGCTCGAGGTGAAGCTGGTGGAGWC (SEQ ID NO: 25) | 47 |
| TMX24-mVH8 | GACGTGGCCGTTGGAAGAGGAGTGCTCGAGGTGAAGCTTCTGGAGTC (SEQ ID NO: 26) | 47 |
| TMX24-mVH9 | GACGTGGCCGTTGGAAGAGGAGTGCTCGAGGTGMAGCTGGTGGAGTC (SEQ ID NO: 27) | 47 |
| TMX24-mVH10 | GACGTGGCCGTTGGAAGAGGAGTGCTCGAGGTGAAGCTTCTgGAGTCTGG (SEQ ID NO: 28) | 50 |
| TMX24-mVH11 | GACGTGGCCGTTGGAAGAGGAGTGCTCGAGGTGAAGCTTGAGGAGTC (SEQ ID NO: 29) | 47 |
| TMX24-mVH12 | GACGTGGCCGTTGGAAGAGGAGTGCTCGAGGTTACTCTGAAAGAGTC (SEQ ID NO: 30) | 47 |
| TMX24-mVH13 | GACGTGGCCGTTGGAAGAGGAGTGCTCGAGATCCAGTTGGTGCAGTC (SEQ ID NO: 31) | 47 |

Clean Up 2nd Strand cDNA.

Second stand cDNA was cleaned using NucleoSpin 8 PCR Clean Up Core Kit (Macherey-Nagel, Düren, Germany). To each cDNA reaction, 250 μL of Buffer PB (×5 volume) and 7.5 μL of 3M NaOAc pH 5.2 (1:40 volume after addition of Buffer PB) were added and mixed 3 times with 8 channel multi-channel pipetter.

Then, the mixture was added to 8-well columns and vacuumed at −200~−400 mbar to drain. Columns were washed with 1000 μL of Buffer PE, sit at RT for 2 minutes (min), and vacuumed at maximum pressure. Columns were washed with another 1000 μL of Buffer PE and vacuumed at maximum pressure. Columns were taken out and dried on paper towel. Waste tray was emptied, columns were put back, and vacuumed at maximum pressure for 10 min.

cDNA was eluted with 100 μL of Buffer EB, sit at room temperature (RT) for 1 min, and vacuumed at maximum pressure for 1 min for each column to collect onto microplate.

Single Primer Amplification.

For the amplification of kappa light chain by single primer amplification (Advantage 2 polymerase mix, Clontech, Mountain View, Calif.), master reaction mixture was made first by mixing 2094.4 μL of water, 280 μL of 10× buffer, 56 μL of dNTP (10 mM each), 33.6 μL of TMX24mK primer (100 μM), and 56 μL of Advantage 2 polymerase mix. Twenty-seven of 90 μL of aliquots were made and 10 μL of each $2^{nd}$ strand cDNA was added (two reaction tubes for each) or 10 μL of water to a blank control tube. The reaction was denatured at 95° C. for 1 min first and single primer amplification was performed by 30 cycles of denaturation at 95° C. for 5 seconds and annealing and extension at 72° C. for 30 seconds, followed by final extension at 72° C. for 3 min.

For the amplification of IgG1 heavy chain by single primer amplification, master reaction mixture was made first by mixing 2094.4 μL of water, 280 μL of 10× buffer, 56 μL of dNTP (10 mM each), 33.6 μL of TMX24 mH primer (100 μM), and 56 μL of Advantage 2 polymerase mix. Twenty-seven of 90 μL of aliquots were made and 10 μL of each $2^{nd}$ strand cDNA was added (two reaction tubes for each) or 10 μL of water to a blank control tube. The reaction was denatured at 95° C. for 1 min first and single primer amplification was performed by 30 cycles of denaturation at 95° C. for 5 seconds and annealing and extension at 72° C. for 30 seconds, followed by final extension at 72° C. for 3 min.

TABLE 8

Primers for Single Primer Amplification

| Primer | Sequence | Length |
|---|---|---|
| TMX24mH | GACGTGGCCGTTGGAAGAGGAGTG (SEQ ID NO: 32) | 24 |
| TMX24mK | GACGACCGGCTACCAAGAGGAGTG (SEQ ID NO: 33) | 24 |

Figure 6:
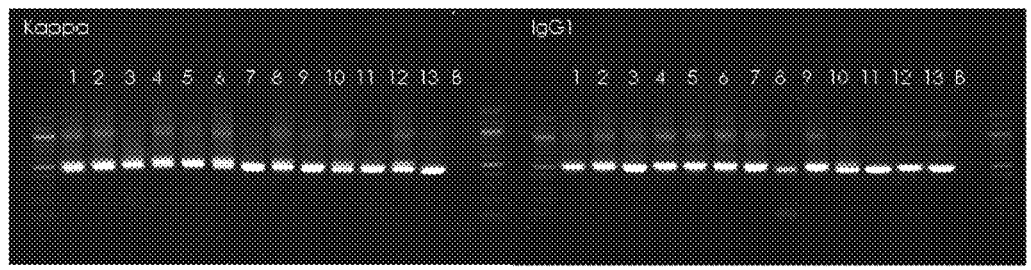
FIG. 6 is two images of a diagnostic agarose gel (Kappa chain, left; IgG1, right) demonstrating the results of single primer amplification using the methods described herein.

Five μL of amplified products were run on 1.5% agarose gels to check with 1 μg of 100 bp ladder marker (New England BioLabs). See, FIG. 6, which depicts the products of single primer amplification.

Example 2

Generation of Engineered Templates for Kappa Light Chain and IgG1 from Polynucleotides Derived from the Spleens of Mice Immunized Against Two Unique Peptides Two BALB/c mice were immunized with peptide 1 (cHTGFLpTEpYVATRW) (SEQ ID NO: 34) or peptide 2 (cDPEHDHTGFLpTEpYVA) (SEQ ID NO: 35), where p denotes phosphorylated site and c denotes free cysteine.

Antigen Preparation (Reconstitution in Water).

Antigen1:86828#1 free peptide (cHTGFLpTEpY-VATRW) (SEQ ID NO: 34) 4.0 mg/1 mL H$_2$O. Antigen1N: 86828#1N free peptide (HTGFLTEYVATRW) (SEQ ID NO: 36) 4.0 mg/1 mL H$_2$O. Antigen2:86828#2 free peptide (cDPEHDHTGFLpTEpYVA) (SEQ ID NO: 35) 4.0 mg/1 mL H$_2$O. Antigen2N:86828#2N free peptide (cDPEHDHTGFLTEYVA) (SEQ ID NO: 37) 4.0 mg/1 mL H$_2$O. Twenty (20) µL aliquots each, stored at −20° C.

Microtiter plates (Costar 3690) were coated with 50 µL of each peptide in PBS at 5 µg/mL at 4° C. overnight. Wells were washed 3 times with PBS and blocked with 100 µL of 1% BSA/PBS at 37° C. for 1 hr. Fifty µL of serially diluted sera (1:100, 1:500, 1:2500, 1:12500, 1:62500 in 1% BSA/PBS) was added to the wells and incubated at 37° C. for 1 hr.

Wells were washed 3 times with PBS and detected with 50 µL of HRP Goat anti-Rabbit IgG (H+L) Cross Adsorbed Secondary Antibody, HRP conjugate (Pierce Biotechnology 31462) (1:5,000 in 1% BSA/PBS) at 37° C. for 1 hr. Wells were washed 3 times with PBS and developed with 50 µL of TMB substrate mixture (Pierce Biotechnology 34021). 50 µL of 2N sulfuric acid was added and read at 450 nm.

Figure 7A:
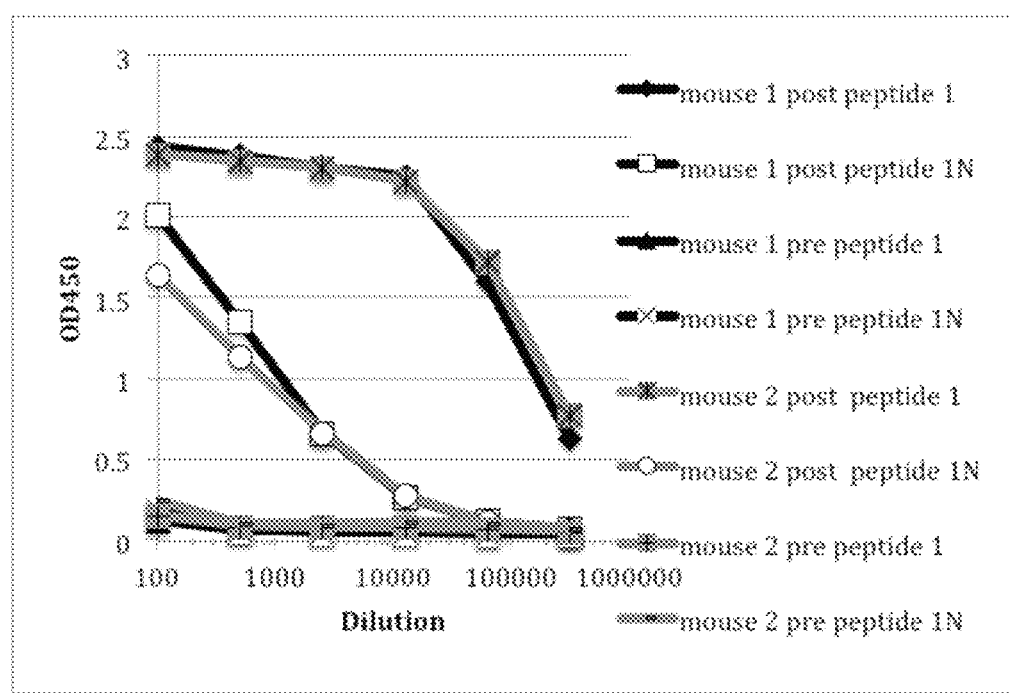
FIG. 7A is a graph indicating reactivity of mouse sera to four different peptides prior to, and following, immunization.
Figure 7B:
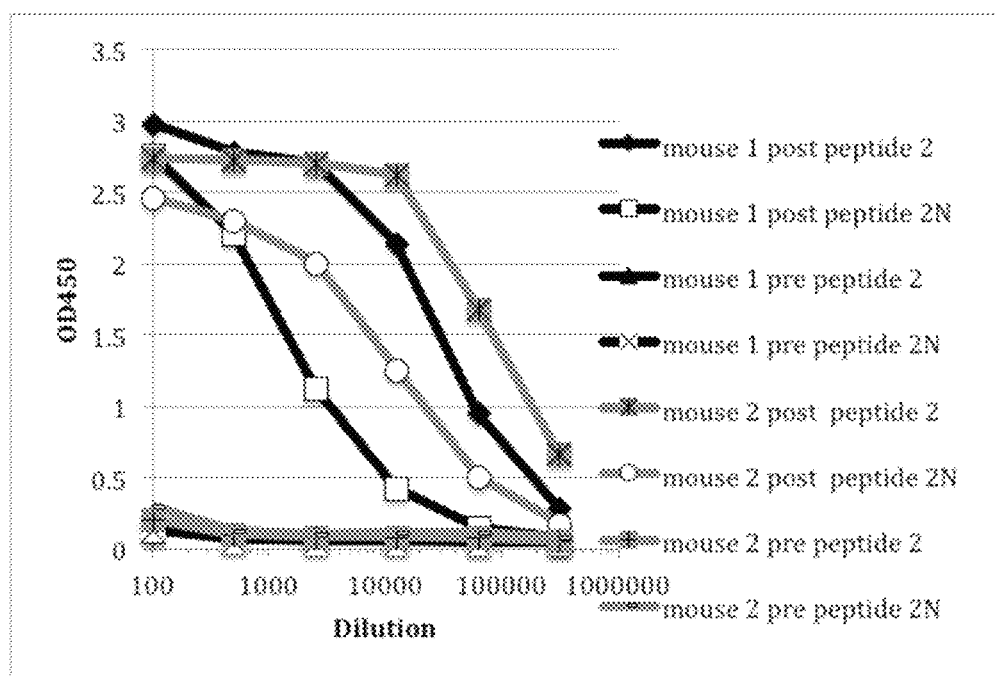
FIG. 7B is a graph indicating reactivity of mouse sera to four different peptides prior to, and following, immunization.

See, FIGS. 7A and 7B which depict Peptide Binding Curves.

Total RNA Isolation from Spleen Cells.

Spleen cells were homogenized in 8 mL TRI reagent (1 mL per 50-100 mg tissue). Total RNA was isolated from homogenized spleen according to the manufacturer's protocol in TRI reagent.

Phase Separation.

The lysed samples (ERK#1 mouse 2 and ERK#2 mouse 2) were thawed and stored for 5 minutes at room temperature to permit the complete dissociation of nucleoprotein complexes. Next, the lysate was supplemented with 0.1 mL BCP per 1 mL of TRI Reagent, the samples were covered tightly and shaken vigorously for 15 seconds. The resulting mixture was stored at room temperature for 2-5 minutes and centrifuged at 12,000 g for 15 minutes at 4° C.

RNA Precipitation.

The aqueous phase was transferred to a fresh tube. RNA was precipitated from the aqueous phase by mixing with isopropanol. 0.5 mL of isopropanol was added per 1 mL of TRI Reagent used for the initial lysis. Samples were stored at room temperature for 5-10 min and centrifuged at 12,000 g for 8 minutes at 4° C.

RNA Wash.

The supernatant was removed and 1 mL of 75% ethanol was added per 1 mL of TRI Reagent. The RNA suspension was centrifuged at 7,500 g for 5 minutes at 25° C. The supernatant was decanted and re-spun briefly. The remaining supernatant was aspirated completely from the RNA pellet.

RNA Solubilization.

The RNA pellet was briefly air-dried for 5 min. RNA was dissolved in 250 µL RNase-free water by passing the solution through a pipette tip and incubating for 15 minutes at 55° C. One µL of total RNA was run on 1% agarose gel.

TABLE 9

RNA Characterization Following Solubilization

| Total RNA | OD260 | OD280 | OD320 | OD260/280 | Concentration (ng/µL) | Total (µg/µL) |
|---|---|---|---|---|---|---|
| ERK#1 | 2.764 | 1.377 | 0.013 | 2.079 | 5501.5 | 1084/197 |
| ERK#2 | 2.360 | 1.041 | 0.010 | 2.280 | 4700.8 | 926/197 |

Figure 8:
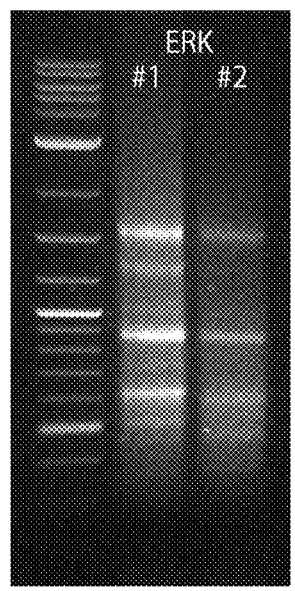
FIG. 8 is an image of a diagnostic agarose gel demonstrating the purity of RNA isolated from homogenized mouse (ERK mouse) spleen using Tri reagent.

FIG. 8 depicts RNA Purity obtained following solubilization.

Messenger RNA (Poly A+) Purification.

mRNA was purified using Oligotex (QIAGEN) according to the manufacturer's manual. Oligotex Suspension was heated to 37° C. in a water bath, mixed by vortex, and placed at RT. Buffer OBB was re-dissolved in 37° C. water bath, and place at RT. RNase-free water (included in the kit) was added to 500 µL (~1 mg total RNA). Five-hundred µL Buffer OBB and 55 µL Oligotex suspension were added and mixed by flicking the tube. The mixture was incubated at 70° C. for 3 min, removed from the heating block, and placed at RT for 10 min. The Oligotex:RNA complex was pelleted by centrifugation for 2 min at maximum speed, and the supernatant was carefully removed by pipetting. The Oligotex:RNA pellet was re-suspended in 400 µL Buffer OW2 by vortex, and pipetted onto a small spin column placed in a 1.5 ml micro-centrifuge tube, and centrifuged for 1 min at maximum speed. The spin column was transferred to a new RNase-free 1.5 mL micro-centrifuge tube, 400 µL Buffer OW2 was applied to the column, centrifuged for 1 min at maximum speed, and the flow-through was discarded. The spin column was transferred to a new RNase-free 1.5 mL microcentrifuge tube, 50 µL of hot (70° C.) Buffer OEB was pipetted onto the column placed on the heat block, pipetted up and down to re-suspend the resin, and centrifuged for 1 min at maximum speed. Another 50 µL hot (70° C.) Buffer OEB was added to the column placed on the heat block, re-suspended resin completely, and centrifuged for 1 min at maximum speed.

TABLE 10

RNA Characterization Following Solubilization

| mRNA | OD260 | OD280 | OD320 | OD260/280 | Concentration (ng/µL) | Total (µg/µL) |
|---|---|---|---|---|---|---|
| ERK#1 | 0.773 | 0.342 | 0.005 | 2.278 | 30.743 | 2.76/90 |
| ERK#2 | 0.585 | 0.252 | 0.005 | 2.300 | 23.584 | 2.12/90 |

First Strand cDNA Synthesis.

First strand cDNA was synthesized according to the manufacturer's protocol (ProtoScript II First Strand cDNA Synthesis Kit, New England Biolabs E6560L). Two-hundred-fifty ng of mRNA was mixed with 5 µL of d(T)$_{23}$ VN and water was added to 20 µL. The mixture was incubated at 65° C. for 5 min and immediately transferred on ice for more than 1 min. Twenty-five µL of ProtoScript II Reaction Mix (2×) and 5 µL of Protoscript II Enzyme Mix (10×) were added to the reaction and incubated at 42° C. for 60 min, at 80° C. for 5 min, and cooled to 4° C.

Preparation of Template for Single Primer Amplification. Digestion of 1st Strand cDNA with a Restriction Oligonucleotide.

For the digestion of kappa cDNA, 17 µL of 1$^{st}$ strand cDNA was mixed with 1 µL of restriction oligonucleotide rKRe (20 µM) (see table below) (Operon, HPLC purified) (final 1 µM) and 2 µL of 10× CutSmart Buffer (New England BioLabs) and incubated at 95° C. for 2 min, 64° C. for 2 min, and cooled down to 37° C. Then, 1 µL of restriction endonuclease DdeI (10 U/µL) (New England Biolabs) (R0175S) was added and incubated at 37° C. for 1 hr, 65° C. for 20 min, and cooled down to 4° C.

TABLE 11

Parameters of First Oligonucleotide for Restriction Digestion

| | | | |
|---|---|---|---|
| rKRe | TACCTACARCCTSAGCAGYACTCTG (SEQ ID NO: 38) | HPLC 50 nmol | 20 pmol/µL |

For the digestion of IgG cDNA, 17 µL of 1$^{st}$ strand cDNA was mixed with 1 µL of restriction oligonucleotide rCGRe (20 µM) (see table below) (Operon, HPLC purified) (final 1 µM) and 2 µL of 10×NEB3.1 (New England BioLabs) and incubated at 95° C. for 2 min and cooled down to 65° C. Then, 1 µL of restriction endonuclease BsrI (5 U/µL) (New England Biolabs) (R0527S) was added and incubated at 65° C. for 1 hr, 80° C. for 20 min, and cooled down to 4° C.

TABLE 12

Parameters of Second Oligonucleotide for Restriction Digestion

| | | | |
|---|---|---|---|
| rCGRe | CCTCCCSGAGCCAGTGACCGTGACTTG (SEQ ID NO: 39) | HPLC 50 nmol | 20 pmol/µL |

S = C or G

Adaptor Oligonucleotide Hybridization and Nick Ligation.

Twenty µL of DdeI-digested 1$^{st}$ strand cDNA was mixed with 22.5 µL of water, 2 µL of rCK Adaptor oligo mix (20 µM), 5 µL of 10× Taq DNA Ligase Reaction Buffer, and 0.5 µL of Taq DNA Ligase (40 U/µL) and incubated at 95° C. for 2 min, 65° C. for 2 min, and 45° C. for 1 hr.

TABLE 13

Adaptors for Oligonucleotide Hybridization of DdeI digested cDNA

| Adaptor oligo mix | rCK Ad mix |
|---|---|
| Adapter 1 | rCKAd1 mix (rCK1-1Ad1, rCK1-2Ad1, rCK1-3Ad1, rCK1-4Ad1, rCK2Ad1) (1:1:1:1:1) |
| Adapter 2 | rCK1Ad2 |

TABLE 14

Sequence of Adaptors for Oligonucleotide Hybridization of DdeI digested cDNA.

| | |
|---|---|
| rCK1-1Ad1 | CGCAGAATTCTGCAGATTGTACCTACAACCTCAcGTCGAC-CACTCC TCTTGGTAGCCGGTCGTC (SEQ ID NO: 40) |
| rCK1-2Ad1 | CRCAGAATTCTGATGATTGTACCTACAACCTCAcGTCGAC-CACTCC TCTTGGTAGCCGGTCGTC (SEQ ID NO: 41) |
| rCK1-3Ad1 | CGCAGAGCCCCGAAGACTGTACCTACAACCTCAcGTCGAC-CACTCC TCTTGGTAGCCGGTCGTC (SEQ ID NO: 42) |
| rCK1-4Ad1 | CGCAGGATCCTACATATTGTACCTACAACCTCAcGTCGAC-CACTCC TCTTGGTAGCCGGTCGTC (SEQ ID NO: 43) |
| rCK2-Ad1 | CGCAGAGCCCYGAAGACAATACCTACAGCCTCAcGTCGACCACTC CTCTTGGTAGCCGGTCGTC (SEQ ID NO: 44) |
| rCK1-Ad2 | GACGACCGGCTACCAAGAGGAGTGGTCGACG (SEQ ID NO: 45) |

Twenty µL of BsrI-digested 1$^{st}$ strand cDNA was mixed with 22.5 µL of water, 2 µL of rCG Adaptor oligo mix (20 µM), 5 µL of 10× Taq DNA Ligase Reaction Buffer, and 0.5 µL of Taq DNA Ligase (40 U/µL) and incubated at 95° C. for 2 min, 65° C. for 2 min, and 45° C. for 1 hr.

TABLE 15

Adaptors for Oligonucleotide Hybridization of BsrI digested cDNA

| Adaptor oligo mix | rCG Ad mix |
|---|---|
| Adapter 1 | rCG1/4Ad1:rCG2/5Ad1 (1:1) |
| Adapter 2 | rCGAd2 |

TABLE 16

Sequence of Adaptors for Oligonucleotide Hybridization of BsrI digested cDNA.

| | |
|---|---|
| rCG1/4Ad1 | GCTGCTTGGTCAAAGGCTACCTCCCCGAaCCgGTCACTCCTCTTCCA ACGGCCACGTC (SEQ ID NO: 46) |
| rCG2/5Ad1 | GCTGCcTGGTCAAAGGCTACCTCCCGGAaCCgGTCACTCCTCTTCCA ACGGCCACGTC (SEQ ID NO: 47) |
| rCGAd2 | GACGTGGCCGTTGGAAGAGGAGTGACcGGt (SEQ ID NO: 48) |

2nd Stand cDNA Synthesis.

For the synthesis of $2^{nd}$ strand cDNA for kappa light chains, 20 μL of ligated cDNA was added to 320 μL of water, 40 μL of 10× Reaction Buffer, 8 μL of dNTP (10 mM each), 8 μL of TMXrVK primer mix (20 μM), 4 μL of AmpliTaq (Life Technologies, Carlsbad, Calif.) and mixed. 100 μL of mixture was added to 4 wells of PCR reaction tubes. The reaction was denatured at 94° C. for 1 min first and $2^{nd}$ strand synthesis was performed by 20 cycles of denaturation at 94° C. for 5 seconds, annealing at 56° C. for 10 seconds, and extension at 68° C. for 2 min.

For the synthesis of $2^{nd}$ strand cDNA for IgG heavy chains, 20 μL of ligated cDNA was added to 320 μL of water, 40 μL of 10× Reaction Buffer, 8 μL of dNTP (10 mM each), 8 μL of TMXrVH primer mix (20 μM), 4 μL of AmpliTaq (Life Technologies, Carlsbad, Calif.) and mixed. 100 μL of mixture was added to 4 wells of PCR reaction tubes. The reaction was denatured at 94° C. for 1 min first and $2^{nd}$ strand synthesis was performed by 20 cycles of denaturation at 94° C. for 5 seconds, annealing at 56° C. for 10 seconds, and extension at 68° C. for 2 min.

TABLE 17

Rabbit kappa chain framework 1 specific primers:
(equal amount of
each primer was mixed and used as TMX24rVK primer mix)

| | | |
|---|---|---|
| TMX24rVK1 | GACGACCGGCTACCAAGAGGAGTGTCTAGA GACATTGTGCTGACCCAG (SEQ ID NO: 49) | 50 nmol, HPLC, 20 μM |
| TMX24rVK2 | GACGACCGGCTACCAAGAGGAGTGTCTAGA GACCCTRTGMTGACCCAG (SEQ ID NO: 50) | 50 nmol, HPLC, 20 μM |
| TMX24rVK3 | GACGACCGGCTACCAAGAGGAGTGTCTAGA GATGKYGTGATGACCCAG (SEQ ID NO: 51) | 50 nmol, HPLC, 20 μM |
| TMX24rVK4 | GACGACCGGCTACCAAGAGGAGTGTCTAGA GCAGCCGTGMTGACCCAG (SEQ ID NO: 52) | 50 nmol, HPLC, 20 μM |
| TMX24rVK5 | GACGACCGGCTACCAAGAGGAGTGTCTAGA GCCATCRAAATGACCCAG (SEQ ID NO: 53) | 50 nmol, HPLC, 20 μM |
| TMX24rVK6 | GACGACCGGCTACCAAGAGGAGTGTCTAGA GCYCAAGKGMTGACCCAG (SEQ ID NO: 54) | 50 nmol, HPLC, 20 μM |
| TMX24rVK7 | GACGACCGGCTACCAAGAGGAGTGTCTAGA GCSCTSGTGMTGACCCAG (SEQ ID NO: 55) | 50 nmol, HPLC, 20 μM |
| TMX24rVK8 | GACGACCGGCTACCAAGAGGAGTGTCTAGA TATGTCATGATGACCCAG (SEQ ID NO: 56) | 50 nmol, HPLC, 20 μM |

TABLE 18

Rabbit heavy chain framework 1 specific primers (equal amount of
each primer was mixed and used as TMX24rVH primer mix)

| | | |
|---|---|---|
| TMX24rVH1a | GACGTGGCCGTTGGAAGAGGAGTGCTCG AGCAGGAGCAGCTGAAGGAGtc (SEQ ID NO: 57) | 50 nmol, HPLC, 20 μM |
| TMX24rVH2d | GACGTGGCCGTTGGAAGAGGAGTGCTCG AGCAGTCAGTGAAGGAGTCCga (SEQ ID NO: 58) | 50 nmol, HPLC, 20 μM |
| TMX24rVH3L | GACGTGGCCGTTGGAAGAGGAGTGCTCG AGCAGTCGCTGGRGGAGTCCrg (SEQ ID NO: 59) | 50 nmol, HPLC, 20 μM |
| TMX24rVH3b | GACGTGGCCGTTGGAAGAGGAGTGCTCG AGCAGTCGYTGGgGGAGTCCrg (SEQ ID NO: 60) | 50 nmol, HPLC, 20 μM |
| TMX24rVH4L | GACGTGGCCGTTGGAAGAGGAGTGCTCG AGCAGTCGKTGGAGGAGTCCrg (SEQ ID NO: 61) | 50 nmol, HPLC, 20 μM |
| TMX24rVH4a | GACGTGGCCGTTGGAAGAGGAGTGCTCG AGCAGTCGgTGGAGGAGTCCrg (SEQ ID NO: 62) | 50 nmol, HPLC, 20 μM |
| TMX24rVH7L | GACGTGGCCGTTGGAAGAGGAGTGCTCG AGCAGWCRGTGAAGGAGTCCga (SEQ ID NO: 63) | 50 nmol, HPLC, 20 μM |

TABLE 18-continued

Rabbit heavy chain framework 1 specific primers (equal amount of each primer was mixed and used as TMX24rVH primer mix)

| | | |
|---|---|---|
| TMX24rVH8L | GACGTGGCCGTTGGAAGAGGAGTGCTCG AGCAGTCGCTGGAGGAATTCgg (SEQ ID NO: 64) | 50 nmol, HPLC, 20 µM |

(K = G + T, M = A + C, R = A + G, S = C + G, W = A + T, Y = C + T)

Clean Up 2nd Strand cDNA Using PCR Purification Columns.

Second stand cDNA was cleaned using 2 PCR purification columns. cDNA reaction was pooled (400 mL) and 2 mL of Buffer PB (×5 volume) and 60 µL of 3M NaOAc pH 5.2 (1:40 volume after addition of Buffer PB) were added and mixed pipetting. Then, the mixture was added to 2 PCR columns and vacuumed at −200~−400 mbar to drain. Columns were washed with 700 µL of Buffer PE, sit at RT for 2 min, and vacuumed at maximum pressure. Columns were washed with another 700 µL of Buffer PE and vacuumed at maximum pressure. Columns were spun at maximum speed for 2.5 min and residual buffer was aspirated. DNA was eluted with 100 µL of Buffer EB, sit at RT for 1 min, and columns were spun at maximum speed for 1.5 min.

Single Primer Amplification.

For the amplification of kappa light chain by single primer amplification (Advantage 2 polymerase mix, Clontech), master reaction mixture was made first by mixing 987.6 µL of water, 120 µL of 10× buffer, 24 µL of dNTP (10 mM each), 30 µL of $2^{nd}$ strand cDNA, 14.4 µL of TMX24mK primer (100 µM), and 24 µL of Advantage 2 polymerase mix. Twelve aliquots of 100 µL of reactions were made. Blank control was set separately by mixing 85.8 µL of water, 10 µL of 10× buffer, 2 µL of dNTP (10 mM each), 1.2 µL of TMX24mK primer (100 µM), and 2 µL of Advantage 2 polymerase mix. The reaction was denatured at 95° C. for 1 min first and single primer amplification was performed by 30 cycles of denaturation at 95° C. for 5 seconds and annealing and extension at 72° C. for 30 seconds, followed by final extension at 72° C. for 3 min.

For the amplification of IgG heavy chain by single primer amplification, master reaction mixture was made first by mixing 987.6 µL of water, 120 µL of 10× buffer, 24 µL of dNTP (10 mM each), 30 µL of a second strand cDNA, 14.4 µL of TMX24 mH primer (100 µM), and 24 µL of Advantage 2 polymerase mix. Twelve aliquots of 100 µL of reactions were made. Blank control was set separately by mixing 85.8 µL of water, 10 µL of 10× buffer, 2 µL of dNTP (10 mM each), 1.2 µL of TMX24 mH primer (100 µM), and 2 µL of Advantage 2 polymerase mix. The reaction was denatured at 95° C. for 1 min first and single primer amplification was performed by 30 cycles of denaturation at 95° C. for 5 seconds and annealing and extension at 72° C. for 30 seconds, followed by final extension at 72° C. for 3 min.

Figure 9:
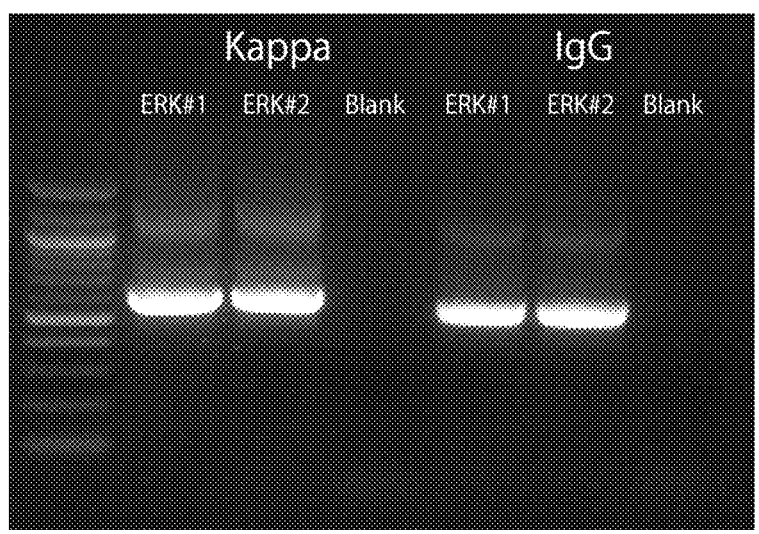
FIG. 9 is an image of a diagnostic agarose gel (Kappa chain, left; IgG1, right) demonstrating the results of single primer amplification using methods described herein.

Ten µL of amplified products were run on 1.5% agarose gels to check with 1 µg of 100 bp ladder marker (New England Biolabs). See, FIG. 9.

Example 3

Additional Sequences that May be Used in the Described Methods

Mouse
Oligonucleotides for Restriction Endonuclease Digestion

| | | | |
|---|---|---|---|
| mCKHpaI | CAGTGAGCAGTTAACATCTGGAGG (SEQ ID NO: 65) | (66.23° C.) | 24 |
| mCG1XcmI | CTAACTCCATGGTGACCCTGGGATG (SEQ ID NO: 66) | (72.17° C.) | 25 |

| Kappa Framework 1 Specific Primers: (R = A + G, M = A + C, K = G + T, W = A + T, S = C + G) | | |
|---|---|---|
| TMX24mVK1 | GACGACCGGCTACCAAGAGGAGTGTCTAGAGACATTGTGAT GWCACAGTCTC (SEQ ID NO: 6) | 52 |
| TMX24mVK2 | GACGACCGGCTACCAAGAGGAGTGTCTAGAGATGTTKTGAT GACCCARACTC (SEQ ID NO: 7) | 52 |
| TMX24mVK3 | GACGACCGGCTACCAAGAGGAGTGTCTAGAGACATTGTGAT GACKCAGGCTG (SEQ ID NO: 8) | 52 |
| TMX24mVK4 | GACGACCGGCTACCAAGAGGAGTGTCTAGAGACAWTGTGCT GACCCARTCTC (SEQ ID NO: 9) | 52 |
| TMX24mVK5 | GACGACCGGCTACCAAGAGGAGTGTCTAGAGAAAWTGTGCT CACCCAGTCTC (SEQ ID NO: 10) | 52 |
| TMX24mVK6 | GACGACCGGCTACCAAGAGGAGTGTCTAGAGACATCCAGAT GACMCAGTCTC (SEQ ID NO: 11) | 52 |
| TMX24mVK7 | GACGACCGGCTACCAAGAGGAGTGTCTAGAGATATCCAGAT GACACAGACTAC (SEQ ID NO: 12) | 53 |
| TMX24mVK8 | GACGACCGGCTACCAAGAGGAGTGTCTAGAGACATTGTSAT GACCCAGTC (SEQ ID NO: 13) | 50 |

Kappa Framework 1 Specific Primers:
(R = A + G, M = A + C, K = G + T, W = A + T, S = C + G)

| | | |
|---|---|---|
| TMX24mVK9 | GACGACCGGCTACCAAGAGGAGTGTCTAGACAAATTGTTCT CACCCAGTCTC (SEQ ID NO: 14) | 52 |
| TMX24mVK10 | GACGACCGGCTACCAAGAGGAGTGTCTAGAGACATCKTGCT SACTCAGTCTC (SEQ ID NO: 15) | 52 |
| TMX24mVK11 | GACGACCGGCTACCAAGAGGAGTGTCTAGAGATATTGTGAT AACCCAGGATG (SEQ ID NO: 16) | 52 |
| TMX24mVK12 | GACGACCGGCTACCAAGAGGAGTGTCTAGAAGYATTGTGAT GACCCAGWCTC (SEQ ID NO: 17) | 52 |
| TMX24mVK13 | GACGACCGGCTACCAAGAGGAGTGTCTAGAGACATCCAGAT GACACAATCTTC (SEQ ID NO: 18) | 53 |

Heavy Chain Framework 1 Specific Primers:
(R = A + G, M = A + C, Y = C + T, S = C + G)

| | | |
|---|---|---|
| TMX24mVH1 | GACGTGGCCGTTGGAAGAGGAGTGCTCGAGGTGCAGCTTCA GSAGTC (SEQ ID NO: 19) | 47 |
| TMX24mVH2 | GACGTGGCCGTTGGAAGAGGAGTGCTCGAGGTGCAGCTGAA GSAGTC (SEQ ID NO: 20) | 47 |
| TMX24mVH3 | GACGTGGCCGTTGGAAGAGGAGTGCTCGAGGTCCAGCTGCA ACAGTTTG (SEQ ID NO: 21) | 49 |
| TMX24mVH4 | GACGTGGCCGTTGGAAGAGGAGTGCTCGAGGTYCAGCTGCA RCARTC (SEQ ID NO: 22) | 47 |
| TMX24mVH5 | GACGTGGCCGTTGGAAGAGGAGTGCTCGAGGTCCAACTGCA GCAGYC (SEQ ID NO: 23) | 47 |
| TMX24mVH6 | GACGTGGCCGTTGGAAGAGGAGTGCTCGAGGTTCAGCTGCA GCAGTC (SEQ ID NO: 24) | 47 |
| TMX24mVH7 | GACGTGGCCGTTGGAAGAGGAGTGCTCGAGGTGAAGCTGGT GGAGWC (SEQ ID NO: 25) | 47 |
| TMX24mVH8 | GACGTGGCCGTTGGAAGAGGAGTGCTCGAGGTGAAGCTTCT GGAGTC (SEQ ID NO: 26) | 47 |
| TMX24mVH9 | GACGTGGCCGTTGGAAGAGGAGTGCTCGAGGTGMAGCTGGT GGAGTC (SEQ ID NO: 27) | 47 |
| TMX24mVH10 | GACGTGGCCGTTGGAAGAGGAGTGCTCGAGGTGAAGCTTCT GGAGTCTGG (SEQ ID NO: 28) | 50 |
| TMX24mVH11 | GACGTGGCCGTTGGAAGAGGAGTGCTCGAGGTGAAGCTTGA GGAGTC (SEQ ID NO: 29) | 47 |
| TMX24mVH12 | GACGTGGCCGTTGGAAGAGGAGTGCTCGAGGTTACTCTGAA AGAGTC (SEQ ID NO: 30) | 47 |
| TMX24mVH13 | GACGTGGCCGTTGGAAGAGGAGTGCTCGAGATCCAGTTGGT GCAGTC (SEQ ID NO: 31) | 47 |

Adaptor Oligonucleotides

| | | |
|---|---|---|
| mCKAd1 | CTCTCTCCATCTTCCCACCATCCAGTGAGCAGTTGAC ATCCGGACACTCCTCTTGGTAGCCGGTCGTC (SEQ ID NO: 2) | 68 |
| mCKAd2 | GACGACCGGCTACCAAGAGGAGTGTCCGGATGTC (SEQ ID NO: 4) | 34 |
| mCG1Ad1 | CCCTGGATCTGCTGCCCAAACTAACTCCATGGTCACT CCTCTTCCAACGGCCACGTC (SEQ ID NO: 3) | 57 |
| mCG1Ad2 | GACGTGGCCGTTGGAAGAGGAGTG (SEQ ID NO: 5) | 24 |

| | Kappa | IgG1 |
|---|---|---|
| Adapter oligo mix | mCKAd mix | mCG1Ad mix |
| Adapter 1 | mCKAd1 | mCG1Ad1 |
| Adapter 2 | mCKAd2 | mCG1Ad2 |

Primers for Single Primer Amplification

| | | |
|---|---|---|
| TMX24mH | GACGTGGCCGTTGGAAGAGGAGTG (SEQ ID NO: 32) | 24 |
| TMX24mK | GACGACCGGCTACCAAGAGGAGTG (SEQ ID NO: 33) | 24 |

Rabbit
Oligonucleotides for Restriction Digestion of Kappa Chains

| | | |
|---|---|---|
| rK1Re | GTACCTACAACCTCAGCAGYACTCTG (SEQ ID NO: 67) | 50 nmol, HPLC, 20 μM |
| rK2Re | ACCTACAGCCTGAGCAGCACTCTG (SEQ ID NO: 68) | 50 nmol, HPLC, 20 μM |
| rKRe | TACCTACARCCTSAGCAGYACTCTG (SEQ ID NO: 38) | 50 nmol, HPLC, 20 μM |

Oligonucleotides for Restriction Digestion of Heavy Chains

| | | |
|---|---|---|
| rG1/4Re | AGGCTACCTCCCCGAGCCAGTGACCG (SEQ ID NO: 69) | 50 nmol, HPLC, 20 μM |
| rG2/5Re | GCTACCTCCCGGAGCCAGTGACCGTG (SEQ ID NO: 70) | 50 nmol, HPLC, 20 μM |
| rCGRe | CCTCCCSGAGCCAGTGACCGTGACTTG (SEQ ID NO: 39) | HPLC 50 nmol 20 pmol/μL |

Oligonucleotides for Nick Ligation of Kappa Chains

| | | |
|---|---|---|
| rCK1-1Ad1 | CGCAGAATTCTGCAGATTGTACCTACAACCTCAcGTCGACCACTCCTCTTGGTAGCCGGTC GTC (SEQ ID NO: 40) | 50 nmol, PAGE, 20 μM |
| rCK1-2Ad1 | CRCAGAATTCTGATGATTGTACCTACAACCTCAcGTCGACCACTCCTCTTGGTAGCCGGTC GTC (SEQ ID NO: 41) | 50 nmol, PAGE, 20 μM |
| rCK1-3Ad1 | CGCAGAGCCCGAAGACTGTACCTACAACCTCAcGTCGACCACTCCTCTTGGTAGCCGGTC GTC (SEQ ID NO: 42) | 50 nmol, PAGE, 20 μM |
| rCK1-4Ad1 | CGCAGGATCCTACATATTGTACCTACAACCTCAcGTCGACCACTCCTCTTGGTAGCCGGTC GTC (SEQ ID NO: 43) | 50 nmol, PAGE, 20 μM |
| rCK2Ad1 | CGCAGAGCCCYGAAGACAATACCTACAGCCTCAcGTCGACCACTCCTCTTGGTAGCCGGTC GTC (SEQ ID NO: 44) | 50 nmol, PAGE, 20 μM |
| rCK1Ad2 | GACGACCGGCTACCAAGAGGAGTGGTCGACg (SEQ ID NO: 45) | 50 nmol, PAGE, 20 μM |

| Adaptor oligo mix | rCK Ad mix |
|---|---|
| Adapter 1 | rCKAd1 mix (rCK1-1Ad1, rCK1-2Ad1, rCK1-3Ad1, rCK1-4Ad1, rCK2Ad1) (1:1:1:1:1) |
| Adapter 2 | rCK1Ad2 |

Oligonucleotides for Nick Ligation of Heavy Chains

| | | |
|---|---|---|
| rCG1/4Ad1 | GCTGCTTGGTCAAAGGCTACCTCCCCGAaCcg GTCACTCCTCTTCCAACGGCCACGTC (SEQ ID NO: 46) | 50 nmol, PAGE, 20 μM |
| rCG2/5Ad1 | GCTGCcTGGTCAAAGGCTACCTCCCGGAaCcg GTCACTCCTCTTCCAACGGCCACGTC (SEQ ID NO: 47) | 50 nmol, PAGE, 20 μM |
| rCGAd2 | GACGTGGCCGTTGGAAGAGGAGTGACcGGt (SEQ ID NO: 48) | 50 nmol, PAGE, 20 μM |

| Adaptor oligo mix | rCG Ad mix |
|---|---|
| Adapter 1 | rCG1/4Ad1:rCG2/5Ad1 (1:1) |
| Adapter 2 | rCGAd2 |

Rabbit kappa chain framework 1 specific primers
(R = A + G, M = A + C, K = G + T, W = A + T, S = C + G)

| Primer | Sequence | |
|---|---|---|
| TMX24rVK1 | GACGACCGGCTACCAAGAGGAGTGTCTAGAG ACATTGTGCTGACCCAG (SEQ ID NO: 49) | 50 nmol, HPLC, 20 μM |
| TMX24rVK2 | GACGACCGGCTACCAAGAGGAGTGTCTAGAG ACCCTRTGMTGACCCAG (SEQ ID NO: 50) | 50 nmol, HPLC, 20 μM |
| TMX24rVK3 | GACGACCGGCTACCAAGAGGAGTGTCTAGAG ATGKYGTGATGACCCAG (SEQ ID NO: 51) | 50 nmol, HPLC, 20 μM |

Rabbit kappa chain framework 1 specific primers
(R = A + G, M = A + C, K = G + T, W = A + T, S = C + G)

| Primer | Sequence | |
|---|---|---|
| TMX24rVK4 | GACGACCGGCTACCAAGAGGAGTGTCTAGAG CAGCCGTGMTGACCCAG (SEQ ID NO: 52) | 50 nmol, HPLC, 20 µM |
| TMX24rVK5 | GACGACCGGCTACCAAGAGGAGTGTCTAGAG CCATCRAAATGACCCAG (SEQ ID NO: 53) | 50 nmol, HPLC, 20 µM |
| TMX24rVK6 | GACGACCGGCTACCAAGAGGAGTGTCTAGAG CYCAAGKGMTGACCCAG (SEQ ID NO: 54) | 50 nmol, HPLC, 20 µM |
| TMX24rVK7 | GACGACCGGCTACCAAGAGGAGTGTCTAGAG CSCTSGTGMTGACCCAG (SEQ ID NO: 55) | 50 nmol, HPLC, 20 µM |
| TMX24rVK8 | GACGACCGGCTACCAAGAGGAGTGTCTAGATA TGTCATGATGACCCAG (SEQ ID NO: 56) | 50 nmol, HPLC, 20 µM |

Rabbit heavy chain framework 1 specific primers
(R = A + G, M = A + C, K = G + T, W = A + T, S = C + G)

| Primer | Sequence | |
|---|---|---|
| TMX24rVH1a | GACGTGGCCGTTGGAAGAGGAGTGCTCGAGCAG GAGCAGCTGAAGGAGtc (SEQ ID NO: 57) | 50 nmol, HPLC, 20 µM |
| TMX24rVH2d | GACGTGGCCGTTGGAAGAGGAGTGCTCGAGCAGT CAGTGAAGGAGTCCga (SEQ ID NO: 58) | 50 nmol, HPLC, 20 µM |
| TMX24rVH3L | GACGTGGCCGTTGGAAGAGGAGTGCTCGAGCAGT CGCTGGRGGAGTCCrg (SEQ ID NO: 59) | 50 nmol, HPLC, 20 µM |
| TMX24rVH3b | GACGTGGCCGTTGGAAGAGGAGTGCTCGAGCAGT CGYTGGgGGAGTCCrg (SEQ ID NO: 60) | 50 nmol, HPLC, 20 µM |
| TMX24rVH4L | GACGTGGCCGTTGGAAGAGGAGTGCTCGAGCAGT CGKTGGAGGAGTCCrg (SEQ ID NO: 61) | 50 nmol, HPLC, 20 µM |
| TMX24rVH4a | GACGTGGCCGTTGGAAGAGGAGTGCTCGAGCAGT CGgTGGAGGAGTCCrg (SEQ ID NO: 62) | 50 nmol, HPLC, 20 µM |
| TMX24rVH7L | GACGTGGCCGTTGGAAGAGGAGTGCTCGAGCAG WCRGTGAAGGAGTCCga (SEQ ID NO: 63) | 50 nmol, HPLC, 20 µM |
| TMX24rVH8L | GACGTGGCCGTTGGAAGAGGAGTGCTCGAGCAGT CGCTGGAGGAATTCgg (SEQ ID NO: 64) | 50 nmol, HPLC, 20 µM |

(K = G + T, M = A + C, R = A + G, S = C + G, W = A + T, Y = C + T)

Primers for Single Primer Amplification

| Primer | Sequence | Length |
|---|---|---|
| TMX24mH | GACGTGGCCGTTGGAAGAGGAGTG (SEQ ID NO: 5) | 24 |
| TMX24mK | GACGACCGGCTACCAAGAGGAGTG (SEQ ID NO: 33) | 24 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for creating an engineered template configured for amplification with a single primer, the engineered template comprising a polynucleotide having a 5' end and a 3' end with a first pre-determined sequence disposed at the 5' end and a second pre-determined sequence complement of and reverse of the first pre-determined sequence disposed at the 3' end, the method comprising:
   (a) creating a double-stranded portion of the polynucleotide at a cleavage site;
   (b) cleaving the double-stranded portion of the polynucleotide at the cleavage site;
   (c) annealing a first portion of a first adaptor oligonucleotide to a first portion of the polynucleotide and a second portion of the first oligonucleotide to a first portion of a second adaptor oligonucleotide, the second adaptor oligonucleotide comprising a first pre-determined sequence;
   (d) ligating the polynucleotide of (b) to the second adaptor oligonucleotide of (c), wherein the ligation occurs between a 5' end of the polynucleotide of (b) and a 3' end of the second adaptor oligonucleotide of (c), wherein the ligation creates a pre-engineered template with the first pre-determined sequence on the first portion of the polynucleotide;
   (e) annealing a set of primers to the pre-engineered template, wherein each primer further comprises the first pre-determined sequence, a restriction site, and a portion that anneals to the polynucleotide; and,
   (f) synthesizing the engineered template such that the engineered template comprises the first pre-determined sequence disposed at the 5' end and the second pre-determined sequence complement of and reverse of the first pre-determined sequence disposed at the 3' end.

2. The method of claim 1, wherein the first pre-determined sequence further comprises a universal sequence, wherein the universal sequence is the same as a universal sequence of a primer.

3. The method of claim 1, further comprising step (g), synthesizing a second polynucleotide from the engineered template.

4. The method of claim 1, wherein at least the engineered template and at least a different engineered template are combined into a single synthesis reaction.

5. The method of claim 4, wherein the polynucleotide of the engineered template and a polynucleotide of the different engineered template comprise a different nucleotide sequence.

6. The method of claim 1, wherein the engineered template is used in a synthesis reaction.

7. The method of claim 2, further comprising step (g), amplifying the engineered template with the primer.

8. The method of claim 1, wherein the polynucleotide is either a first strand cDNA or a second strand cDNA.

9. The method of claim 1, wherein ligating further comprises a DNA ligase and nick ligation.

10. The method of claim 1, wherein steps (a)-(d) do not comprise a polymerase.

11. The method of claim 1, wherein the cleaving occurs at any site recognized by a restriction enzyme within the double-stranded polynucleotide.

12. The method of claim 1, wherein the pre-engineered template of step (d) does not contain an adenosine introduced by polymerase and not encoded by a nucleotide sequence of the polynucleotide at the 3' end of the polynucleotide.

13. The method of claim 1, wherein the first portion of the first adaptor oligonucleotide is disposed near the 5' end of the first adaptor oligonucleotide.

14. The method of claim 1, wherein the first portion of the polynucleotide is disposed near the 5' end of the polynucleotide.

15. The method of claim 1, wherein the second portion of the first adaptor oligonucleotide is disposed near the 3' end of the first adaptor oligonucleotide.

16. The method of claim 1, wherein the first portion of the second adaptor oligonucleotide is disposed near the 5' end of the second adaptor oligonucleotide.

17. The method of claim 1, wherein a second portion of the pre-engineered template is disposed near the 3' end of the polynucleotide.

18. The method of claim 1, wherein the first predetermined sequence and the second predetermined sequence further comprise a universal sequence.

19. The method of claim 1, wherein the adaptor oligonucleotides are annealed together prior to annealing the adaptor oligonucleotides to the cleaved polynucleotide.

20. The method of claim 1, wherein the first pre-determined sequence and the second pre-determined sequence are not substantially similar to any sequence within the polynucleotide.

21. The method of claim 1, wherein a primer of the amplification with single primer comprises a first pre-determined sequence.

22. The method of claim 1, wherein the set of primers of step (e) are pre-mixed.

23. The method of claim 1, wherein the synthesizing of step (f) further comprises DNA polymerase.

24. The method of claim 1, wherein the second oligonucleotide further comprises a restriction site.

25. The method of claim 1, wherein the engineered template further comprises a polynucleotide corresponding to an immunoglobulin gene.

26. The method of claim 1, wherein the method further comprises step (g), constructing an antibody library from the engineered template.

* * * * *